(12) United States Patent
Keler et al.

(10) Patent No.: US 9,169,325 B2
(45) Date of Patent: Oct. 27, 2015

(54) ANTIBODIES THAT BIND HUMAN CD27 AND USES THEREOF

(75) Inventors: Tibor Keler, Ottsville, PA (US); Henry C. Marsh, Reading, MA (US); Lizhen He, Allentown, PA (US); Laura A. Vitale, Doylestown, PA (US); Lawrence J. Thomas, Easton, MA (US)

(73) Assignee: Celldex Therapeutics, Inc., Needham, MA (US)

( * ) Notice: Subject to any disclaimer, the term of this patent is extended or adjusted under 35 U.S.C. 154(b) by 1203 days.

(21) Appl. No.: 13/086,286

(22) Filed: Apr. 13, 2011

(65) Prior Publication Data

US 2011/0274685 A1  Nov. 10, 2011

Related U.S. Application Data

(60) Provisional application No. 61/323,720, filed on Apr. 13, 2010, provisional application No. 61/471,459, filed on Apr. 4, 2011.

(51) Int. Cl.
*C07K 16/28* (2006.01)
*A61K 39/00* (2006.01)

(52) U.S. Cl.
CPC ....... *C07K 16/2878* (2013.01); *A61K 2039/505* (2013.01); *C07K 2317/732* (2013.01); *C07K 2317/734* (2013.01); *C07K 2317/74* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,506,126 A | 4/1996 | Seed et al. |
| 5,830,731 A | 11/1998 | Seed et al. |
| 5,849,898 A | 12/1998 | Seed et al. |
| 6,010,853 A | 1/2000 | Kanteti et al. |
| 6,111,093 A | 8/2000 | Seed et al. |
| 6,218,525 B1 | 4/2001 | Seed et al. |
| 7,119,183 B2 | 10/2006 | Seed et al. |
| 8,481,029 B2 | 7/2013 | Glennie et al. |
| 2003/0035790 A1 | 2/2003 | Chen et al. |
| 2004/0072283 A1 | 4/2004 | Seed et al. |
| 2004/0170982 A1 | 9/2004 | Morris et al. |
| 2006/0228710 A1 | 10/2006 | Morris et al. |
| 2007/0149449 A1 | 6/2007 | Morris et al. |
| 2007/0212351 A1 | 9/2007 | Morris et al. |
| 2010/0173324 A1 | 7/2010 | Mori et al. |
| 2011/0033449 A1 | 2/2011 | Glennie et al. |
| 2011/0052579 A1 | 3/2011 | Weiss et al. |
| 2012/0213771 A1 | 8/2012 | Keler et al. |
| 2013/0336976 A1 | 12/2013 | Glennie et al. |

FOREIGN PATENT DOCUMENTS

| | | |
|---|---|---|
| EP | 0330191 A2 | 8/1989 |
| EP | 0739980 A2 | 10/1996 |
| EP | 2090320 A1 | 8/2009 |
| EP | 2698382 A1 | 2/2014 |
| WO | 89/08114 A1 | 9/1989 |
| WO | 92/01049 A2 | 1/1992 |
| WO | 96/34096 A1 | 10/1996 |
| WO | 98/54323 A1 | 12/1998 |
| WO | 00/41508 A2 | 7/2000 |
| WO | 03/068268 A2 | 8/2003 |
| WO | 2004/023973 A2 | 3/2004 |
| WO | 2004/074320 A2 | 9/2004 |
| WO | 2004/074321 A2 | 9/2004 |
| WO | 2008/051424 A2 | 5/2008 |
| WO | 2009/100942 A1 | 8/2009 |
| WO | 2010/001908 A1 | 1/2010 |

OTHER PUBLICATIONS

George et al. (Circulation. 1998; 97: 900-906).*
Greenspan et al. (Nature Biotechnology. 1999; 7: 936-937).*
Daniel et al (Virology, 202:540-549, 1994).*
Lippincott-Schwartz (Current Protocols in Cell Biology, 16.0.1-16.0.2, 2002).*
Bigler, Robert D. et all., "A Novel Disulfide-Linked Cell Surface Molecule Present on Resting and Activated Human T Lymphocytes," Leukocyte Typing II, vol. 1, Human T Lymphocytes, Ellis L. Reinherz (Ed.), Springer-Verlag, New York, Chpt. 41, pp. 503-512 (1986).
Florido, Manuela et al., "Contribution of CD30/CD153 but not of CD27/CD70, Cd134/OX40L, or CD137/4-1BBL to the optimal induction of protective immunity to Mycobacterium avium," Journal of Leukocyte Biology, vol. 76:1039-1046 (2004).
French, Ruth R. et al., "Eradication of lymphomoa by CD8 T cells following anti-CD40 monoclonal antibody therapy is critically dependent on CD27 costimulation," Blood, vol. 109(11):4810-4815 (2007).
Gravestein, Loes A. et al., "Novel mAbs reveal potent co-stimulatory activity of murine CD27," International Immunology, vol. 7(4):551-557 (1995).
He, LiZhen et al., "Development of Novel Anti-CD27 Human Antibodies with Therapeutic Potential," Proceedings of the American Association for Cancer Research Annual Meeting, vol. 51:1295 (2010).
He, LiZhen et al., "Development of Novel Anti-CD27 Human Antibodies with Therapeutic Potential," 101st Annual Meeting of the American-Association-for-Cancer-Research, Abstract No. 5343 (2010).
Hirano, Testuo et al., "CD27 synergizes with CD40 to induce IgM, IgG, and IgA antibody responses of peripheral blood B cells in the presence of IL-2 and IL-10," Immunology Letters, vol. 89:251-257 (2003).

(Continued)

*Primary Examiner* — Brad Duffy
(74) *Attorney, Agent, or Firm* — Nelson Mullins Riley & Scarborough LLP; Jane E. Remillard, Esq.

(57) ABSTRACT

Isolated monoclonal antibodies which bind to human CD27 and related antibody-based compositions and molecules are disclosed. Also disclosed are therapeutic and diagnostic methods for using the antibodies.

19 Claims, 34 Drawing Sheets

(56) References Cited

OTHER PUBLICATIONS

Kobata, Tetsuji et al., "CD27-CD70 interactions regulate B-cell activation by T cells," Proc. Natl. Acad. Sci. USA, vol. 92:11249-11253 (1995).

Matter, Matthias et al., "Elimination of chronic viral infection by blocking CD27 signaling," The Journal of Experimental Medicine, vol. 203(9):2145-2155 (2006).

McMichael, Andrew J. et al., "T-cell antigens: new and previously defined clusters," Leucocyte Typing III, White Cell Differentiation Antigens, A.J. McMichael (Ed.), Oxford University Press, Oxford, Chpt. 5.1, pp. 31-62 (1987).

Ramakrishna, Venky et al., "In vitro characterization of novel anti-human CD27 mAbs," The Journal of Immunology, vol. 184, Abstract No. 87.23 (2010).

Rudikoff, Stuart et al., "Single amino acid substitution altering antigen-binding specificity," Proc. Natl. Acad. Sci. USA, vol. 79:1979-1983 (1982).

Sakanishi, Tamami et al., "Anti-tumor effects of depleting and non-depleting anti-CD27 monoclonal antibodies in immune-competent mice," Biochemical and Biophysical Research Communication, vol. 393:829-835 (2010).

Stockinger, Hannes et al., "T14, A Non-modulating 150-Kd T Cell Surface Antigen," Leukocyte Typing II, vol. 1, Human T Lymphocytes, Ellis L. Reinherz (Ed.), Springer-Verlag, New York, Chpt. 42, pp. 513-529 (1986).

Sugita, Kanji et al., "The 1A4 Molecule (CD27) is Involved in T Cell Activation," The Journal of Immunology, vol. 147 (5):1477-1483 (1991).

Takeda, Kazuyoshi et al., "CD27-Mediated Activation of Murine NK Cells," The Journal of Immunology, vol. 164:1741-1745 (2000).

Van Lier, Rene A.W. et al., "Tissue Distribution and Biochemical and Functional Properties of Tp55 (CD27), a Novel T Cell Differentiation Antigen," The Journal of Immunology, vol. 139:1589-1596 (1987).

Yang, F.C. et al., "CD27/CD70 interaction directly induces natural killer cell killing activity," Immunology, vol. 88:289-293 (1996).

International Search Report for Application No. PCT/US2011/032355, dated Jan. 17, 2012.

Invitation to Pay Additional Fees for Application No. PCT/US2011/032355, dated Oct. 5, 2011.

Kobata, Tetsuji et al., "CD27 Is a Signal-Transducing Molecule Involved in CD45RA+ Naive T Cell Costimulation," The Journal of Immunology, vol. 153:5422-5432 (1994).

\* cited by examiner

Biacore Analysis of Human CD27mAbs

| Clone | Dissociation Time (sec) | ka (1/Ms) | kd (1/s) | Rmax (RU) Fc2-1 | Rmax (RU) Fc4-3 | KA (1/M) | KD (M) |
|---|---|---|---|---|---|---|---|
| 1G5 | 480 | 2.23E+05 | 8.98E-05 | 236 | 177 | 2.55E+09 | 4.02E-10 |
| 1H8 | 480 | 2.18E+05 | 3.44E-05 | 313 | 226 | 6.39E+09 | 1.58E-10 |
| 3H12 | 480 | 1.74E+05 | 6.23E-05 | 298 | 205 | 2.80E+09 | 3.58E-10 |
| 3H8 | 1200 | 1.12E+05 | 6.19E-06 | 126 | 96 | 1.81E+10 | 5.56E-11 |
| 2G9 | 1200 | 1.74E+05 | 2.65E-07 | 97 | 75 | 6.60E+11 | 1.53E-12 |
| 1F5 | 480 | 3.07E+05 | 5.72E-05 | 312 | 206 | 5.37E+09 | 1.86E-10 |
| 3A10 | 480 | 1.74E+06 | 3.51E-04 | 113 | 79 | 4.97E+09 | 2.02E-10 |
| 2C2 | 480 | 5.03E+05 | 4.23E-05 | 54 | 40 | 1.20E+10 | 8.41E-11 |

*Fig. 1*

VHs Alignment

```
                    1                                                  50
1F5-1H5  V-H   (1)  MEFGLSWVFLVALLRGVQCQVQLVESGGGVVQPGRSLRLSCAASGFTFSS
1G5-1B9  V-H   (1)  MEFGLSWVFLVALLRGVQCQVQLVESGGGVVQPGRSLRLSCAASGFSFSS
1H8-B4   V-H   (1)  MEFGLSWVFLVALLRGVQCQVQLVESGGGVVQPGRSLRLSCAASGFTFNI
2C2-1A10 V-H   (1)  MEFGLSWVFLVALLRGVQCQVQLVESGGGVVQPGRSLRLSCAASGFTFSS
2G9-1D11 V-H   (1)  MEFGLSWVFLVALLRGVQCQVQLVESGGGVVQPGRSLRLSCAASGFTLSS
3A10-1G10 V-H  (1)  MEFGLSWVFLVALLRGVQCQVQLVESGGGVVQPGRSLRLSCAASGFTFSH
3H12-1E12 V-H  (1)  MEFGLSWVFLVALLRGVQCQVQLVESGGGVVQPGRSLRLSCATSGFTFSS
3H8-1B11  V-H  (1)  MELGLSWVFLVAILEGVQCEVQLVESGGGLVQPGGSLRLSCAASGFTFSS
                    51                                                 100
1F5-1H5  V-H   (51) YDMHWVRQAPGKGLEWVAVIWYDGSNKYYADSVKGRFTISRDNSKNTLYL
1G5-1B9  V-H   (51) YGMHWVRQAPGKGLEWVALLWYDGSHKDFADSVKGRFTISRDNSKNTLDL
1H8-B4   V-H   (51) YDMHWVRQAPGKGLEWVAVIWYDGSNQYYADSVKGRFTISRDNSKNTLYL
2C2-1A10 V-H   (51) YDIHWVRQAPGKGLEWVAVIWNDGSNKYYADSVKGRFTISRDNSTNSLFL
2G9-1D11 V-H   (51) HDIHWVRQAPGKGLEWVAVIWNDGSNKYYADSVKGRFTISRDNSTNSLFL
3A10-1G10 V-H  (51) YGMHWVRQAPGKGPEWVAIIWYDGSNKYYADSVKGRFTISRDNSKNTLDL
3H12-1E12 V-H  (51) YDMHWVRQAPGKGLEWVAVIWYDGSNKYYADSVKGRFTISRDNSKNTLYL
3H8-1B11  V-H  (51) YWMAWVRQAPGKGLEWLGNIKQDGSEKYYVDSVKGRFTISRDNAKNSLYL
                    101                              143
1F5-1H5  V-H   (101) QMNSLRAEDTAVYYCARGSGN------WGFFDYWGQGTLVTVSS
1G5-1B9  V-H   (101) QMNSLRAEDTAVYYCAREGLAVPG--HWYFDLWGRGTLVTVSS
1H8-B4   V-H   (101) QMNILRAEDTAVYYCARG-TH------WGYFDYWGQGTLVTVSS
2C2-1A10 V-H   (101) QMNSLRAEDTAVYYCVGG--------TADLEHWDQGTLVTVSS
2G9-1D11 V-H   (101) QMNSLRAEDTAVYYCVRG--------TADLEHWDQGTLVTVSS
3A10-1G10 V-H  (101) QMNSLRAEDTAVYYCARDGWTTMVRGLNVFDIWGQGTMVTVSS
3H12-1E12 V-H  (101) QMNSLGDEDTAVYYCARGSGN------WGFFDYWGQGTLVTVSS
3H8-1B11  V-H  (101) QMNSLRAEDTAVYYCVRELG------MDWYFDLWGRGTLVTVSS
```

*Fig. 15*

VKs Alignment

|  | | 1 | | 50 |
|---|---|---|---|---|
| 1F5-1H5 V-L #2 | (1) | MRVLAQLLGLLLLCFPGARCDIQMTQSPSSLSASVGDRVTITCRASQGIS |
| 1G5-1B9 V-L | (1) | MRVPAQLLGLLLLWLPGARCAIQLTQSPSSLSASVGDRVTITCRASQGIS |
| 1H8-B4 V-L | (1) | MRVLAQLLGLLLLCFPGARCDIQMTQSPSSLSASVGDRVTITCRASQGIS |
| 2C2-1A10 V-L | (1) | MRVLAQLLGLLLLCFPGARCDIQMTQSPSSLSASVGDRVTITCRASQGIS |
| 2G9-1D11 V-L | (1) | MRVLAQLLGLLLLCFPGARCDIQMTQSPSSLSASVGDRVTITCRASQGIS |
| 3A10-1G10 V-L #2 | (1) | MRVPAQLLGLLLLWLPGARCAIQLTQSPSSLSASVGDRVTITCRASQGIS |
| 3H12-1E12 V-L #2 | (1) | MRVLAQLLGLLLLCFPGARCDIQMTQSPSSLSASVGDRVTITCRASQGIS |
| 3H8-1B11 V-L #2 | (1) | MEAPAQLLFLLLLWLPDTTGEIVLTQSPATLSLSPGERATLSCRASQSVD |

|  | | 51 | | 100 |
|---|---|---|---|---|
| 1F5-1H5 V-L #2 | (51) | RWLAWYQQKPEKAPKSLIYAASSLQSGVPSRFSGSGSGTDFTLTISSLQP |
| 1G5-1B9 V-L | (51) | SALAWYQQKPGKAPKLLIYDASSLESGVPSRFSGSGSGTDFTLTISSLQP |
| 1H8-B4 V-L | (51) | SWLAWYQQKPEKAPKSLIYAASNLQSGVPSRFSGSGSGTDFTLTISSLQP |
| 2C2-1A10 V-L | (51) | SWLAWYQQKPEKAPKSLIYAASSLQSGVPSRFSGSGSGTDFTLTISSLQP |
| 2G9 1D11 V-L | (51) | SWLAWYQQKPEKAPKSLIYAASSLQSGVPSRFSGSGSGTDFTLTISSLQP |
| 3A10-1G10 V-L #2 | (51) | SALAWYQQKPGKAPKLLIYDASSLESGVPSRFSGSGSGTDFTLTISSLQP |
| 3H12-1E12 V-L #2 | (51) | RWLAWYQQKPEKAPKSLIYAASSLQSGVPSRFSGSGSGTDFTLTISSLQP |
| 3H8-1B11 V-L #2 | (51) | SYLAWYQQKPGQAPRLLIYDASNRATGIPARFSGSGSGTDFTLTISNLEP |

|  | | 101 | | 127 |
|---|---|---|---|---|
| 1F5-1H5 V-L #2 | (101) | EDFATYYCQQYNTYPRTFGQGTKVEIK |
| 1G5-1B9 V-L | (101) | EDFATYYCQQFNTYPRTFGQGTKVEIK |
| 1H8-B4 V-L | (101) | EDFATYYCQQYNSYPRTFGQGTKVEIK |
| 2C2-1A10 V-L | (101) | EDFATYYCQQYNSYPLTFGGGTKVEIK |
| 2G9 1D11 V-L | (101) | EDFATYYCQQYNSYPLTFGGGTKVEIK |
| 3A10-1G10 V-L #2 | (101) | EDFATYYCQQFNSYPFTFGPGTKVDIK |
| 3H12-1E12 V-L #2 | (101) | EDFATYYCQQYNTYPRTFGQGTKVEIK |
| 3H8-1B11 V-L #2 | (101) | EDFAVYYCQQRSNWPPTFGQGTKVEIK |

*Fig. 16*

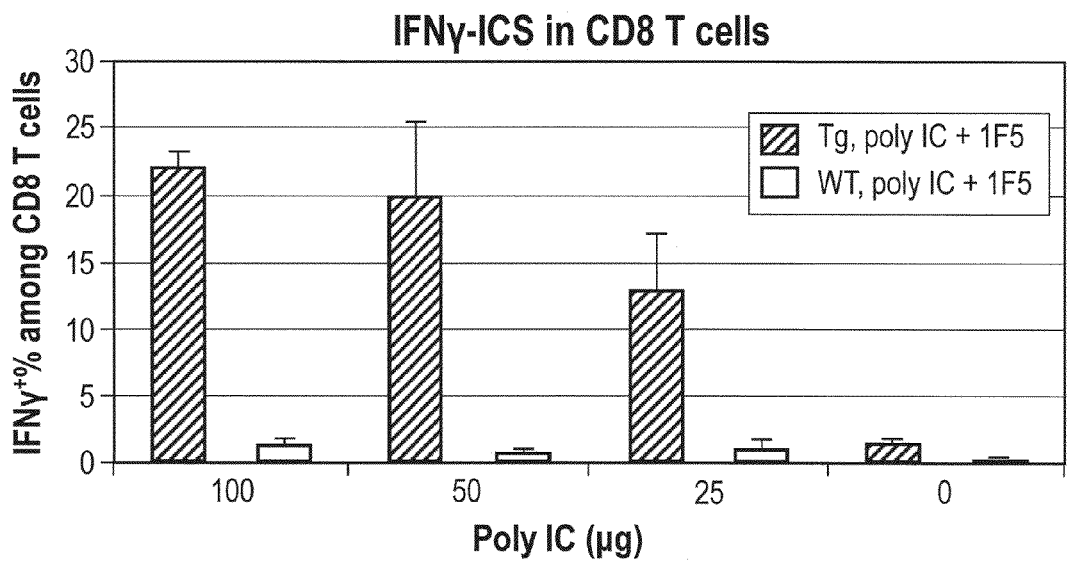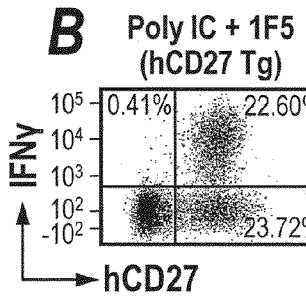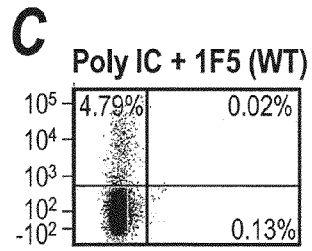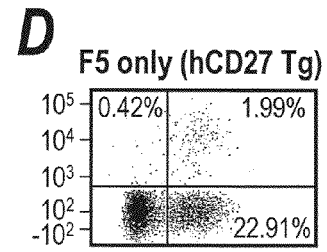
Fig. 23

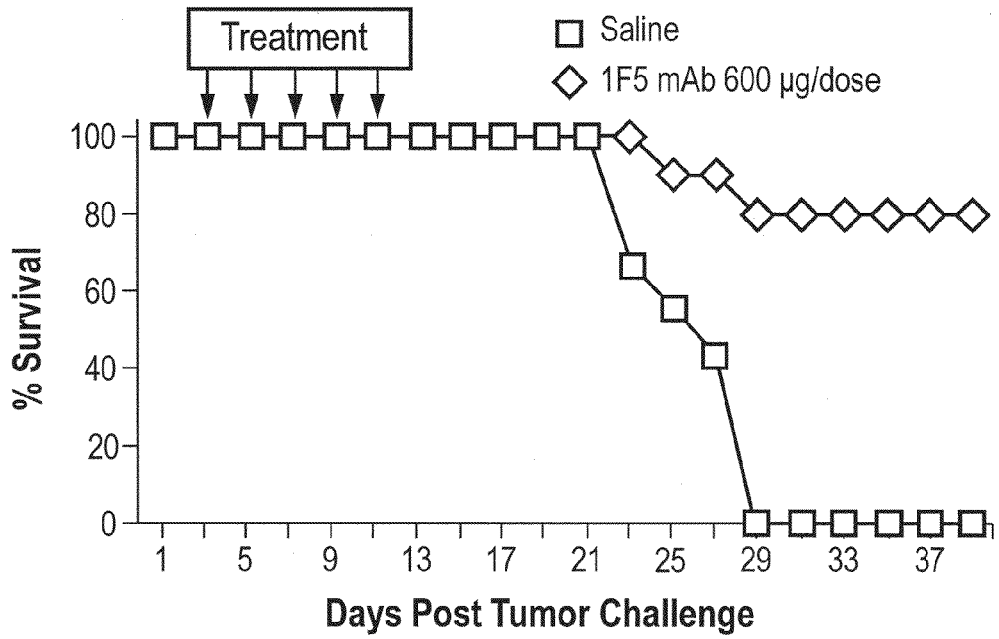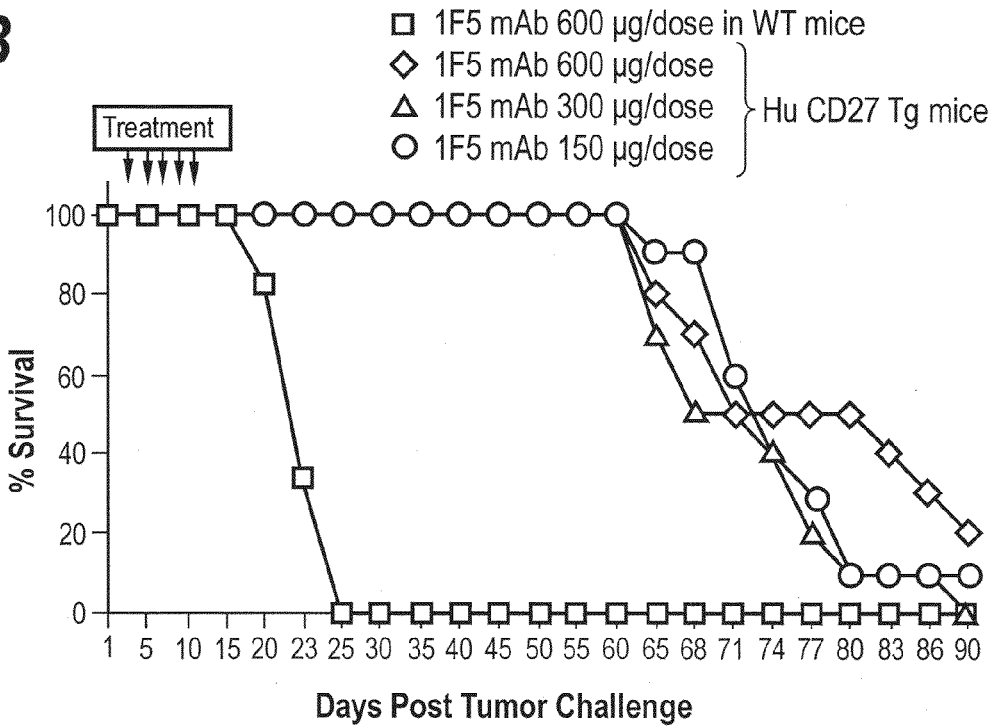
Fig. 29

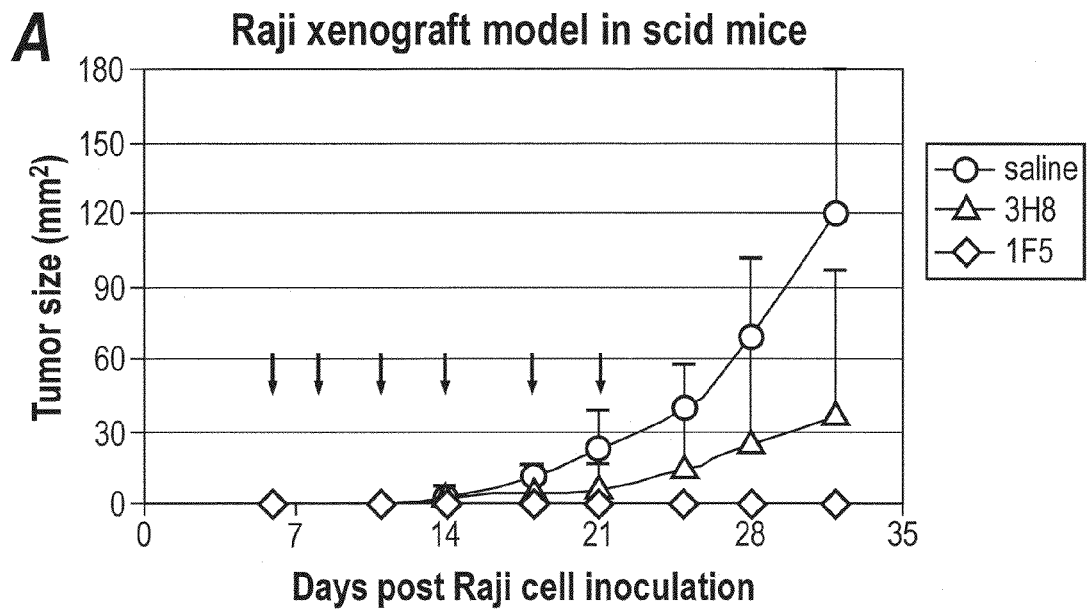
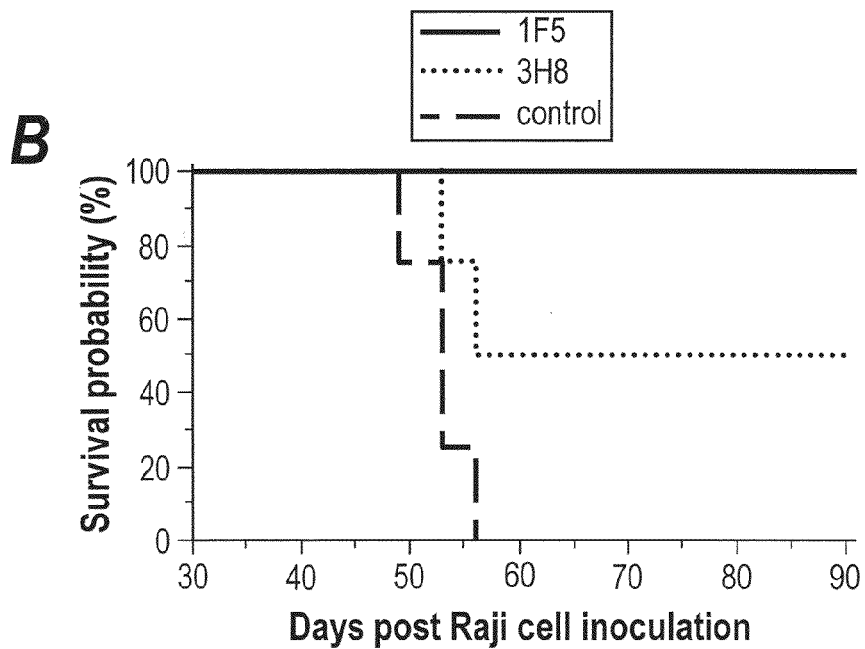
*Fig. 30*

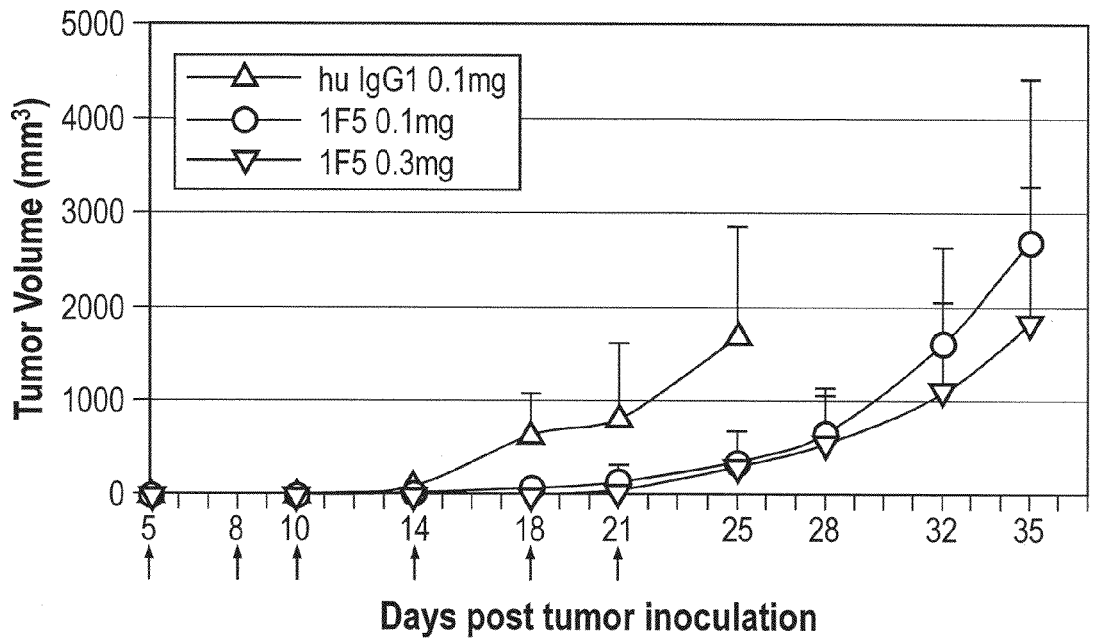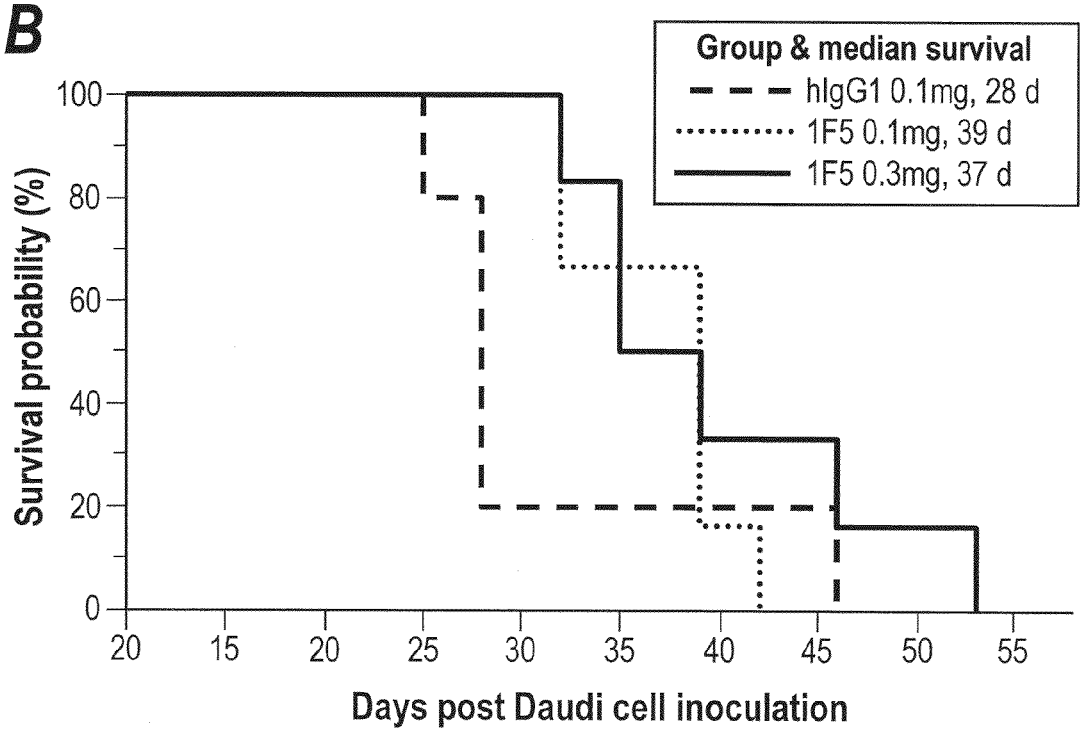
Fig. 33

ANTIBODIES THAT BIND HUMAN CD27 AND USES THEREOF

SEQUENCE LISTING

The instant application contains a Sequence Listing which has been submitted in ASCII format via EFS-Web and is hereby incorporated by reference in its entirety. Said ASCII copy, created on Jun. 20, 2011, is named CD.1367.txt and is 78,582 bytes in size.

BACKGROUND OF THE INVENTION

Interactions between T cells and antigen-presenting cells involve a variety of accessory molecules that facilitate in the generation of an immune response. One such molecule is CD27, which binds CD70 and belongs to the tumor necrosis factor receptor (TNF-R) superfamily (Ranheim E A, et al., *Blood.* 1995 Jun. 15; 85(12):3556-65). CD27 typically exists as a glycosylated, type I transmembrane protein, frequently in the form of homodimers with a disulfide bridge linking the two monomers. The disulfide bridge is in the extracellular domain close to the membrane (Camerini et al., *J. Immunol.* 147:3165-69 (1991). CD27 may also be expressed in a soluble form (see, e.g., van Oers M H, et al., *Blood.* 1993 Dec. 1; 82(11):3430-6 and Loenen W A, et al., *Eur. J. Immunol.* 22:447, 1992). Cross-linking the CD27 antigen on T cells provides a costimulatory signal that, in concert with T-cell receptor crosslinking, can induce T-cell proliferation and cellular immune activation.

CD27 is expressed on mature thymocytes, on most CD4+ and CD8+ peripheral blood T cells, natural killer cells and B cells (Kobata T, et al., *Proc. Natl. Acad. Sci. USA.* 1995 Nov. 21; 92(24):11249-53). CD27 is also highly expressed on B cell non-Hodgkin's lymphomas and B cell chronic lymphocytic leukemias (Ranheim E A, et al., *Blood.* 1995 Jun. 15; 85(12):3556-65). Additionally, increased levels of soluble CD27 protein have been identified in sera or sites of disease activity in parasitic infection, cytomegalovirus (CMV) infection, sarcoidosis, multiple sclerosis, and B-cell chronic lymphocytic leukemia (Loenen W A, et al., *Eur. J. Immunol.* 22:447, 1992).

Agonistic monoclonal antibodies against CD27 have recently been shown to promote T cell responses and show promise as anti-cancer therapeutics (see e.g., Sakanishi T, et al., *Biochem Biophys. Res. Commun.* 2010 Feb. 18 and WO 2008/051424). However, while the results obtained to date establish CD27 as a useful target for immunotherapy, it is unknown which particular features of anti-CD27 monoclonal antibodies are especially advantageous for therapeutic purposes. As such, there is a need in the art for further insight into the specific functional properties that make anti-CD27 antibodies therapeutically effective, as well as improved therapeutic antibodies against CD27 which are more effective for treating and/or preventing diseases.

SUMMARY OF THE INVENTION

The present invention provides inter alia isolated anti-CD27 antibodies having particular functional properties which can be linked with advantageous and desirable therapeutic effects. Specifically, anti-CD27 monoclonal antibodies capable of up-regulating T cell mediated immune responses (e.g., as evidenced by inducement or enhancement of antigen-specific T cell responses), which are particularly well-suited for combination with vaccine therapies, have been generated and characterized by way of the present invention. In one embodiment, agonist anti-CD27 antibodies can enhance the immune response against cancers or infectious diseases by combination with active vaccination, or by enhancing endogenous immune responses. Such antibodies may also directly or indirectly induce cytokine expression. Additionally, anti-CD27 antibodies that down-regulate T cell mediated immune responses, which are particularly well-suited for treating immune disorders, such as graft rejection, allergy and autoimmune diseases, have been generated and characterized. Still further, anti-CD27 antibodies that inhibit growth of CD27 expressing cells by direct cell killing mechanisms (e.g., antibody dependent cell-mediated cytotoxicity (ADCC) and/or complement dependent cellular cytotoxicity (CDCC)), which are particularly effective in treating a wide variety of diseases involving cell proliferation (e.g., cancers), have been generated and characterized.

In one embodiment, the anti-CD27 antibodies of the present invention exhibit one or more of the following properties:

(a) blocks binding of sCD70 to CD27 by at least about 70% at an antibody concentration of 10 μg/ml;

(b) binds to human CD27 with an equilibrium dissociation constant Kd of $10^{-9}$ M or less, or alternatively, an equilibrium association constant Ka of $10^{+9}$ $M^{-1}$ or greater;

(c) induces specific complement mediated cytotoxicity (CDC) of CD27 expressing cells of at least 10% at an antibody concentration of 3 μg/ml and approximately 6% rabbit serum complement;

(d) induces antibody dependent cell-mediated cytotoxicity (ADCC) specific lysis of CD27 expressing cells of at least 10% at an antibody concentration of 3 μg/ml and ratio of effector:target cells of 75:1;

(e) improves median survival by at least 20% in severe combined immunodeficiency (SCID) mice post tumor cell inoculation in vivo ($5 \times 10^5$ Raji cells or $1 \times 10^6$ Daudi cells) when administered at 0.3 mg (i.p.) at least twice a week for 3 weeks compared to mice to which antibody is not administered;

(f) induces or enhances antigen-specific immune responses in combination with a vaccine or endogenous antigen;

(g) induces or enhances antigen-specific TH1 immune responses in combination with a vaccine or endogenous antigen;

(h) induces or enhances antigen-specific T-cell proliferation or activation in combination with a vaccine or endogenous antigen;

(i) reduces or inhibits T-cell proliferation or activation;

(j) induces or enhances T-cell activity when combined with simultaneous, separate or sequential TCR activation;

(k) blocks binding of sCD70 to CD27 by at least about 70% at an antibody concentration of 10 μg/ml and reduces or inhibits T-cell activity when not capable of binding to, or having reduced binding to Fc receptors;

(l) results in less than 50% depletion of CD3+ T-cells (other than NK cells) in macaques when administered at 3 mg/kg (i.v.) over the period of 29 days immediately following administration; or (m) results in less than 50% depletion of memory B-cells in macaques when administered at 3 mg/kg (i.v.) over the period of 29 days immediately following administration.

In a particular embodiment, the antibodies of the invention exhibit combinations of these functional properties.

Accordingly, in one aspect, the invention provides anti-CD27 antibodies that induce and/or enhance an immune response (e.g., a T cell mediated immune response). In a further embodiment, the antibodies inhibit the binding of CD70 to CD27 on cells. Particular antibodies having these combinations of properties include mAb 1F5 comprising heavy and/or light chain variable regions sequences comprising SEQ ID NOs: 37 and/or 43, respectively). Alternatively, the antibodies do not inhibit the binding of CD70 to CD27 on cells. Particular antibodies having these combinations of properties include mAb 3H8 comprising heavy and/or light chain variable regions sequences comprising SEQ ID NOs: 7 and/or 13, respectively, or 7 and/or 19, respectively). Such anti-CD27 antibodies also can be linked to a second molecule (e.g., as a bispecific molecule) having a binding specificity which is different from the antibody, such as a T cell receptor (e.g., CD3, CD25, CD137, CD154_), or an Fc receptor (e.g., FcγRI (CD64), FcγRIIA (CD32), FcγRIIB1 (CD32), FcγRIIB2 (CD32), FcγRIIIA (CD16a), FcγRIIIB (CD16b), FcεRI, FcεRII (CD23), FcαRI (CD89), Fcα/μR, and FcRn), or an NK receptor (e.g. CD56), or a B cell receptor (e.g. CD19, CD20).

Antibodies intended to be used for induction or enhancement of immune responses according to the present invention may have a functional Fc domain permitting binding to Fc receptors, and may include a mutated Fc domain having increased levels of binding to Fc receptors.

In another aspect, the invention provides anti-CD27 antibodies that down-regulate T cell mediated immune responses by inhibiting the binding of CD27 to CD70 on cells which express these proteins. In a particular embodiment, the antibodies inhibit the binding of soluble CD70 (sCD70) to CD27 expressing cells by at least about 70%. Particular antibodies falling within this class include, e.g., mAb comprising heavy and/or light chain variable regions sequences comprising SEQ ID NOs: 37 and/or 43 (mAb 1F5), SEQ ID NOs: 49 and/or 55 (mAb 1H8), or SEQ ID NOs: 103 and/or 109 (mAb 3H12).

In yet another aspect, the invention provides anti-CD27 antibodies that induce or enhance effector cell function (e.g., cell killing via either ADCC and/or CDC). In one embodiment, the antibody induces at least about 30% specific lysis of CD27 expressing cells via ADCC at an antibody concentration of 10 μg/ml and/or induces at least about 30% CDC of CD27 expressing cells at a concentration of 10 μg/ml. Particular antibodies falling within this class exhibiting ADCC effector function include, e.g., (e.g., mAb comprising heavy and/or light chain variable region sequences comprising SEQ ID NOs: 61 and/or 67 (mAb 1G5), SEQ ID NOs: 85 and/or 91, 85 and/or 97 (mAb 3A10), SEQ ID NOs:37 and/or 43 (mAb 1F5), SEQ ID NOs: 7 and/or 13, 7 and/or 19 (mAb 3H8), SEQ ID NOs: 49 and/or 55 (mAb 1H8), or SEQ ID NOs: 103 and/or 109 (mAb 3H12). In a further embodiment, the antibody also inhibits binding of CD70 to CD27 on cells. Particular antibodies having these combinations of functions include, e.g., (e.g., mAb comprising heavy and/or light chain variable regions sequences comprising SEQ ID NOs: 37 and/or 43 (mAb 1F5), SEQ ID NOs: 49 and/or 55 (mAb 1H8), SEQ ID NOs:103 and/or 109 (mAb 3H12). Alternatively, the antibody induces ADCC and/or CDC as described above, but does not inhibit binding of CD70 to CD27 on cells. Particular antibodies having these features include, e.g., mAb comprising heavy and/or light chain variable regions sequences comprising SEQ ID NOs: 61 and/or 67 (mAb 1G5), SEQ ID NOs: 85 and/or 91, 85 and/or 97 (mAb 3A10), SEQ ID NOs:7 and/or 13, 7 and/or 19 (mAb 3H8).

Anti-CD27 antibodies capable of inducing or enhancing effector cell function (e.g., ADCC and/or CDC) can also be constructed to include an Fc region which suitably contributes a binding specificity for a specific Fc receptor (e.g., FcγRI (CD64), FcγRIIA (CD32), FcγRIIB1 (CD32), FcγRIIB2 (CD32), FcγRIIIA (CD16a), FcγRIIIB (CD16b), FcεRI, FcεRII (CD23), FcαRI (CD89), Fcα/μR, and FcRn).

In a further embodiment there is provided a method for enhancing an immune response against an antigen in a subject in need thereof by administering to the subject: i) an anti-CD27 antibody and ii) an antigen, wherein the anti-CD27 antibody is administered separately from and before the antigen is administered.

Typically in such a method the anti-CD27 antibody may be administered between at least 2 and 96 hours before the antigen. For example, in such a method, the anti-CD27 antibody may be administered at least 2 hours before the antigen, for example at least 12 hours before the antigen, suitably at least 24 hours before the antigen, at least 48 hours before the antigen or at least 72 hours before the antigen.

wherein the TLR agonist is a TLR3 agonist.

In a further embodiment there is provided a method for enhancing an immune response against an antigen in a subject in need thereof by simultaneously, separately or sequentially administering to the subject: i) an anti-CD27 antibody; ii) a TLR agonist; and iii) optionally, the antigen.

In a preferred embodiment of such a method the TLR agonist is a TLR3 agonist, for example but not limited to Poly IC:LC.

CD27 expressing cells include any and all cells that express CD27, including, but not limited to B cells, NK cells and T cells. In a particular embodiment, the CD27 expressing cells include cancer cell lines such as Jurkat cells, Raji cells, Ramos cells and Daudi cells. In another embodiment, the CD27 expressing cells are tumor cells or cancer cells. In another embodiment, CD27 expressing cells include B cells, NK cells, and T cells including T cells that are found infiltrating tumors, also called tumor infiltrating lymphocytes.

Particular antibodies of the invention comprise heavy and light chain variable regions that utilize particular human germlines, i.e., are encoded by the germline genes, but include genetic rearrangements and mutations, e.g., somatic mutations, which occur during antibody maturation. In one embodiment, the heavy chain variable region of the antibodies of the present invention is derived from a human germline 3-7 or 3-33 gene. In another embodiment, the light chain variable region of the antibody is derived from a human germline 3-20, 3-11, 24, 1D-16, or 1-13 gene. In a particular embodiment, the heavy chain variable region of the antibody is derived from a human germline $V_H$3-7 or $V_H$3-33 gene and the light chain variable region of the antibody is derived from a human germline $V_K$3-20, $V_K$3-11, $V_K$1D-16, or $V_K$1-13 gene.

A $V_H$3-33 germline sequence is provided (Genbank Accession No AAP44382) as follows:

(SEQ ID NO: 3)

```
  1 vqlvesgggv vqpgrslrls caasgftfst ygmhwvrqap gkglewvaii wfdgsntyya
 61 dsvrgrftis rdssrktlyl emkslrvedt avyycak
```

A V$_H$3-7 germline sequence is provided (Genbank Accession No AAP44389) as follows:

```
                                                   (SEQ ID NO: 4)
  1 vqlvesgggl vqpggslrls caasgftfsn symtwvrqap gkglewvani kpdgsdknyi 61 nsvrgrftis rdnaekssyl qmnslraedt aiyycvt
```

In another embodiment, the heavy chain variable region CDR3 sequence is selected from the group consisting of SEQ ID NOs: 10, 28, 40, 52, 64, 76, 88, 106, and conservative sequence modifications thereof (e.g., conservative amino acid substitutions). The antibodies may further include a light chain variable region CDR3 sequence selected from the group consisting of SEQ ID NOs: 16, 22, 34, 46, 58, 70, 82, 94, 100, 112, and conservative sequence modifications thereof. In another embodiment, the heavy chain CDR2 and CDR1 sequences are selected from SEQ ID NOs: 9, 27, 39, 51, 63, 75, 87, 105, and SEQ ID NOs: 8, 26, 38, 50, 62, 74, 86, 104, respectively, and conservative sequence modifications thereof. The light chain CDR2 and CDR1 sequences are selected from SEQ ID NOs: 15, 21, 33, 45, 57, 69, 81, 93, 99, 111, and SEQ ID NOs: 14, 20, 32, 44, 56, 68, 80, 92, 98, 110, respectively, and conservative sequence modifications thereof.

In still another embodiment, the invention provides an isolated antibody that binds CD27 and includes heavy and light chain variable region CDR1, CDR2 and CDR3 sequences selected from the group consisting of:

(i) a heavy chain variable region CDR1 comprising SEQ ID NO: 38;
a heavy chain variable region CDR2 comprising SEQ ID NO: 39;
a heavy chain variable region CDR3 comprising SEQ ID NO: 40;
a light chain variable region CDR1 comprising SEQ ID NO: 44;
a light chain variable region CDR2 comprising SEQ ID NO: 45;
a light chain variable region CDR3 comprising SEQ ID NO: 46; or
conservative sequence modifications thereof;

(ii) a heavy chain variable region CDR1 comprising SEQ ID NO: 50;
a heavy chain variable region CDR2 comprising SEQ ID NO: 51;
a heavy chain variable region CDR3 comprising SEQ ID NO: 52;
a light chain variable region CDR1 comprising SEQ ID NO: 56;
a light chain variable region CDR2 comprising SEQ ID NO: 57;
a light chain variable region CDR3 comprising SEQ ID NO: 58; or
conservative sequence modifications thereof;

(iii) a heavy chain variable region CDR1 comprising SEQ ID NO: 104;
a heavy chain variable region CDR2 comprising SEQ ID NO: 105;
a heavy chain variable region CDR3 comprising SEQ ID NO: 106;
a light chain variable region CDR1 comprising SEQ ID NO: 110;
a light chain variable region CDR2 comprising SEQ ID NO: 111;
a light chain variable region CDR3 comprising SEQ ID NO: 112; or
conservative sequence modifications thereof;

(iv) a heavy chain variable region CDR1 comprising SEQ ID NO: 86;
a heavy chain variable region CDR2 comprising SEQ ID NO: 87;
a heavy chain variable region CDR3 comprising SEQ ID NO: 88;
a light chain variable region CDR1 comprising SEQ ID NO: 92 or 98;
a light chain variable region CDR2 comprising SEQ ID NO: 93 or 99;
a light chain variable region CDR3 comprising SEQ ID NO: 94 or 100;
or conservative sequence modifications thereof;

(v) a heavy chain variable region CDR1 comprising SEQ ID NO: 26;
a heavy chain variable region CDR2 comprising SEQ ID NO: 27;
a heavy chain variable region CDR3 comprising SEQ ID NO: 28;
a light chain variable region CDR1 comprising SEQ ID NO: 32;
a light chain variable region CDR2 comprising SEQ ID NO: 33;
a light chain variable region CDR3 comprising SEQ ID NO: 34; or
conservative sequence modifications thereof;

(vi) a heavy chain variable region CDR1 comprising SEQ ID NO: 74;
a heavy chain variable region CDR2 comprising SEQ ID NO: 75;
a heavy chain variable region CDR3 comprising SEQ ID NO: 76;
a light chain variable region CDR1 comprising SEQ ID NO: 80;
a light chain variable region CDR2 comprising SEQ ID NO: 81;
a light chain variable region CDR3 comprising SEQ ID NO: 82; or
conservative sequence modifications thereof;

(vii) a heavy chain variable region CDR1 comprising SEQ ID NO: 8;
a heavy chain variable region CDR2 comprising SEQ ID NO: 9;
a heavy chain variable region CDR3 comprising SEQ ID NO: 10;
a light chain variable region CDR1 comprising SEQ ID NO: 14 or 20;
a light chain variable region CDR2 comprising SEQ ID NO: 15 or 21;
a light chain variable region CDR3 comprising SEQ ID NO: 16 or 22;
or conservative sequence modifications thereof; and (viii) a heavy chain variable region CDR1 comprising SEQ ID NO: 62;

a heavy chain variable region CDR2 comprising SEQ ID NO: 63;
a heavy chain variable region CDR3 comprising SEQ ID NO: 64;
a light chain variable region CDR1 comprising SEQ ID NO: 68;
a light chain variable region CDR2 comprising SEQ ID NO: 69;
a light chain variable region CDR3 comprising SEQ ID NO: 70; or
conservative sequence modifications thereof.

In another embodiment, the heavy chain variable region CDR3 sequence comprises an amino acid sequence selected from the consensus sequence: R (G,E,D) (S,L,G,-) (G,L,T,W,-) (N,A,T,H,-) (V,T,-) (M,P,-) (G,V,-) (R, -) (G,M, -) (D,H,L,T,W) (A,G,N,W) (D,F,V,Y) (F,L) (D,E) (H,I,L,Y) (SEQ ID NO: 113), wherein "-" denotes the option of no amino acid residue being present at that consensus position. The antibodies may further include a light chain variable region CDR3 sequence comprising an amino acid sequence selected from the consensus sequence: Q (F,R,Y) (N,S) (N,T,S) (Y,W) P (F,L,P,R) T (SEQ ID NO: 114), wherein "-" denotes the option of no amino acid residue being present at that consensus position. In another embodiment, the heavy chain variable region CDR2 sequence comprises an amino acid sequence selected from the consensus sequence: I (K,W) (Y,N,Q) D G S (E,N) (K,Q) (SEQ ID NO: 115), wherein "-" denotes the option of no amino acid residue being present at that consensus position, and the light chain variable region CDR2 sequence comprises an amino acid sequence selected from the consensus sequence: (A,D) A S (SEQ ID NO: 116). In another embodiment, the heavy chain variable region CDR1 sequence comprises an amino acid sequence selected from the consensus sequence: G F (T,S) (F,L) (S,N) (I,S,H) (Y,H) (SEQ ID NO: 117); and the light chain variable region CDR1 sequence comprises an amino acid sequence selected from the consensus sequence: Q (D,G,S) (I,V) (D,S) (R,S) (A,W,Y) (SEQ ID NO: 118).

In another embodiment, isolated antibodies of the invention bind to human CD27 and include a heavy chain variable region including an amino acid sequence selected from the group consisting of SEQ ID NOs: 6, 7, 24, 25, 36, 37, 48, 49, 60, 61, 72, 73, 84, 85, 102, 103, and conservative sequence modifications thereof. The antibody may further include a light chain variable region including an amino acid sequence selected from the group consisting of SEQ ID NOs: 12, 13, 18, 19, 30, 31, 42, 43, 54, 55, 66, 67, 78, 79, 90, 91, 96, 97, 108, 109, and conservative sequence modifications thereof.

In a still further embodiment, isolated antibodies of the invention bind to human CD27 and include a heavy chain variable region and a light chain variable region including the amino acid sequences selected from the group consisting of:
(a) SEQ ID NOs: 37 and/or 43, respectively, and conservative sequence modifications thereof;
(b) SEQ ID NOs: 49 and/or 55, respectively, and conservative sequence modifications thereof;
(c) SEQ ID NOs: 103 and/or 109, respectively, and conservative sequence modifications thereof;
(d) SEQ ID NOs: 85 and/or 91 and/or 97, respectively, and conservative sequence modifications thereof;
(e) SEQ ID NOs: 25 and/or 31, respectively, and conservative sequence modifications thereof;
(f) SEQ ID NOs: 73 and/or 79, respectively, and conservative sequence modifications thereof;
(g) SEQ ID NOs: 7 and/or 13 and/or 19, respectively, and conservative sequence modifications thereof; and
(h) SEQ ID NOs: 61 and/or 67, respectively, and conservative sequence modifications thereof;

Isolated antibodies which include heavy and light chain variable regions having at least 80%, or at least 85%, or at least 90%, or at least 95%, or at least 96%, or at least 97%, or at least 98%, or at least 99%, or more sequence identity to any of the above sequences are also included in the present invention. Ranges intermediate to the above-recited values, e.g., heavy and light chain variable regions having at least 80-85%, 85-90%, 90-95% or 95-100% sequence identity to any of the above sequences are also intended to be encompassed by the present invention.

Also encompassed by the present invention are isolated antibodies which compete for binding to CD27 with the antibodies of the invention. In a particular embodiment, the antibody competes for binding to CD27 with an antibody comprising heavy and/or light chain variable regions comprising the amino acid sequences set forth in SEQ ID NOs: 37 and 43, SEQ ID NOs: 49 and 55, SEQ ID NOs: 103 and 109, SEQ ID NOs: 85 and 91, SEQ ID NOs: 85 and 97, SEQ ID NOs: 25 and 31, SEQ ID NOs: 73 and 79, SEQ ID NOs: 7 and 13, SEQ ID NOs: 7 and 19, SEQ ID NOs: 61 an 67, respectively, or amino acid sequences at least 80% identical thereto. In another embodiment, the antibody competes for binding to CD27 with an antibody comprising heavy and/or light chain variable regions comprising the amino acid sequences set forth in SEQ ID NOs: 37 and 43 (1F5), SEQ ID NOs: 49 and 55 (1H8) or SEQ ID NOs: 103 and 109 (3H12). In another embodiment, the antibody competes for binding to CD27 with an antibody comprising heavy and/or light chain variable regions comprising the amino acid sequences set forth in SEQ ID NOs: 25 and 31 (2C2), SEQ ID NOs: 7 and 13 (3H8), SEQ ID NOs: 7 and 19 (3H8), SEQ ID NOs: 61 an 67 (1G5) or SEQ ID NOs: 73 and 79 (2G9). In yet another embodiment, the antibody competes for binding to CD27 with an antibody comprising heavy and/or light chain variable regions comprising the amino acid sequences set forth in SEQ ID NOs: 85 and 91 (3A10) or SEQ ID NOs: 85 and 97 (3A10).

Other antibodies of the invention bind to an epitope on CD27 recognized by the antibodies described herein. In another particular embodiment, the antibody binds to an epitope on CD27 recognized by an antibody comprising heavy and/or light chain variable regions comprising the amino acid sequences set forth in SEQ ID NOs: 37 and 43, SEQ ID NOs: 49 and 55, SEQ ID NOs: 103 and 109, SEQ ID NOs: 85 and 91, SEQ ID NOs: 85 and 97, SEQ ID NOs: 25 and 31, SEQ ID NOs: 73 and 79, SEQ ID NOs: 7 and 13, SEQ ID NOs: 7 and 19, SEQ ID NOs: 61 an 67, respectively, or amino acid sequences at least 80% identical thereto. In another embodiment, the antibody binds to an epitope on CD27 recognized by an antibody comprising heavy and/or light chain variable regions comprising the amino acid sequences set forth in SEQ ID NOs: 37 and 43 (1F5), SEQ ID NOs: 49 and 55 (1H8) or SEQ ID NOs: 103 and 109 (3H12). In another embodiment, the antibody binds to an epitope on CD27 recognized by an antibody comprising heavy and/or light chain variable regions comprising the amino acid sequences set forth in SEQ ID NOs: 25 and 31 (2C2), SEQ ID NOs: 7 and 13 (3H8), SEQ ID NOs: 7 and 19 (3H8), SEQ ID NOs: 61 an 67 (1G5) or SEQ ID NOs: 73 and 79 (2G9). In yet another embodiment, the antibody binds to an epitope on CD27 recognized by an antibody comprising heavy and/or light chain variable regions comprising the amino acid sequences set forth in SEQ ID NOs: 85 and 91 (3A10) or SEQ ID NOs: 85 and 97 (3A10).

The antibodies of the invention can either be full-length, for example, any of the following isotypes: IgG1, IgG2, IgG3, IgG4, IgM, IgA1, IgA2, IgAsec, IgD, and IgE. Alternatively, the antibodies can be fragments such as an antigen-binding portion or a single chain antibody (e.g., a Fab, F(ab')$_2$, Fv, a single chain Fv fragment, an isolated complementarity determining region (CDR) or a combination of two or more isolated CDRs). The antibodies can be any kind of antibody, including, but not limited to, human, humanized, and chimeric antibodies.

Tumor antigens employed by the present invention (e.g., in a vaccine, used in combination with an anti-CD27 antibody of the invention) include any antigen or antigenic determinant which is present on (or associated with) a tumor cell and not typically on normal cells, or an antigen or antigenic determinant which is present on or associated with tumor cells in greater amounts than on normal (non-tumor) cells, or an antigen or antigenic determinant which is present on tumor cells in a different form than that found on normal (non-tumor) cells. Such antigens include tumor-specific antigens, including tumor-specific membrane antigens, tumor-associated antigens, including tumor-associated membrane antigens, embryonic antigens on tumors, growth factor receptors, growth factor ligands, and any other type of antigen that is associated with cancer. A tumor antigen may be, for example, an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen. For example, the antigen may include a tumor antigen, such as βhCG, gp100 or Pmel17, CEA, gp100, TRP-2, NY-BR-1, NY-CO-58, MN (gp250), idiotype, Tyrosinase, Telomerase, SSX2, MUC-1, MAGE-A3, and high molecular weight-melanoma associated antigen (HMW-MAA) MART1, melan-A, EGFRvIII, NY-ESO-1, MAGE-1, MAGE-3, WT1, Her2, or mesothelin. Other antigens employed by the present invention (e.g., in a vaccine, used in combination with an anti-CD27 antibody of the invention) include antigens from infectious disease pathogens, such as viruses, bacteria, parasites and fungi, examples of which are disclosed herein.

The invention also provides a bispecific molecule comprising an antibody of the invention linked to a second functional moiety having a different binding specificity than said antibody. For example, in one embodiment, the second molecule may bind a T cell receptor (e.g., CD3, CD40).

Compositions including an antibody or a bispecific molecule described herein, formulated with a pharmaceutically acceptable carrier, are also provided. The compositions may further include an adjuvant, immunostimulatory agent (e.g., CD40 ligand, FLT 3 ligand, cytokines, colony-stimulating factors, an anti-CTLA-4 antibody, anti-PD1 antibody, anti-41BB antibody, anti OX-40 antibody, LPS (endotoxin), ssRNA, dsRNA, Bacille Calmette-Guerin (BCG), Levamisole hydrochloride, intravenous immune globulins and a Toll-like Receptor (TLR) agonist (e.g., TLR3 agonist such as Poly IC, a TLR4 agonist, a TLR5 agonist, a TLR7 agonist, a TLR8 agonist, and a TLR 9 agonist)), immunosuppressive agent, another antibody, or an antigen. Exemplary antigens include, but are not limited to, a component of a pathogen, a tumor antigen (e.g., βhCG, gp100 or Pmel17, HER2/neu, WT1, mesothelin, CEA, gp100, MART1, TRP-2, melan-A, NY-ESO-1, NY-BR-1, NY-CO-58, MN (gp250), idiotype, MAGE-1, MAGE-3, MAGE-A3, Tyrosinase, Telomerase, SSX2 antigens, MUC-1 antigens, and germ cell derived tumor antigens), an infectious disease antigen (e.g. viral antigens, bacterial and parasitic antigens) an allergen, or an autoantigen. Any of the antigens disclosed herein can be included in a composition of the invention.

Nucleic acid molecules encoding the antibodies of the invention are also encompassed by the invention, as well as expression vectors comprising such nucleic acids and host cells comprising such expression vectors. For example, in one embodiment, the invention provides an isolated monoclonal antibody that binds human CD27, wherein the antibody comprises a heavy chain variable region and a light chain variable region encoded by nucleic acid sequences selected from the group consisting of: (a) SEQ ID NOs: 5 and 11, respectively; (b) SEQ ID NOs: 5 and 17, respectively; (c) SEQ ID NOs: 23 and 29, respectively; (d) SEQ ID NOs: 35 and 41, respectively; (e) SEQ ID NOs: 47 and 53, respectively; (f) SEQ ID NOs: 59 and 65, respectively; (g) SEQ ID NOs: 71 and 77, respectively; (h) SEQ ID NOs: 83 and 89, (i) SEQ ID NOs: 83 and 95; (j) SEQ ID NOs: 101 and 107, respectively or nucleic acid sequences having at least 90% identity to the nucleic acid sequences of (a)-(h).

In another embodiment, the present invention provides methods for inducing or enhancing an immune response (e.g., a T cell-mediated immune response, and/or an NK-mediated response and/or a B cell-mediated immune response) against an antigen in a subject by administering to the subject an effective amount of an antibody (e.g., a full length antibody), composition or bispecific molecule described herein. Such methods are particularly well-suited for use in vaccine therapies.

The antibodies and other compositions of the present invention can also be used to inhibit growth of CD27 expressing cells by contacting the cells with an antibody or composition in an amount effective to inhibit growth of CD27 expressing cells (e.g., in the treatment of cancers). Antibodies useful in inhibiting the growth of CD27 expressing cells include full length antibodies and fragments thereof, as well as antibodies that contain a second binding specificity for an Fc receptor. In one embodiment, the CD27 expressing cells are contacted with an antibody in the presence of effector cells under conditions sufficient to induce antibody-dependent cellular cytotoxicity (ADCC) of target cells (e.g., the antibody induces at least about 40% specific lysis of CD27 expressing cells at a concentration of 10 μg/ml and comprises SEQ ID NOs:61, 67, 85, 91, 97, 37, and/or 43). In another embodiment, the cells are contacted with an antibody under conditions sufficient to induce complement mediated cytotoxicity (CDC) of the cells (e.g., the antibody induces at least about 40% complement mediated cytotoxicity (CDC) of CD27 expressing cells at a concentration of 10 μg/ml and comprises SEQ ID NOs: 7, 13, 19, 49, 55, 103, and/or 109).

In a further embodiment, the antibody employed to inhibit growth of CD27 expressing cells may also possess (or lack) additional functional features. For example, the antibody may also inhibit the binding of CD70 to CD27 on cells which express these proteins (e.g., a mAb comprising heavy and/or light chain variable regions sequences comprising SEQ ID NOs: 37 and/or 43 (mAb 1F5), SEQ ID NOs: 49 and/or 55 (mAb 1H8), or SEQ ID NOs: 103 and/or 109 (mAb 3H12). Alternatively, the antibody may not inhibit the binding of CD70 to CD27 on such cells (e.g., a mAb comprising heavy and/or light chain variable regions sequences comprising SEQ ID NOs: 61 and/or 67 (mAb 1G5), SEQ ID NOs: 85 and/or 91, 85 and/or 97 (mAb 3A10), or SEQ ID NOs:7 and/or 13, 7 and/or 19 (mAb 3H8).

CD27 expressing cells include any and all cells the express CD27, including, but not limited to NK cells, B cells and T cells. In a particular embodiment, the CD27 expressing cells include cell lines such as Jurkat cells, Raji cells, Ramos cells and Daudi cells. In another embodiment, the CD27 expressing cells are tumor cells or cancer cells. In another embodiment, CD27 expressing cells include B cells, NK cells, T cells that are found infiltrating tumor or cancer cells, also called tumor infiltrating lymphocytes.

The methods of inhibiting the growth of CD27 expressing cells that are described herein can be used to treat and prevent a wide variety of diseases and disorders. For example, in one embodiment, the methods can be used to treat or prevent a cancer (e.g., a cancer selected from the group consisting of leukemia, acute lymphocytic leukemia, acute myelocytic leukemia, myeloblasts promyelocyte myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma, marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system). Preferred cancers include CD27-expressing tumors selected from the group consisting of chronic lymphocytic leukemia, mantle cell lymphoma, primary central nervous system lymphoma, Burkitt's lymphoma and marginal zone B cell lymphoma. In another embodiment, the methods can be used to treat or prevent a bacterial, fungal, viral or parasitic infection.

The present invention further provides methods for inhibiting the binding of CD70 to CD27 on cells in a subject having a disorder by administering to the subject antibodies or compositions as described herein, as well as methods for down-regulating a T cell response in an individual having a disorder by administering to a subject antibodies or compositions described herein. These methods are ideally suited for use in the treatment of immune disorders, such as graft rejection, autoimmune diseases, and allergy. Antibodies useful in these methods include Fab fragments, as well as a mutated Fc region so that the antibody does not bind, or has significantly reduced binding to, Fc receptors. In a particular embodiment, the antibody comprises heavy and/or light chain variable regions sequences comprising SEQ ID NOs: 37 and/or 43 (mAb 1F5), SEQ ID NOs: 49 and/or 55 (mAb 1H8), or SEQ ID NOs: 103 and/or 109 (mAb 3H12).

The methods described herein for inhibiting the binding of CD70 to CD27 on cells and for down-regulating a T cell response can be used to treat a wide variety of diseases and disorders, including, but not limited to graft rejection, allergy and autoimmune diseases. In a particular embodiment, the disease is an autoimmune disease (e.g., multiple sclerosis, rheumatoid arthritis, type 1 diabetes, psoriasis, Crohn's disease and other inflammatory bowel diseases such as ulcerative colitis, systemic lupus eythematosus (SLE), autoimmune encephalomyelitis, myasthenia gravis (MG), Hashimoto's thyroiditis, Goodpasture's syndrome, pemphigus, Graves disease, autoimmune hemolytic anemia, autoimmune thrombocytopenic purpura, scleroderma with anti-collagen antibodies, mixed connective tissue disease, polypyositis, pernicious anemia, idiopathic Addison's disease, autoimmune associated infertility, glomerulonephritis, crescentic glomerulonephritis, proliferative glomerulonephritis, bullous pemphigoid, Sjogren's syndrome, psoriatic arthritis, insulin resistance, autoimmune diabetes mellitus, autoimmune hepatitis, autoimmune hemophilia, autoimmune lymphoproliferative syndrome (ALPS), autoimmune hepatitis, autoimmune hemophilia, autoimmune lymphoproliferative syndrome, autoimmune uveoretinitis, Guillain-Bare syndrome, arteriosclerosis and Alzheimer's disease).

The present invention further provides for particular uses for the antibodies, compositions and bispecific molecules described herein. For example, in one embodiment, the invention provides for the use of an antibody, composition or bispecific molecule in the manufacture of a medicament for inducing or enhancing an immune response against an antigen in a subject. In further embodiments, the invention provides for the use of an antibody or composition in the manufacture of a medicament for inhibiting growth of CD27 expressing cells, the use of an antibody or composition in the manufacture of a medicament for inhibiting the binding of CD70 to CD27 on cells in a subject having a disorder, and the use of an antibody or composition in the manufacture of a medicament for down-regulating a T cell response in an individual having a disorder. The present invention further includes an antibody, composition or bispecific molecule for use in inducing or enhancing an immune response against an antigen in a subject, an antibody or composition for use in inhibiting growth of CD27 expressing cells, an antibody or composition for use in inhibiting the binding of CD70 to CD27 on cells in a subject having a disorder, and an antibody or composition for use in down-regulating a T cell response in an individual having a disorder.

The present invention also provides methods for detecting the presence or absence of CD27 in a biological sample by (1) contacting a biological sample with an antibody described herein (wherein the antibody is labeled with a detectable substance) and (2) detecting the antibody bound to CD27.

Also within the scope of the invention are kits comprising the compositions (e.g., antibodies and/or bispecific molecules) of the invention and, optionally, instructions for use. The kit can further contain a least one additional reagent, such as a cytokine or complement, or one or more additional antibodies of the invention.

Other features and advantages of the instant invention will be apparent from the following detailed description and claims.

BRIEF DESCRIPTION OF THE DRAWINGS

FIG. 1 depicts the affinity and kinetic parameters for mAbs 1G5, 1H8, 3H12, 3H8, 2G9, 1F5, 3A10, 2C2, ms 1A4, ms 9F4 and ms M-T271 as determined by Biacore™ BiaEvaluation software (Biacore AB) with recombinant human CD27 immobilized on the chip.

FIG. 15 is an alignment of the VH sequences of human anti-CD27 antibodies (1F5 (SEQ ID NO: 36), 1G5 (SEQ ID NO: 60), 1H8 (SEQ ID NO: 48), 2C2 (SEQ ID NO: 1.l, 2G9 (SEQ ID NO: 72), 3A10 (SEQ ID NO: 84), 3H12 (SEQ ID NO: 102) and 3H8 (SEQ ID NO: 6)).

FIG. 16 is an alignment of the VL sequences of human anti-CD27 antibodies (1F5 (SEQ ID NO: 42), 1G5 (SEQ ID NO: 66), 1H8 (SEQ ID NO: 54), 2C2 (SEQ ID NO: al, 2G9 (SEQ ID NO: 30), 3A10 (SEQ ID NO: 120), 3H12 (SEQ ID NO: 108) and 3H8 (SEQ ID NO: 12)).

FIG. 17 shows 1F5 on circulating lymphocytes after a single dose.

FIG. 18 shows 1F5 does not significantly deplete circulating lymphocytes.

FIG. 19 discloses SEQ ID NO: 119.

FIG. 20 discloses SEQ ID NO: 119.

FIG. 22A shows the protocol for the experiment. FIG. 22B shows the results of a tetramer staining experiment to measure antigen-specific T cells. FIG. 22C shows the results of an IFN-gamma ELISPOT assay to measure antigen-specific T cells.

FIGS. 23A-D are the results of an experiment showing that anti-CD27 in combination with the TLR3 agonist PolyIC (at 25 μg, 50 μg or 100 μg) enhances T cell responses to an APC-targeted vaccine (α-DEC205-OVA). FIG. 23A is a graph showing the % of IFN-gamma positive cells among CD8+ T cells for either wild-type mice treated with poly IC and the anti-CD27 mAb 1F5, huCD27-transgenic mice treated with poly IC and a control human IgG1 antibody or huCD27-transgenic mice treated with poly IC and the anti-CD27 mAb 1F5.

FIG. 24A shows the protocol for the experiment. FIG. 24B is a graph plotting the tumor size (in mm$^2$) against number of days post tumor inoculation in untreated mice. FIG. 24C is a graph plotting the tumor size (in mm$^2$) against number of days post tumor inoculation in mice treated with the vaccine alone. FIG. 24D is a graph plotting the tumor size (in mm$^2$) against number of days post tumor inoculation in mice treated with the vaccine in combination with an anti-CD27 antibody.

FIGS. 29A and B are graphs showing prolonged survival of human CD27-transgenic mice (tumor models) following challenge with a syngeneic lymphoma and administration of various doses of anti-CD27 mAb 1F5.

FIGS. 30 to 32 show the results of an experiment testing the effect of anti-CD27 treatment in a Raji xenograft model in SCID mice.

FIG. 30A plots the tumor size (in mm³) against number of days post tumor inoculation in mice either untreated, treated with a control human IgG1 antibody or treated with the anti-CD27 1F5 and 3H8 antibodies. Arrows indicate days when antibody treatment was given by i.p. injection.

FIG. 30B shows survival in a Kaplan-Meier plot.

FIG. 31A plots the tumor size (in mm³) against number of days post tumor inoculation in mice either untreated, treated with a control human IgG1 antibody or treated with the anti-CD27 1F5 antibody. Arrows indicate days when antibody treatment was given by i.p. injection. FIG. 31B shows survival in a Kaplan-Meier plot.

FIG. 32 shows the results of a further experiment testing the effect of anti-CD27 treatment in a Raji xenograft model in SCID mice in a Kaplan-Meier plot.

FIG. 33 shows the results of an experiment testing the effect of anti-CD27 treatment in a Daudi xenograft model in SCID mice. FIG. 33A plots the tumor size (in mm³) against number of days post tumor inoculation in mice either treated with a control human IgG1 antibody or treated with the anti-CD27 1F5 antibody (0.1 mg or 0.3 mg). Arrows indicate days when antibody treatment was given by i.p. injection. FIG. 33B shows survival in a Kaplan-Meier plot.

DETAILED DESCRIPTION OF THE INVENTION

Figure 2:
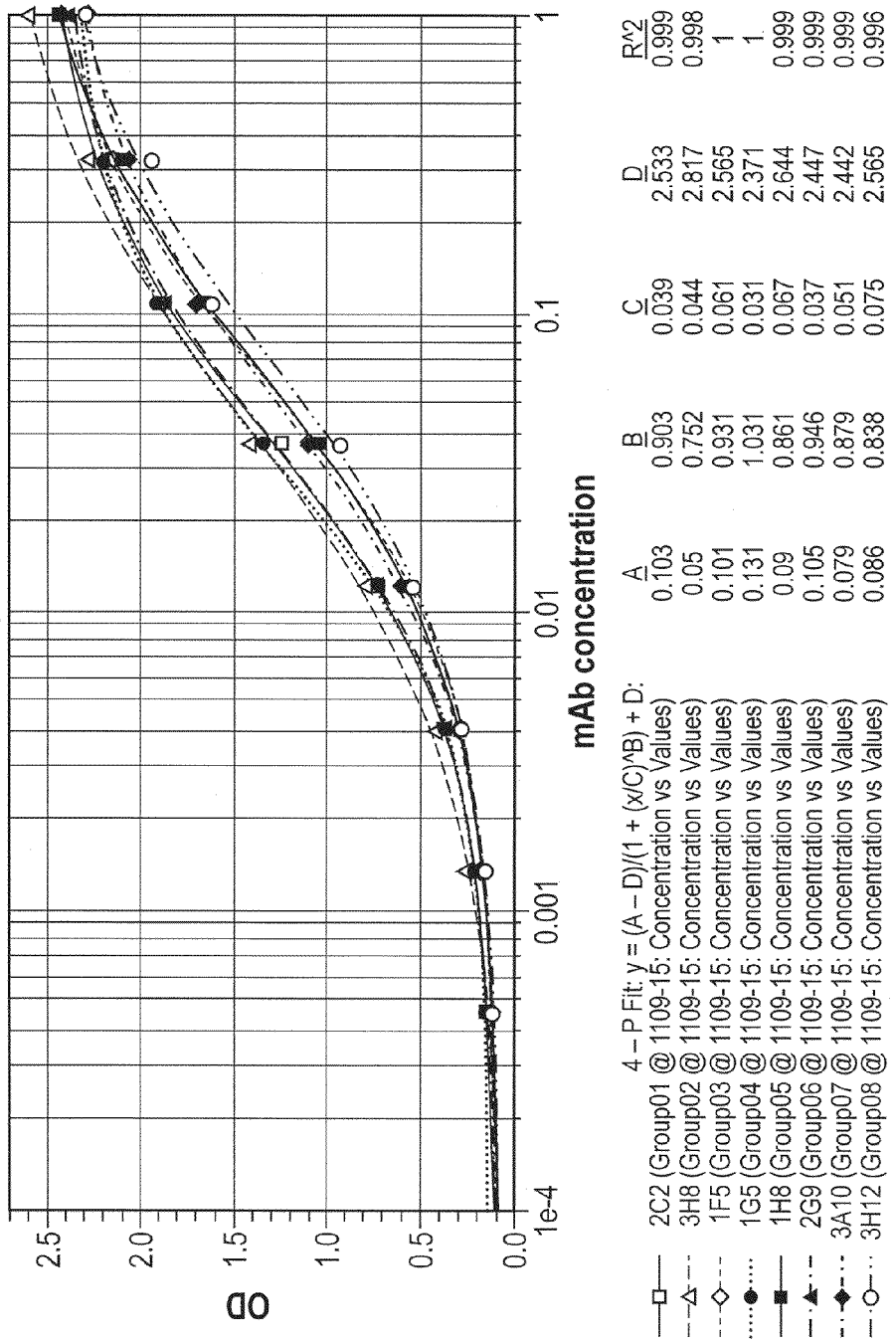
FIG. 2 is a graph showing the binding of human anti-CD27 antibodies (2C2, 3H8, 1F5, 1G5, 1H8, 2G9, 3A10 and 3H12) to recombinant purified human CD27 using ELISA.

The present invention provides anti-CD27 antibodies that exhibit particular functional properties correlating with significant therapeutic benefits, including upregulation of immune function (e.g. T cell mediated immune responses as in vaccine therapies, NK activation in cancer therapies), inhibition of cell growth (e.g., in cancer therapy) and down-regulation of T cell mediated immune responses (e.g., in autoimmune therapy). These functional features include, for example: (1) inhibition of (e.g., completely or partially blocks) binding of soluble CD70 to CD27 expressing cells by at least about 70%, further for example by at least 80% or at least 90% (2) binding to human CD27 with a $K_D$ of $1\times10^{-9}$ M or less, (3) induction of at least about 40% complement mediated cytotoxicity (CDC) of CD27 expressing cells at a concentration of 10 µg/ml, (4) induction of at least about 40% specific lysis of CD27 expressing cells by ADCC at a concentration of 10 µg/ml, (further for example at least about 50%, at least about 60% or at least about 70% specific lysis) (5) induction or enhancement of immune responses, especially TH1 responses and/or (6) induction or enhancement of T-cell activity, especially specific CD8+ T-cell numbers and/ or activity. In other embodiments, the antibodies include particular heavy and light chain variable regions and/or CDR sequences.

In order that the present invention may be more readily understood, certain terms are first defined. Additional definitions are set forth throughout the detailed description.

The term "CD27" (also referred to as "CD27 molecule", "CD27L receptor", "S1521", "T cell activation antigen CD27", "TNFRSF7," "MGC20393," "tumor necrosis factor receptor superfamily, member 7", "T cell activation antigen S152" "Tp55", "Tumor necrosis factor receptor superfamily member 7", "CD27 antigen", and "T-cell activation antigen CD27") refers to a receptor that is a member of the TNF-receptor superfamily, which binds to ligand CD70. CD27 is required for generation and long-term maintenance of T cell immunity and plays a key role in regulating B-cell activation and immunoglobulin synthesis. The term "CD27" includes any variants or isoforms of CD27 which are naturally expressed by cells (e.g., human CD27 deposited with GEN-BANK® having accession no. AAH12160.1). Accordingly, antibodies of the invention may cross-react with CD27 from species other than human. Alternatively, the antibodies may be specific for human CD27 and may not exhibit any cross-reactivity with other species. CD27 or any variants and isoforms thereof, may either be isolated from cells or tissues which naturally express them or be recombinantly produced using well-known techniques in the art and/or those described herein. Preferably the antibodies are targeted to hCD27 which has a normal glycosylation pattern.

Genbank® (Accession No. AAH12160.1) reports the amino acid sequence of human CD27 as follows (SEQ ID NO:1):

```
  1 marphpwwlc vlgtlvglsa tpapkscper hywaqgklcc qmcepgtflv kdcdqhrkaa
 61 qcdpcipgvs fspdhhtrph cescrhcnsg llvrnctita naecacrngw qcrdkectec
121 dplpnpslta rssqalsphp qpthlpyvse mleartaghm qtladfrqlp artlsthwpp
181 qrslcssdfi rilvifsgmf lvftlagalf lhqrrkyrsn kgespvepae pcryscpree
241 egstipiqed yrkpepacsp
```

The term "CD70" (also referred to as "CD70 molecule", "CD27L", "CD27LG", "TNFSF7," "tumor necrosis factor (ligand) superfamily member 7," "CD27 ligand," "CD70 antigen," "surface antigen CD70," "tumor necrosis factor ligand superfamily, member 7," "Ki-24 antigen," and "CD27-L") refers to the ligand for CD27 (see, for example, Bowman M R et al., *J. Immunol.* 1994 Feb. 15; 152(4):1756-61). CD70 is a type II transmembrane protein that belongs to the tumor necrosis factor (TNF) ligand family. It is a surface antigen on activated T and B lymphocytes that induces proliferation of co-stimulated T cells, enhances the generation of cytolytic T cells, and contributes to T cell activation. It has also been suggested that CD70 plays a role in regulating B-cell activation, cytotoxic function of natural killer cells, and immunoglobulin synthesis (Hintzen R Q et al., *J. Immunol.* 1994 Feb. 15; 152(4):1762-73).

Genbank® (Accession No. NP_001243) reports the amino acid sequence of human CD70 as follows (SEQ ID NO: 2):

```
  1 mpeegsgcsv rrrpygcvlr aalvplvagl viclvvciqr faqaqqqlpl eslgwdvael 61 qlnhtgpqqd prlywqggpa lgrsflhgpe ldkgqlrihr dgiymvhiqv tlaicsstta 121 srhhpttlav gicspasrsi sllrlsfhqg ctiasqrltp largdtlctn ltgtllpsrn 181 tdetffgvqw vrp
```

The term "antibody" as referred to herein includes whole antibodies and any antigen binding fragment (i.e., "antigen-binding portion") or single chain thereof. An "antibody" refers, in one preferred embodiment, to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., human CD27). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992).

The term "monoclonal antibody," as used herein, refers to an antibody which displays a single binding specificity and affinity for a particular epitope. Accordingly, the term "human monoclonal antibody" refers to an antibody which displays a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

The term "human antibody" includes antibodies having variable and constant regions (if present) of human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo) (see, Lonberg, N. et al. (1994) *Nature* 368(6474): 856-859); Lonberg, N. (1994) *Handbook of Experimental Pharmacology* 113:49-101; Lonberg, N. and Huszar, D. (1995) *Intern. Rev. Immunol. Vol.* 13: 65-93, and Harding, F. and Lonberg, N. (1995) *Ann. N.Y. Acad. Sci.* 764:536-546). However, the term "human antibody" does not include antibodies in which CDR sequences derived from the germline of another mammalian species, such as a mouse, have been grafted onto human framework sequences (i.e., humanized antibodies).

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

An "isolated antibody," as used herein, is intended to refer to an antibody which is substantially free of other antibodies having different antigenic specificities (e.g., an isolated antibody that specifically binds to human CD27 is substantially free of antibodies that specifically bind antigens other than human CD27). An isolated antibody that specifically binds to an epitope of may, however, have cross-reactivity to other CD27 proteins from different species. However, the antibody preferably always binds to human CD27. In addition, an isolated antibody is typically substantially free of other cellular material and/or chemicals. In one embodiment of the invention, a combination of "isolated" antibodies having different CD27 specificities is combined in a well defined composition.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from CD27 are tested for reactivity with the given anti-CD27 antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

Also, encompassed by the present invention are antibodies that bind to an epitope on CD27 which comprises all or a portion of an epitope recognized by the particular antibodies described herein (e.g., the same or an overlapping region or a region between or spanning the region).

Also encompassed by the present invention are antibodies that bind the same epitope and/or antibodies that compete for binding to human CD27 with the antibodies described herein. Antibodies that recognize the same epitope or compete for binding can be identified using routine techniques. Such techniques include, for example, an immunoassay, which shows the ability of one antibody to block the binding of another antibody to a target antigen, i.e., a competitive binding assay. Competitive binding is determined in an assay in which the immunoglobulin under test inhibits specific binding of a reference antibody to a common antigen, such as CD27. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

Other techniques include, for example, epitope mapping methods, such as, x-ray analyses of crystals of antigen:antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

As used herein, the terms "specific binding," "selective binding," "selectively binds," and "specifically binds," refer to antibody binding to an epitope on a predetermined antigen. Typically, the antibody binds with an equilibrium dissociation constant ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 2000 instrument using recombinant human CD27 as the analyte and the antibody as the ligand and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

The term "$K_D$," as used herein, is intended to refer to the dissociation equilibrium constant of a particular antibody-antigen interaction. Typically, the human antibodies of the invention bind to CD27 with a dissociation equilibrium constant ($K_D$) of approximately $10^{-8}$ M or less, such as less than $10^{-9}$ M or $10^{-10}$ M or even lower when determined by surface plasmon resonance (SPR) technology in a BIACORE 2000 instrument using recombinant human CD27 as the analyte and the antibody as the ligand.

The term "kd" as used herein, is intended to refer to the off rate constant for the dissociation of an antibody from the antibody/antigen complex.

The term "ka" as used herein, is intended to refer to the on rate constant for the association of an antibody with the antigen.

The term "EC50," as used herein, refers to the concentration of an antibody or an antigen-binding portion thereof, which induces a response, either in an in vitro or an in vivo assay, which is 50% of the maximal response, i.e., halfway between the maximal response and the baseline.

As used herein, "isotype" refers to the antibody class (e.g., IgM or IgG1) that is encoded by heavy chain constant region genes. In one embodiment, a human monoclonal antibody of the invention is of the IgG1 isotype. In another embodiment, a human monoclonal antibody of the invention is of the IgG2 isotype.

The term "binds to immobilized CD27," refers to the ability of a human antibody of the invention to bind to CD27, for example, expressed on the surface of a cell or which is attached to a solid support.

The term "cross-reacts," as used herein, refers to the ability of an antibody of the invention to bind to CD27 from a different species. For example, an antibody of the present invention which binds human CD27 may also bind another species of CD27. As used herein, cross-reactivity is measured by detecting a specific reactivity with purified antigen in binding assays (e.g., SPR, ELISA) or binding to, or otherwise functionally interacting with, cells physiologically expressing CD27. Methods for determining cross-reactivity include standard binding assays as described herein, for example, by Biacore surface plasmon resonance (SPR) analysis using a Biacore 2000 SPR instrument (Biacore AB, Uppsala, Sweden), or flow cytometric techniques.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ (δ-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a μ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody portions (e.g., $V_H$, $V_L$, CDR3) that bind to CD27, is intended to refer to a nucleic acid molecule in which the nucleotide sequences encoding the antibody or antibody portion are free of other nucleotide sequences encoding antibodies or antibody portions that bind antigens other than CD27, which other sequences may naturally flank the nucleic acid in human genomic DNA. For example, SEQ ID NOs: 35 and 41, 47 and 53, 101 and 107, 83 and 89, 83 and 95, 23 and 29, 71 and 77 correspond, respectively, to the nucleotide sequences comprising the heavy chain ($V_H$) and light chain ($V_L$) variable regions of anti-CD27 antibody monoclonal antibodies 1F5, 1H8, 3H12, 3A10, 2C2, 2G9, 3H8, and 1G5.

The present invention also encompasses "conservative sequence modifications" of the sequences set forth in SEQ ID NOs: 5-112, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into SEQ ID NOs: 5-112 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-CD27 antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997))

Alternatively, in another embodiment, mutations can be introduced randomly along all or part of an anti-CD27 antibody coding sequence, such as by saturation mutagenesis, and the resulting modified anti-CD27 antibodies can be screened for binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "antigen" refers to any natural or synthetic immunogenic substance, such as a protein, peptide, or hapten. Suitable antigens for use in the present invention (e.g., in a vaccine in combination with an anti-CD27 antibody of the invention) include, for example, infectious disease antigens and tumor antigens, against which protective or therapeutic immune responses are desired, e.g., antigens expressed by a tumor cell or a pathogenic organism or infectious disease antigens. For example, suitable antigens include tumor-associated antigens for the prevention or treatment of cancers. Examples of tumor-associated antigens include, but are not limited to, sequences comprising all or part of the sequences of βhCG, gp100 or Pmel17, HER2/neu, WT1, mesothelin, CEA, gp100, MART1, TRP-2, melan-A, NY-ESO-1, NY-BR-1, NY-CO-58, MN (gp250), idiotype, MAGE-1, MAGE-3, MAGE-A3, Tyrosinase, Telomerase, SSX2 and MUC-1 antigens, and germ cell derived tumor antigens. Tumor associated antigens also include the blood group antigens, for example, $Le^a$, $Le^b$, LeX, LeY, H-2, B-1, B-2 antigens. Alternatively, more than one antigen can be included within the antigen-antibody constructs of the invention. For example, a MAGE antigen can be combined with other antigens such as melanin A, tyrosinase, and gp100 along with adjuvants such as GM-CSF or IL-12, and linked to an anti-APC antibody.

Other suitable antigens include viral antigens for the prevention or treatment of viral diseases. Examples of viral antigens include, but are not limited to, HIV-1 gag, HIV-1 env, HIV-1 nef, HBV (surface or core antigens), HPV, FAS, HSV-1, HSV-2, p17, ORF2 and ORF3 antigens. Examples of bacterial antigens include, but are not limited to, *Toxoplasma gondii* or *Treponema pallidum*. The antibody-bacterial antigen conjugates of the invention can be in the treatment or prevention of various bacterial diseases such as Anthrax, Botulism, Tetanus, Chlamydia, Cholera, Diphtheria, Lyme Disease, Syphilis and Tuberculosis. Other suitable antigens from infectious disease pathogens, such as viruses, bacteria, parasites and fungi are disclosed below.

Sequences of the foregoing antigens are well known in the art. For example, an example of a MAGE-3 cDNA sequence is provided in U.S. Pat. No. 6,235,525 (Ludwig Institute for Cancer Research); examples of NY-ESO-1 nucleic acid and protein sequences are provided in U.S. Pat. No. 5,804,381 and U.S. Pat. No. 6,069,233 (Ludwig Institute for Cancer Research); examples of Melan-A nucleic acid and protein sequences are provided in U.S. Pat. No. 5,620,886 and U.S. Pat. No. 5,854,203 (Ludwig Institute for Cancer Research); examples of NY-BR-1 nucleic acid and protein sequences are provided in U.S. Pat. No. 6,774,226 and U.S. Pat. No. 6,911,529 (Ludwig Institute for Cancer Research) and examples of NY-CO-58 nucleic acid and protein sequences are provided in WO 02090986 (Ludwig Institute for Cancer Research); an example of an amino acid sequence for the HER-2/neu protein is available at GENBANK® Accession No. AAA58637; and a nucleotide sequence (mRNA) for human carcinoembryonic antigen-like 1 (CEA-1) is available at GENBANK® Accession No. NM_020219.

An HPV antigen that may be used in the compositions and the methods of the invention may include, for example an HPV-16 antigen, an HPV-18 antigen, an HPV-31 antigen, an HPV-33 antigen and/or an HPV-35 antigen; and is suitably an HPV-16 antigen and/or HPV-18 antigen. A genome of HPV-16 is described in Virology, 145:181-185 (1985) and DNA sequences encoding HPV-18 are described in U.S. Pat. No. 5,840,306, the disclosures of which are incorporated by reference herein in their entirety. HPV-16 antigens (e.g., seroreactive regions of the E1 and/or E2 proteins of HPV-16) are described in U.S. Pat. No. 6,531,127, and HPV-18 antigens (e.g., seroreactive regions of the L1 and/or L2 proteins of HPV-18) are described in U.S. Pat. No. 5,840,306, the disclosures of which are incorporated by reference herein. Similarly, a complete genome for HBV is available at GENBANK® Accession No. NC_003977, the disclosure of which is incorporated herein. The genome of HCV is described in European Patent Application No. 318 216, the disclosure of which is incorporated herein. PCT/US90/01348, incorporated by reference herein, discloses sequence information of clones of the HCV genome, amino acid sequences of HCV viral proteins and methods of making and using such compositions for HCV vaccines comprising HCV proteins and peptides derived there from.

Antigenic peptides of proteins (i.e., those containing T cell epitopes) can be identified in a variety of manners well known in the art. For example, T cell epitopes can be predicted by analyzing the sequence of the protein using web-based predictive algorithms (BIMAS & SYFPEITHI) to generate potential MHC class I and II-binding peptides that match an internal database of 10,000 well characterized MHC binding peptides previously defined by CTLs. High scoring peptides can be ranked and selected as "interesting" on the basis of high affinity to a given MHC molecule.

Another method for identifying antigenic peptides containing T cell epitopes is by dividing the protein into non-overlapping peptides of desired length or overlapping peptides of desired lengths which can be produced recombinantly, synthetically, or in certain limited situations, by chemical cleavage of the protein and tested for immunogenic properties, e.g., eliciting a T cell response (i.e., proliferation or lymphokine secretion).

In order to determine precise T cell epitopes of the protein by, for example, fine mapping techniques, a peptide having T cell stimulating activity and thus comprising at least one T cell epitope, as determined by T cell biology techniques, can be modified by addition or deletion of amino acid residues at either the amino or carboxy terminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically. Peptides are selected based on various factors, including the strength of the T cell response to the peptide (e.g., stimulation index). The physical and chemical properties of these selected peptides (e.g., solubility, stability) can then be examined to determine whether the peptides are suitable for use in therapeutic compositions or whether the peptides require modification.

The term "antigen presenting cell" or "APC" is a cell that displays foreign antigen complexed with MHC on its surface. T-cells recognize this complex using T-cell receptor (TCR). Examples of APCs include, but are not limited to, dendritic cells (DCs), peripheral blood mononuclear cells (PBMC), monocytes (such as THP-1), B lymphoblastoid cells (such as C1R.A2, 1518 B-LCL) and monocyte-derived dendritic cells (DCs). Some APCs internalize antigens either by phagocytosis or by receptor-mediated endocytosis. Examples of APC receptors include, but are not limited to C-type lectins, such as, the human Dendritic and Epithelial Cell 205 receptor (CD27), and the human macrophage mannose receptor.

The term "antigen presentation" refers to the process by which APCs capture antigens and enables their recognition by T-cells, e.g., as a component of an MHC-I and/or MHC-II conjugate.

"MHC molecules" include two types of molecules, MHC class I and MHC class II. MHC class I molecules present antigen to specific CD8+ T cells and MHC class II molecules present antigen to specific CD4+ T cells. Antigens delivered exogenously to APCs are processed primarily for association with MHC class II. In contrast, antigens delivered endogenously to APCs are processed primarily for association with MHC class I.

As used herein, the term "immunostimulatory agent" includes but is not limited to compounds capable of stimulating APCs, such as DCs and macrophages. For example, suitable immunostimulatory agents for use in the present invention are capable of stimulating APCs, so that the maturation process of the APCs is accelerated, the proliferation of APCs is increased, and/or the recruitment or release of co-stimulatory molecules (e.g., CD80, CD86, ICAM-1, MHC molecules and CCR7) and pro-inflammatory cytokines (e.g., IL-1$\beta$, IL-6, IL-12, IL-15, and IFN-$\gamma$) is upregulated. Suitable immunostimulatory agents are also capable of increasing T cell proliferation. Such immunostimulatory agents include, but are not be limited to, CD40 ligand; FLT 3 ligand; cytokines, such as IFN-$\alpha$, IFN-$\beta$, IFN-$\gamma$ and IL-2; colony-stimulating factors, such as G-CSF (granulocyte colony-stimulating factor) and GM-CSF (granulocyte-macrophage colony-stimulating factor); an anti-CTLA-4 antibody, anti-PD1 antibody, anti-41BB antibody, or anti-OX-40 antibody; LPS (endotoxin); ssRNA; dsRNA; Bacille Calmette-Guerin (BCG); Levamisole hydrochloride; and intravenous immune globulins. In one embodiment an immunostimulatory agant may be a Toll-like Receptor (TLR) agonist. For example the immunostimulatory agent may be a TLR3 agonist such as double-stranded inosine:cytosine polynucleotide (Poly I:C, for example available as Ampligen™ from Hemispherx Bipharma, PA, US or Poly IC:LC from Oncovir) or Poly A:U; a TLR4 agonist such as monophosphoryl lipid A (MPL) or RC-529 (for example as available from GSK, UK); a TLR5 agonist such as flagellin; a TLR7 or TLR8 agonist such as an imidazoquinoline TLR7 or TLR $\delta$ agonist, for example imiquimod (eg Aldara™) or resiquimod and related imidazoquinoline agents (for example as available from 3M Corporation); or a TLR $\delta$ agonist such as a deoxynucleotide with unmethylated CpG motifs (so-called "CpGs", for example as available from Coley Pharmaceutical). A preferred immunostimulatory agent is a TLR3 agonist, preferably Poly I:C. Such immunostimulatory agents may be administered simultaneously, separately or sequentially with the antibodies and constructs of the present invention and may also be physically linked to the antibodies and constructs.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, the term antigen "cross-presentation" refers to presentation of exogenous protein antigens to T cells via MHC class I and class II molecules on APCs.

As used herein, the term "T cell-mediated response" refers to any response mediated by T cells, including effector T cells (e.g., CD8$^+$ cells) and helper T cells (e.g., CD4$^+$ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated primarily by CD8$^+$ T cells.

As used herein, the terms "inhibits" or "blocks" (e.g., referring to inhibition/blocking of binding of CD70 to CD27 on cells) are used interchangeably and encompass both partial and complete inhibition/blocking. The inhibition/blocking of CD70 preferably reduces or alters the normal level or type of activity that occurs when CD70 binding occurs without inhibition or blocking. Inhibition and blocking are also intended to include any measurable decrease in the binding affinity of CD70 when in contact with an anti-CD27 antibody as compared to CD70 not in contact with an anti-CD27 antibody, e.g., inhibits binding of CD70 by at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%. In a preferred embodiment, the anti-CD27 antibody inhibits binding of CD70 by at least about 70%. In another embodiment, the anti-CD27 antibody inhibits binding of CD70 by at least 80%

As used herein, the term "inhibits growth" (e.g., referring to cells) is intended to include any measurable decrease in the growth of a cell, e.g., the inhibition of growth of a cell by at least about 10%, 20%, 30%, 40%, 50%, 60%, 70%, 80%, 90%, 99%, or 100%.

The terms "inducing an immune response" and "enhancing an immune response" are used interchangeably and refer the stimulation of an immune response (i.e., either passive or adaptive) to a particular antigen. The terms "induce" as used with respect to inducing CDC or ADCC refer to the stimulation of particular direct cell killing mechanisms. For example, in one embodiment, the antibody induces at least about 20, 25, 30, 35, 40, 45, 50, 55, or 60% lysis via CDC of CD27 expressing cells at a concentration of 10 µg/ml. In a preferred embodiment, the antibody induces at least about 40% lysis via CDC of CD27 expressing cells at a concentration of 10 µg/ml. In another embodiment, the antibody induces at least about 20, 25, 30, 35, 40, 45, 50, 55, 60, 65, 70, 75, 80, or 85% lysis via ADCC (i.e., specific lysis) of CD27 expressing cells at a concentration of 10 µg/ml. In a preferred embodiment, the antibody induces at least about 40% lysis via ADCC of CD27 expressing cells at a concentration of 10 µg/ml.

The terms "treat," "treating," and "treatment," as used herein, refer to therapeutic or preventative measures described herein. The methods of "treatment" employ administration to a subject, in need of such treatment, a human antibody of the present invention, for example, a subject in need of an enhanced immune response against a particular antigen or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

The term "patient" includes human and other mammalian subjects that receive either prophylactic or therapeutic treatment.

As used herein, the term "subject" includes any human or non-human animal. For example, the methods and compositions of the present invention can be used to treat a subject with an immune disorder. The term "non-human animal" includes all vertebrates, e.g., mammals and non-mammals, such as non-human primates, sheep, dog, cow, chickens, amphibians, reptiles, etc.

Various aspects of the invention are described in further detail in the following subsections.

I. PRODUCTION OF ANTIBODIES TO CD27

The present invention encompasses antibodies, e.g., fully human antibodies, that bind CD27, e.g., human CD27. Exemplary monoclonal antibodies that bind CD27 include 1F5, 1H8, 3H12, 3A10, 2C2, 2G9, 3H8, and 1G5. Monoclonal antibodies of the invention can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

Accordingly, in one embodiment, a hybridoma method is used for producing an antibody that binds human CD27. In this method, a mouse or other appropriate host animal can be immunized with a suitable antigen in order to elicit lymphocytes that produce or are capable of producing antibodies that will specifically bind to the antigen used for immunization. Alternatively, lymphocytes may be immunized in vitro. Lymphocytes can then be fused with myeloma cells using a suitable fusing agent, such as polyethylene glycol, to form a hybridoma cell (Goding, Monoclonal Antibodies: Principles and Practice, pp. 59-103 (Academic Press, 1986)). Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

In another embodiment, antibodies and antibody portions that bind human CD27 can be isolated from antibody phage libraries generated using the techniques described in, for example, McCafferty et al., Nature, 348:552-554 (1990). Clackson et al., Nature, 352:624-628 (1991), Marks et al., *J. Mol. Biol.*, 222:581-597 (1991) and Hoet et al (2005) *Nature Biotechnology* 23, 344-348; U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Additionally, production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.,* 21:2265-2266 (1993)) may also be used.

In a particular embodiment, the antibody that binds human CD27 is produced using the phage display technique described by Hoet et al., supra. This technique involves the generation of a human Fab library having a unique combination of immunoglobulin sequences isolated from human donors and having synthetic diversity in the heavy-chain CDRs is generated. The library is then screened for Fabs that bind to human CD27.

The preferred animal system for generating hybridomas which produce antibodies of the invention is the murine system. Hybridoma production in the mouse is well known in the art, including immunization protocols and techniques for isolating and fusing immunized splenocytes.

In one embodiment, antibodies directed against CD27 are generated using transgenic or transchromosomal mice carrying parts of the human immune system rather than the mouse system. In one embodiment, the invention employs transgenic mice, referred to herein as "HuMAb mice" which contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* Vol. 13: 65-93, and Harding, F. and Lonberg, N. (1995) *Ann. N.Y. Acad. Sci.* 764:536-546). The preparation of HuMAb mice is described in detail in Section II below and in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Lonberg et al., (1994) *Nature* 368(6474): 856-859; Lonberg, N. (1994) *Handbook of Experimental Pharmacology* 113:49-101; Taylor, L. et al. (1994) *International Immunology* 6: 579-591; Lonberg, N. and Huszar, D. (1995) *Intern. Rev. Immunol. Vol.* 13: 65-93; Harding, F. and Lonberg, N. (1995) *Ann. N.Y. Acad. Sci.* 764:536-546; Fishwild, D. et al. (1996) *Nature Biotechnology* 14: 845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992.

Immunizations

To generate fully human antibodies to CD27, transgenic or transchromosomal mice containing human immunoglobulin genes (e.g., HCo12, HCo7 or KM mice) can be immunized with a purified or enriched preparation of the CD27 antigen and/or cells expressing CD27, as described, for example, by Lonberg et al. (1994) *Nature* 368(6474): 856-859; Fishwild et al. (1996) *Nature Biotechnology* 14: 845-851 and WO 98/24884. As described herein, HuMAb mice are immunized either with recombinant CD27 proteins or cell lines expressing CD27 as immunogens. Alternatively, mice can be immunized with DNA encoding human CD27. Preferably, the mice will be 6-16 weeks of age upon the first infusion. For example, a purified or enriched preparation (5-50 µg) of the recombinant CD27 antigen can be used to immunize the HuMAb mice intraperitoneally. In the event that immunizations using a purified or enriched preparation of the CD27 antigen do not result in antibodies, mice can also be immunized with cells expressing CD27, e.g., a cell line, to promote immune responses. Exemplary cell lines include CD27-overexpressing stable CHO and Raji cell lines.

Cumulative experience with various antigens has shown that the HuMAb transgenic mice respond best when initially immunized intraperitoneally (IP) or subcutaneously (SC) with antigen in complete Freund's adjuvant, followed by every other week IP/SC immunizations (up to a total of 10) with antigen in incomplete Freund's adjuvant. The immune response can be monitored over the course of the immunization protocol with plasma samples being obtained by retro-orbital bleeds. The plasma can be screened by ELISA (as described below), and mice with sufficient titers of anti-CD27 human immunoglobulin can be used for fusions. Mice can be boosted intravenously with antigen 3 days before sacrifice and removal of the spleen.

Generation of Hybridomas Producing Monoclonal Antibodies to CD27

To generate hybridomas producing monoclonal antibodies to CD27, splenocytes and lymph node cells from immunized mice can be isolated and fused to an appropriate immortalized cell line, such as a mouse myeloma cell line. The resulting hybridomas can then be screened for the production of antigen-specific antibodies. For example, single cell suspensions of splenic lymphocytes from immunized mice can be fused to SP2/0-Ag8.653 nonsecreting mouse myeloma cells (ATCC, CRL 1580) with 50% PEG (w/v). Cells can be plated at approximately $1 \times 10^5$ in flat bottom microtiter plate, followed by a two week incubation in selective medium containing besides usual reagents 10% fetal Clone Serum, 5-10% origen hybridoma cloning factor (IGEN) and 1×HAT (Sigma). After approximately two weeks, cells can be cultured in medium in which the HAT is replaced with HT. Individual wells can then be screened by ELISA for human anti-CD27 monoclonal IgM and IgG antibodies, or for binding to the surface of cells expressing CD27, e.g., a CHO cell line expressing CD27, by FLISA (fluorescence-linked immunosorbent assay). Once extensive hybridoma growth occurs, medium can be observed usually after 10-14 days. The antibody secreting hybridomas can be replated, screened again, and if still positive for IgG, anti-CD27 monoclonal antibodies can be subcloned at least twice by limiting dilution. The stable subclones can then be cultured in vitro to generate antibody in tissue culture medium for characterization.

Generation of Transfectomas Producing Monoclonal Antibodies to CD27

Antibodies of the invention also can be produced in a host cell transfectoma using, for example, a combination of recombinant DNA techniques and gene transfection methods as is well known in the art (Morrison, S. (1985) Science 229:1202).

For example, in one embodiment, the gene(s) of interest, e.g., human antibody genes, can be ligated into an expression vector such as a eukaryotic expression plasmid such as used by GS gene expression system disclosed in WO 87/04462, WO 89/01036 and EP 338 841 or other expression systems well known in the art. The purified plasmid with the cloned antibody genes can be introduced in eukaryotic host cells such as CHO-cells or NSO-cells or alternatively other eukaryotic cells like a plant derived cells, fungi or yeast cells. The method used to introduce these genes could be methods described in the art such as electroporation, lipofectine, lipofectamine or other. After introducing these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively these cloned antibody genes can be expressed in other expression systems such as E. coli or in complete organisms or can be synthetically expressed.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323-327; Jones, P. et al., 1986, Nature 321:522-525; and Queen, C. et al., 1989, Proc. Natl. Acad. See. U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from a hybridoma are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266:19867-19870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, leader sequence, translation initiation, leader sequence, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors were constructed so that PCR amplified V heavy and V kappa light chain cDNA sequences could be used to reconstruct complete heavy and light chain minigenes. These plasmids can be used to express completely human $IgG_1\kappa$ or $IgG_4\kappa$ antibodies. Fully human and chimeric antibodies of the present invention also include IgG2, IgG3, IgE, IgA, IgM, and IgD antibodies. Similar plasmids can be constructed for expression of other heavy chain isotypes, or for expression of antibodies comprising lambda light chains.

Thus, in another aspect of the invention, structural features of anti-CD27 antibodies of the invention are used to create structurally related anti-CD27 antibodies that retain at least one functional property of the antibodies of the invention, such as, for example, (1) inhibits (e.g., completely or partially blocks) binding of CD70 to CD27 expressing cells by at least about 70% (e.g., by at least about 70%, or by at least 70%, at an antibody concentration of 10 μg/ml);
(2) binds to human CD27 with an equilibrium dissociation constant Kd of $10^{-9}$ M or less, or alternatively, an equilibrium association constant Ka of $10^{+9}$ $M^{-1}$ or greater
(3) induces at least about 30% complement mediated cytotoxicity (CDC) of CD27 expressing cells at a concentration of 10 μg/ml (or induces at least 30%, or at least about 40% or at least 40% CDC of CD27 expressing cells at a concentration of 10 μg/ml);
(4) induces at least about 30% specific ADCC-mediated lysis of CD27 expressing cells at a concentration of 10 μg/ml (or induces at least 30%, or at least about 40% or at least 40% specific ADCC-mediated lysis of CD27 expressing cells at a concentration of 10 μg/ml);
(5) prevents or inhibits the growth of CD27-expressing tumor cells in a xenograft model (e.g., reduces tumor size in severe combined immunodeficiency (SCID) mice by at least about 50% 20-days post tumor cell inoculation in vivo at 0.5 mg ip on at least 6 days);
(6) induces or enhances antigen specific immune responses when combined with a vaccine or other antigen;
(7) induces or enhances immune responses, in particular but not limited to TH1 immune responses;
(8) induces or enhances T-cell activity, in particular but not limited to specific CD8+ T-cell numbers or functional activity, or T cell proliferation or activation; and/or
(9) reduces or inhibits T cell proliferation or activation. In one embodiment, one or more CDR regions of antibodies of the invention can be combined recombinantly with known framework regions and CDRs to create additional, recombinantly-engineered, anti-CD27 antibodies of the invention. The heavy and light chain variable framework regions can be derived from the same or different antibody sequences. The antibody sequences can be the sequences of naturally occurring antibodies or can be consensus sequences of several antibodies. See Kettleborough et al., *Protein Engineering* 4:773 (1991); Kolbinger et al., *Protein Engineering* 6:971 (1993) and Carter et al., WO 92/22653.

Accordingly, in another embodiment, the invention provides a method for preparing an anti-CD27 antibody including: preparing an antibody including (1) heavy chain framework regions and heavy chain CDRs, where at least one of the heavy chain CDRs includes an amino acid sequence selected from the amino acid sequences of CDRs shown in SEQ ID NOs: 8, 9, 10, 26, 27, 28, 38, 39, 40, 50, 51, 52, 62, 63, 64, 74, 75, 76, 86, 87, 88, 104, 105, 106; and (2) light chain framework regions and light chain CDRs, where at least one of the light chain CDRs includes an amino acid sequence selected from the amino acid sequences of CDRs shown in SEQ ID NOs: SEQ ID NOs: 14, 15, 16, 20, 21, 22, 32, 33, 34, 44, 45, 46, 56, 57, 58, 68, 69, 70, 80, 81, 82, 92, 93, 94, 98, 99, 100, 110, 111, 112; where the antibody retains the ability to bind to CD27. The ability of the antibody to bind CD27 can be determined using standard binding assays, such as those set forth in the Examples (e.g., an ELISA or a FLISA).

It is well known in the art that antibody heavy and light chain CDR3 domains play a particularly important role in the binding specificity/affinity of an antibody for an antigen (see, Hall et al., *J. Immunol.*, 149:1605-1612 (1992); Polymenis et al., *J. Immunol.*, 152:5318-5329 (1994); Jahn et al., *Immunobiol.*, 193:400-419 (1995); Klimka et al., *Brit. J. Cancer*, 83:252-260 (2000); Beiboer et al., *J. Mol. Biol,* 296:833-849 (2000); Rader et al., *Proc. Natl. Acad. Sci. USA*, 95:8910-8915 (1998); Barbas et al., *J. Am. Chem. Soc.*, 116:2161-2162 (1994); Ditzel et al., *J. Immunol.*, 157:739-749 (1996)). Accordingly, the recombinant antibodies of the invention prepared as set forth above preferably comprise the heavy and/or light chain CDR3s of antibodies 1F5, 1H8, 3H12, 3A10, 2C2, 2G9, 3H8, and 1G5. The antibodies further can comprise the CDR2s of antibodies 1F5, 1H8, 3H12, 3A10, 2C2, 2G9, 3H8, and 1G5. The antibodies further can comprise the CDR1s of antibodies 1F5, 1H8, 3H12, 3A10, 2C2, 2G9, 3H8, and 1G5. The antibodies can further comprise any combinations of the CDRs.

Accordingly, in another embodiment, the invention further provides anti-CD27 antibodies comprising: (1) heavy chain framework regions, a heavy chain CDR1 region, a heavy chain CDR2 region, and a heavy chain CDR3 region, wherein the heavy chain CDR3 region is selected from the CDR3s of 1F5, 1H8, 3H12, 3A10, 2C2, 2G9, 3H8, and 1G5 and (2) light chain framework regions, a light chain CDR1 region, a light chain CDR2 region, and a light chain CDR3 region, wherein the light chain CDR3 region is selected from the CDR3s of 1F5, 1H8, 3H12, 3A10, 2C2, 2G9, 3H8, and 1G5, wherein the antibody binds CD27. The antibody may further include the heavy chain CDR2 and/or the light chain CDR2 of antibodies 1F5, 1H8, 3H12, 3A10, 2C2, 2G9, 3H8, and 1G5. The antibody may further comprise the heavy chain CDR1 and/or the light chain CDR1 of antibodies 1F5, 1H8, 3H12, 3A10, 2C2, 2G9, 3H8, and 1G5.

Generation of Antibodies Having Modified Sequences

In another embodiment, the variable region sequences, or portions thereof, of the anti-CD27 antibodies of the invention are modified to create structurally related anti-CD27 antibodies that retain binding (i.e., to the same epitope as the unmodified antibody) and, thus, are functionally equivalent. Methods for identifying residues that can be altered without removing antigen binding are well-known in the art (see, e.g., Marks et al. (*Biotechnology* (1992) 10(7):779-83 (monoclonal antibodies diversification by shuffling light chain variable regions, then heavy chain variable regions with fixed CDR3 sequence changes), Jespers et al. (1994) Biotechnology 12(9):899-903 (selection of human antibodies from phage display repertoires to a single epitope of an antigen), Sharon et al. (1986) *PNAS USA* 83(8):2628-31 (site-directed mutagenesis of an invariant amino acid residue at the variable-diversity segments junction of an antibody); Casson et al. (1995) *J. Immunol.* 155(12):5647-54 (evolution of loss and change of specificity resulting from random mutagenesis of an antibody heavy chain variable region).

Accordingly, in one aspect of the invention, the CDR1, 2, and/or 3 regions of the engineered antibodies described above can comprise the exact amino acid sequence(s) as those of antibodies 1F5, 1H8, 3H12, 3A10, 2C2, 2G9, 3H8, and 1G5 disclosed herein. However, in other aspects of the invention, the antibodies comprise derivatives from the exact CDR sequences of 1F5, 1H8, 3H12, 3A10, 2C2, 2G9, 3H8, and 1G5 yet still retain the ability of to bind CD27 effectively. Such sequence modifications may include one or more amino acid additions, deletions, or substitutions, e.g., conservative sequence modifications as described above. Sequence modifications may also be based on the consensus sequences described above for the particular CDR1, CDR2, and CDR3 sequences of antibodies 1F5, 1H8, 3H12, 3A10, 2C2, 2G9, 3H8, and 1G5.

Accordingly, in another embodiment, the engineered antibody may be composed of one or more CDRs that are, for example, 90%, 95%, 98% or 99.5% identical to one or more CDRs of antibodies 1F5, 1H8, 3H12, 3A10, 2C2, 2G9, 3H8, and 1G5. Ranges intermediate to the above-recited values, e.g., CDRs that are 90-95%, 95-98%, or 98-100% identical identity to one or more of the above sequences are also intended to be encompassed by the present invention.

In another embodiment, one or more residues of a CDR may be altered to modify binding to achieve a more favored on-rate of binding, a more favored off-rate of binding, or both, such that an idealized binding constant is achieved. Using this strategy, an antibody having ultra high binding affinity of, for example, $10^{10}$ $M^{-1}$ or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

In addition to or instead of modifications within the CDRs, modifications can also be made within one or more of the framework regions, FR1, FR2, FR3 and FR4, of the heavy and/or the light chain variable regions of a antibody, so long as these modifications do not eliminate the binding affinity of the antibody. For example, one or more non-germline amino acid residues in the framework regions of the heavy and/or the light chain variable region of a antibody of the invention, is substituted with a germline amino acid residue, i.e., the corresponding amino acid residue in the human germline sequence for the heavy or the light chain variable region, which the antibody has significant sequence identity with. For example, an antibody chain can be aligned to a germline antibody chain which it shares significant sequence identity with, and the amino acid residues which do not match between antibody framework sequence and the germline chain framework can be substituted with corresponding residues from the germline sequence. When an amino acid differs between a antibody variable framework region and an equivalent human germline sequence variable framework region, the antibody framework amino acid should usually be substituted by the equivalent human germline sequence amino acid if it is reasonably expected that the amino acid falls within one of the following categories:

(1) an amino acid residue which noncovalently binds antigen directly, (2) an amino acid residue which is adjacent to a CDR region, (3) an amino acid residue which otherwise interacts with a CDR region (e.g., is within about 3-6 Å of a CDR region as determined by computer modeling), or (4) an amino acid reside which participates in the VL-VH interface.

Residues which "noncovalently bind antigen directly" include amino acids in positions in framework regions which have a good probability of directly interacting with amino acids on the antigen according to established chemical forces, for example, by hydrogen bonding, Van der Waals forces, hydrophobic interactions, and the like. Accordingly, in one embodiment, an amino acid residue in the framework region of a antibody of the invention is substituted with the corresponding germline amino acid residue which noncovalently binds antigen directly.

Residues which are "adjacent to a CDR region" include amino acid residues in positions immediately adjacent to one or more of the CDRs in the primary sequence of the antibody, for example, in positions immediately adjacent to a CDR as defined by Kabat, or a CDR as defined by Chothia (see e.g., Chothia and Lesk *J. Mol. Biol.* 196:901 (1987)). Accordingly, in one embodiment, an amino acid residue within the framework region of an antibody of the invention is substituted with a corresponding germline amino acid residue which is adjacent to a CDR region.

Residues that "otherwise interact with a CDR region" include those that are determined by secondary structural analysis to be in a spatial orientation sufficient to affect a CDR region. Such amino acids will generally have a side chain atom within about 3 angstrom units (Å) of some atom in the CDRs and must contain an atom that could interact with the CDR atoms according to established chemical forces, such as those listed above. Accordingly, in one embodiment, an amino acid residue within the framework region of an antibody of the invention is substituted with the corresponding germline amino acid residue which otherwise interacts with a CDR region.

The amino acids at several positions in the framework are known to be important for determining CDR confirmation (e.g., capable of interacting with the CDRs) in many antibodies (Chothia and Lesk, supra, Chothia et al., supra and Tramontano et al., J. Mol. Biol. 215:175 (1990), all of which are incorporated herein by reference). These authors identified conserved framework residues important for CDR conformation by analysis of the structures of several known antibodies. The antibodies analyzed fell into a limited number of structural or "canonical" classes based on the conformation of the CDRs. Conserved framework residues within members of a canonical class are referred to as "canonical" residues. Canonical residues include residues 2, 25, 29, 30, 33, 48, 64, 71, 90, 94 and 95 of the light chain and residues 24, 26, 29, 34, 54, 55, 71 and 94 of the heavy chain. Additional residues (e.g., CDR structure-determining residues) can be identified according to the methodology of Martin and Thorton (1996) J. Mol. Biol. 263:800. Notably, the amino acids at positions 2, 48, 64 and 71 of the light chain and 26-30, 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs. Additional residues which may effect conformation of the CDRs can be identified according to the methodology of Foote and Winter (1992) J. Mol. Biol. 224:487. Such residues are termed "vernier" residues and are those residues in the framework region closely underlying (i.e., forming a "platform" under) the CDRs.

Residues which "participate in the VL-VH interface" or "packing residues" include those residues at the interface between VL and VH as defined, for example, by Novotny and Haber, Proc. Natl. Acad. Sci. USA, 82:4592-66 (1985) or Chothia et al, supra.

Occasionally, there is some ambiguity about whether a particular amino acid falls within one or more of the above-mentioned categories. In such instances, alternative variant antibodies are produced, one of which has that particular substitution, the other of which does not. Alternative variant antibodies so produced can be tested in any of the assays described herein for the desired activity, and the preferred antibody selected.

Additional candidates for substitution within the framework region are amino acids that are unusual or "rare" for an antibody at that position. These amino acids can be substituted with amino acids from the equivalent position of the human germline sequence or from the equivalent positions of more typical antibodies. For example, substitution may be desirable when the amino acid in a framework region of the antibody is rare for that position and the corresponding amino acid in the germline sequence is common for that position in immunoglobulin sequences; or when the amino acid in the antibody is rare for that position and the corresponding amino acid in the germline sequence is also rare, relative to other sequences. It is contemplated that by replacing an unusual amino acid with an amino acid from the germline sequence that happens to be typical for antibodies, the antibody may be made less immunogenic.

The term "rare", as used herein, indicates an amino acid occurring at that position in less than about 20%, preferably less than about 10%, more preferably less than about 5%, even more preferably less than about 3%, even more preferably less than about 2% and even more preferably less than about 1% of sequences in a representative sample of sequences, and the term "common", as used herein, indicates an amino acid occurring in more than about 25% but usually more than about 50% of sequences in a representative sample. For example, all light and heavy chain variable region sequences are respectively grouped into "subgroups" of sequences that are especially homologous to each other and have the same amino acids at certain critical positions (Kabat et al., supra). When deciding whether an amino acid in an antibody sequence is "rare" or "common" among sequences, it will often be preferable to consider only those sequences in the same subgroup as the antibody sequence.

In general, the framework regions of antibodies are usually substantially identical, and more usually, identical to the framework regions of the human germline sequences from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting immunoglobulin. Thus, in one embodiment the variable framework region of the antibody shares at least 85% sequence identity to a human germline variable framework region sequence or consensus of such sequences. In another embodiment, the variable framework region of the antibody shares at least 90%, 95%, 96%, 97%, 98% or 99% sequence identity to a human germline variable framework region sequence or consensus of such sequences.

In addition to simply binding CD27, an antibody may be selected for its retention of other functional properties of antibodies of the invention, such as, for example:

(1) inhibits (e.g., completely or partially blocks) binding of CD70 to CD27 expressing cells by at least about 70%;
(2) binds to human CD27 with an equilibrium dissociation constant Kd of $10^{-9}$ M or less, or alternatively, an equilibrium association constant Ka of $10^{+9}$ M$^{-1}$ or greater;
(3) induces at least about 40% complement mediated cytotoxicity (CDC) of CD27 expressing cells at a concentration of 10 μg/ml; and/or
(4) induces at least about 40% ADCC mediated specific lysis of CD27 expressing cells at a concentration of 10 μg/ml.

Characterization of Monoclonal Antibodies to CD27

Monoclonal antibodies of the invention can be characterized for binding to CD27 using a variety of known techniques. Generally, the antibodies are initially characterized by ELISA. Briefly, microtiter plates can be coated with purified CD27 in PBS, and then blocked with irrelevant proteins such as bovine serum albumin (BSA) diluted in PBS. Dilutions of plasma from CD27-immunized mice are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405. Preferably, mice which develop the highest titers will be used for fusions.

An ELISA assay as described above can be used to screen for antibodies and, thus, hybridomas that produce antibodies that show positive reactivity with the CD27 immunogen. Hybridomas that bind, preferably with high affinity, to CD27 can then be subcloned and further characterized. One clone from each hybridoma, which retains the reactivity of the parent cells (by ELISA), can then be chosen for making a cell bank, and for antibody purification.

To purify anti-CD27 antibodies, selected hybridomas can be grown in roller bottles, two-liter spinner-flasks or other culture systems. Supernatants can be filtered and concentrated before affinity chromatography with protein A-Sepharose (Pharmacia, Piscataway, N.J.) to purify the protein. After buffer exchange to PBS, the concentration can be determined by $OD_{280}$ using 1.43 extinction coefficient or preferably by nephelometric analysis. IgG can be checked by gel electrophoresis and by antigen specific method.

To determine if the selected anti-CD27 monoclonal antibodies bind to unique epitopes, each antibody can be biotinylated using commercially available reagents (Pierce, Rockford, Ill.). Biotinylated MAb binding can be detected with a streptavidin labeled probe. To determine the isotype of purified antibodies, isotype ELISAs can be performed using art recognized techniques. For example, wells of microtiter plates can be coated with 10 µg/ml of anti-Ig overnight at 4° C. After blocking with 5% BSA, the plates are reacted with 10 µg/ml of monoclonal antibodies or purified isotype controls, at ambient temperature for two hours. The wells can then be reacted with either IgG1 or other isotype specific conjugated probes. Plates are developed and analyzed as described above.

To test the binding of monoclonal antibodies to live cells expressing CD27, flow cytometry can be used. Briefly, cell lines and/or human PBMCs expressing membrane-bound CD27 (grown under standard growth conditions) are mixed with various concentrations of monoclonal antibodies in PBS containing 0.1% BSA at 4° C. for 1 hour. After washing, the cells are reacted with Fluorescein-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-CD27 IgGs can be further tested for reactivity with the CD27 antigen by Western blotting. Briefly, cell extracts from cells expressing CD27 can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, Mo.).

Methods for analyzing binding affinity, cross-reactivity, and binding kinetics of various anti-CD27 antibodies include standard assays known in the art, for example, Biacore surface plasmon resonance (SPR) analysis using a Biacore 2000 SPR instrument (Biacore AB, Uppsala, Sweden), as described in Example 2 herein.

II. IMMUNOTOXINS

In another embodiment, the antibodies of the present invention are linked to a therapeutic moiety, such as a cytotoxin, a drug or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a dendritic-related disorder, such as an autoimmune or inflammatory disease, or graft versus host disease.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

III. COMPOSITIONS

In another embodiment, the present invention provides a composition, e.g., a composition, containing one or a combination of monoclonal antibodies of the present invention, formulated together with a carrier (e.g., a pharmaceutically acceptable carrier). Compositions containing bispecific molecules which comprise an antibody of the present invention are also provided. In one embodiment, the compositions include a combination of multiple (e.g., two or more) isolated antibodies of the invention. Preferably, each of the antibodies of the composition binds to a distinct, pre-selected epitope of CD27.

Pharmaceutical compositions of the invention also can be administered in combination therapy, i.e., combined with other agents. For example, the combination therapy can include a composition of the present invention with at least one or more additional therapeutic agents, such as anti-inflammatory agents, DMARDs (disease-modifying anti-rheumatic drugs), immunosuppressive agents, and chemotherapeutics. The pharmaceutical compositions of the invention can also be administered in conjunction with radiation therapy. Co-administration with other antibodies is also encompassed by the invention.

As used herein, the terms "carrier" and "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

Examples of adjuvants which may be used with the antibodies and constructs of the present invention include: Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatised polysaccharides; polyphosphazenes; biodegradable microspheres; cytokines, such as GM-CSF, interleukin-2, -7, -12, and other like factors; 3D-MPL; CpG oligonucleotide; and monophosphoryl lipid A, for example 3-de-O-acylated monophosphoryl lipid A.

MPL adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996.

Further alternative adjuvants include, for example, saponins, such as Quil A, or derivatives thereof, including QS21 and QS7 (Aquila Biopharmaceuticals Inc., Framingham, Mass.); Escin; Digitonin; or Gypsophila or Chenopodium quinoa saponins; Montanide ISA 720 (Seppic, France); SAF (Chiron, Calif., United States); ISCOMS (CSL), MF-59 (Chiron); the SBAS series of adjuvants (e.g., SBAS-2 or SBAS-4, available from SmithKline Beecham, Rixensart, Belgium); Detox (Enhanzyn™) (Corixa, Hamilton, Mont.); RC-529 (Corixa, Hamilton, Mont.) and other aminoalkyl glucosaminide 4-phosphates (AGPs); polyoxyethylene ether adjuvants such as those described in WO 99/52549A1; synthetic imidazoquinolines such as imiquimod [S-26308, R-837], (Harrison, et al., Vaccine 19: 1820-1826, 2001; and resiquimod [S-28463, R-848] (Vasilakos, et al., Cellular immunology 204: 64-74, 2000; Schiff bases of carbonyls and amines that are constitutively expressed on antigen presenting cell and T-cell surfaces, such as tucaresol (Rhodes, J. et al., Nature 377: 71-75, 1995); cytokine, chemokine and co-stimulatory molecules as either protein or peptide, including for example pro-inflammatory cytokines such as Interferon, GM-CSF, IL-1 alpha, IL-1 beta, TGF-alpha and TGF-beta, Th1 inducers such as interferon gamma, IL-2, IL-12, IL-15, IL-18 and IL-21, Th2 inducers such as IL-4, IL-5, IL-6, IL-10 and IL-13 and other chemokine and co-stimulatory genes such as MCP-1, MIP-1 alpha, MIP-1 beta, RANTES, TCA-3, CD80, CD86 and CD40L; immunostimulatory agents targeting ligands such as CTLA-4 and L-selectin, apoptosis stimulating proteins and peptides such as Fas; synthetic lipid based adjuvants, such as vaxfectin, (Reyes et al., Vaccine 19: 3778-3786, 2001) squalene, alpha-tocopherol, polysorbate 80, DOPC and cholesterol; endotoxin, [LPS], (Beutler, B., Current Opinion in Microbiology 3: 23-30, 2000); ligands that trigger Toll receptors to produce Th1-inducing cytokines, such as synthetic Mycobacterial lipoproteins, Mycobacterial protein p19, peptidoglycan, teichoic acid and lipid A; and CT (cholera toxin, subunits A and B) and LT (heat labile enterotoxin from *E. coli*, subunits A and B), heat shock protein family (HSPs), and LLO (listeriolysin O; WO 01/72329). These and various further Toll-like Receptor (TLR) agonists are described for example in Kanzler et al, *Nature Medicine*, May 2007, Vol 13, No 5. A preferred immunostimulatory agent for use in combination with an anti-CD27 antibody of the invention is a TLR3 agonist, such as Poly IC.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Acceptable diluents include saline and aqueous buffer solutions. Liposomes include water-in-oil-in-water CGF emulsions as well as conventional liposomes (Strejan et al. (1984) *J. Neuroimmunol.* 7:27).

Carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the antibodies of the invention may be administered once or twice weekly by subcutaneous or intramuscular injection or once or twice monthly by subcutaneous or intramuscular injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399, 163, 5,383,851, 5,312,335, 5,064,413, 4,941,880, 4,790,824, or 4,596,556. Examples of well-known implants and modules useful in the present invention include: U.S. Pat. No. 4,487, 603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V.V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the inventions, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

IV. USES AND METHODS OF THE INVENTION

In one embodiment, the antibodies, bispecific molecules, and compositions of the present invention can be used to treat and/or prevent (e.g., immunize against) a variety of diseases and conditions.

One of the primary disease indications that can be treated is cancer. In particular, an anti-CD27 antibody that induces or enhances an immune response can be used in the treatment of cancer. Types of cancers include, but are not limited to, leukemia, acute lymphocytic leukemia, acute myelocytic leukemia, myeloblasts promyelocyte myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system. Preferred cancers include CD27-expressing tumors selected from the group consisting of chronic lymphocytic leukemia, mantle cell lymphoma, primary central nervous system lymphoma, Burkitt's lymphoma and marginal zone B cell lymphoma.

Other disease indications for use of an anti-CD27 antibody that induces or enhances an immune response include bacterial, fungal, viral and parasitic infectious diseases. Other disease indications for use of an anti-CD27 antibody that inhibits or reduces an immune response include graft rejection, allergy and autoimmune diseases.

Exemplary autoimmune diseases include, but are not limited to, multiple sclerosis, rheumatoid arthritis, type 1 diabetes, psoriasis, Crohn's disease and other inflammatory bowel diseases such as ulcerative colitis, systemic lupus eythematosus (SLE), autoimmune encephalomyelitis, myasthenia gravis (MG), Hashimoto's thyroiditis, Goodpasture's syndrome, pemphigus, Graves disease, autoimmune hemolytic anemia, autoimmune thrombocytopenic purpura, scleroderma with anti-collagen antibodies, mixed connective tissue disease, polypyositis, pernicious anemia, idiopathic Addison's disease, autoimmune associated infertility, glomerulonephritis, crescentic glomerulonephritis, proliferative glomerulonephritis, bullous pemphigoid, Sjogren's syndrome, psoriatic arthritis, insulin resistance, autoimmune diabetes mellitus, autoimmune hepatitis, autoimmune hemophilia, autoimmune lymphoproliferative syndrome (ALPS), autoimmune hepatitis, autoimmune hemophilia, autoimmune lymphoproliferative syndrome, autoimmune uveoretinitis, Guillain-Bare syndrome, arteriosclerosis and Alzheimer's disease. Exemplary allergic disorders include, but are not limited to allergic conjunctivitis, vernal conjunctivitis, vernal keratoconjunctivitis, and giant papillary conjunctivitis; nasal allergic disorders, including allergic rhinitis and sinusitis; otic allergic disorders, including eustachian tube itching; allergic disorders of the upper and lower airways, including intrinsic and extrinsic asthma; allergic disorders of the skin, including dermatitis, eczema and urticaria; and allergic disorders of the gastrointestinal tract.

In another aspect, an antibody of the invention is administered in combination with a vaccine, to enhance the immune response against the vaccine antigen, for example a tumor antigen (to thereby enhance the immune response against the tumor) or an antigen from an infectious disease pathogen (to thereby enhance the immune response against the infectious disease pathogen). Accordingly, in this embodiment, a vaccine antigen can comprise, for example, an antigen or antigenic composition capable of eliciting an immune response against a tumor or against an infectious disease pathogen such as a virus, a bacteria, a parasite or a fungus. The antigen or antigens can be, for example, peptides/proteins, polysaccharides and/or lipids. The antigen or antigens be derived from tumors, such as the various tumor antigens previously disclosed herein. Alternatively, the antigen or antigens can be derived from pathogens such as viruses, bacteria, parasites and/or fungi, such as the various pathogen antigens previously disclosed herein. Additional examples of suitable pathogen antigens include, but are not limited to, the following:

Viral antigens or antigenic determinants can be derived from, for example: Cytomegalovirus (especially Human, such as gB or derivatives thereof); Epstein Barr virus (such as gp350); flaviviruses (e.g. Yellow Fever Virus, Dengue Virus, Tick-borne encephalitis virus, Japanese Encephalitis Virus); hepatitis virus such as hepatitis B virus (for example Hepatitis B Surface antigen such as the PreS1, PreS2 and S antigens described in EP-A-414 374; EP-A-0304 578, and EP-A-198474), hepatitis A virus, hepatitis C virus and hepatitis E virus; HIV-1, (such as tat, nef, gp120 or gp160); human herpes viruses, such as gD or derivatives thereof or Immediate Early protein such as ICP27 from HSV1 or HSV2; human papilloma viruses (for example HPV6, 11, 16, 18); Influenza virus (whole live or inactivated virus, split influenza virus, grown in eggs or MDCK cells, or Vero cells or whole flu virosomes (as described by Gluck, Vaccine, 1992, 10, 915-920) or purified or recombinant proteins thereof, such as NP, NA, HA, or M proteins); measles virus; mumps virus; parainfluenza virus; rabies virus; Respiratory Syncytial virus (such as F and G proteins); rotavirus (including live attenuated viruses); smallpox virus; Varicella Zoster Virus (such as gpI, II and 1E63); and the HPV viruses responsible for cervical cancer (for example the early proteins E6 or E7 in fusion with a protein D carrier to form Protein D-E6 or E7 fusions from HPV 16, or combinations thereof; or combinations of E6 or E7 with L2 (see for example WO 96/26277).

Bacterial antigens or antigenic determinants can be derived from, for example: *Bacillus* spp., including *B. anthracis* (eg botulinum toxin); *Bordetella* spp, including *B. pertussis* (for example pertactin, pertussis toxin, filamenteous hemagglutinin, adenylate cyclase, fimbriae); *Borrelia* spp., including *B. burgdorferi* (eg OspA, OspC, DbpA, DbpB), *B. garinii* (eg OspA, OspC, DbpA, DbpB), *B. afzelii* (eg OspA, OspC, DbpA, DbpB), *B. andersonii* (eg OspA, OspC, DbpA, DbpB), *B. hermsii*; *Campylobacter* spp, including *C. jejuni*

(for example toxins, adhesins and invasins) and *C. coli; Chlamydia* spp., including *C. trachomatis* (eg MOMP, heparin-binding proteins), *C. pneumonie* (eg MOMP, heparin-binding proteins), *C. psittaci; Clostridium* spp., including *C. tetani* (such as tetanus toxin), *C. botulinum* (for example botulinum toxin), *C. difficile* (eg *clostridium* toxins A or B); *Corynebacterium* spp., including *C. diphtheriae* (eg diphtheria toxin); *Ehrlichia* spp., including *E. equi* and the agent of the Human Granulocytic Ehrlichiosis; *Rickettsia* spp, including *R. rickettsii; Enterococcus* spp., including *E. faecalis, E. faecium; Escherichia* spp, including enterotoxic *E. coli* (for example colonization factors, heat-labile toxin or derivatives thereof, or heat-stable toxin), enterohemorragic *E. coli*, enteropathogenic *E. coli* (for example shiga toxin-like toxin); *Haemophilus* spp., including *H. influenzae* type B (eg PRP), non-typable *H. influenzae*, for example OMP26, high molecular weight adhesins, P5, P6, protein D and lipoprotein D, and fimbrin and fimbrin derived peptides (see for example U.S. Pat. No. 5,843,464); *Helicobacter* spp., including *H. pylori* (for example urease, catalase, vacuolating toxin); *Pseudomonas* spp, including *P. aeruginosa; Legionella* spp, including *L. pneumophila; Leptospira* spp., including *L. interrogans; Listeria* spp., including *L. monocytogenes; Moraxella* spp, including *M. catarrhalis*, also known as *Branhamella catarrhalis* (for example high and low molecular weight adhesins and invasins); *Morexella Catarrhalis* (including outer membrane vesicles thereof, and OMP106 (see for example W097/41731)); *Mycobacterium* spp., including *M. tuberculosis* (for example ESAT6, Antigen 85A, -B or -C), *M. bovis, M. leprae, M. avium, M. paratuberculosis, M. smegmatis; Neisseria* spp, including *N. gonorrhea* and *N. meningitidis* (for example capsular polysaccharides and conjugates thereof, transferrin-binding proteins, lactoferrin binding proteins, PilC, adhesins); *Neisseria mengitidis* B (including outer membrane vesicles thereof, and NspA (see for example WO 96/29412); *Salmonella* spp, including *S. typhi, S. paratyphi, S. choleraesuis, S. enteritidis; Shigella* spp, including *S. sonnei, S. dysenteriae, S. flexnerii; Staphylococcus* spp., including *S. aureus, S. epidermidis; Streptococcus* spp, including *S. pneumonie* (eg capsular polysaccharides and conjugates thereof, PsaA, PspA, streptolysin, choline-binding proteins) and the protein antigen Pneumolysin (Biochem Biophys Acta, 1989, 67, 1007; Rubins et al., Microbial Pathogenesis, 25, 337-342), and mutant detoxified derivatives thereof (see for example WO 90/06951; WO 99/03884); *Treponema* spp., including *T. pallidum* (eg the outer membrane proteins), *T. denticola, T. hyodysenteriae; Vibrio* spp, including *V. cholera* (for example cholera toxin); and *Yersinia* spp, including *Y. enterocolitica* (for example a Yop protein), *Y. pestis, Y. pseudotuberculosis*.

Parasitic/fungal antigens or antigenic determinants can be derived from, for example: *Babesia* spp., including *B. microti; Candida* spp., including *C. albicans; Cryptococcus* spp., including *C. neoformans; Entamoeba* spp., including *E. histolytica; Giardia* spp., including; *G. lamblia; Leshmania* spp., including *L. major; Plasmodium. faciparum* (MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27/25, Pfs16, Pfs48/45, Pfs230 and their analogues in *Plasmodium* spp.); *Pneumocystis* spp., including *P. carinii; Schisostoma* spp., including *S. mansoni; Trichomonas* spp., including *T. vaginalis; Toxoplasma* spp., including *T. gondii* (for example SAG2, SAG3, Tg34); *Trypanosoma* spp., including *T. cruzi*.

It will be appreciated that in accordance with this aspect of the present invention antigens and antigenic determinants can be used in many different forms. For example, antigens or antigenic determinants can be present as isolated proteins or peptides (for example in so-called "subunit vaccines") or, for example, as cell-associated or virus-associated antigens or antigenic determinants (for example in either live or killed pathogen strains). Live pathogens will preferably be attenuated in known manner. Alternatively, antigens or antigenic determinants may be generated in situ in the subject by use of a polynucleotide coding for an antigen or antigenic determinant (as in so-called "DNA vaccination"), although it will be appreciated that the polynucleotides which can be used with this approach are not limited to DNA, and may also include RNA and modified polynucleotides as discussed above.

In one embodiment, a vaccine antigen can also be targeted, for example to particular cell types or to particular tissues. For example, the vaccine antigen can be targeted to Antigen Presenting Cells (APCs), for example by use of agents such as antibodies targeted to APC-surface receptors such as DEC-205, for example as discussed in WO 2009/061996 (Celldex Therapeutics, Inc), or the Mannose Receptor (CD206) for example as discussed in WO 03040169 (Medarex, Inc.).

For use in therapy, the antibodies of the invention can be administered to a subject directly (i.e., in vivo), either alone or with other therapies such as an immunostimulatory agent, a vaccine, chemotherapy or radiation therapy. In all cases, the antibodies, bispecifics, compositions, and immunostimulatory agents and other therapies are administered in an effective amount to exert their desired therapeutic effect. The term "effective amount" refers to that amount necessary or sufficient to realize a desired biologic effect. For example, an effective amount could be that amount necessary to eliminate a tumor, cancer, or bacterial, viral or fungal infection. The effective amount for any particular application can vary depending on such factors as the disease or condition being treated, the particular antibody being administered, the size of the subject, or the severity of the disease or condition. One of ordinary skill in the art can empirically determine the effective amount of a particular molecule without necessitating undue experimentation.

Preferred routes of administration for vaccines include, for example, injection (e.g., subcutaneous, intravenous, parenteral, intraperitoneal, intrathecal). The injection can be in a bolus or a continuous infusion. Other routes of administration include oral administration.

Antibodies and bispecific molecules of the invention also can be coadministered with adjuvants and other therapeutic agents. It will be appreciated that the term "coadministered" as used herein includes any or all of simultaneous, separate, or sequential administration of the antibodies and conjugates of the present invention with adjuvants and other agents, including administration as part of a dosing regimen. The antibodies are typically formulated in a carrier alone or in combination with such agents. Examples of such carriers include solutions, solvents, dispersion media, delay agents, emulsions and the like. The use of such media for pharmaceutically active substances is well known in the art. Any other conventional carrier suitable for use with the molecules falls within the scope of the instant invention.

Suitable agents for co-administration with the antibodies, conjugates, bispecifics, and compositions include other antibodies, cytotoxins and/or drugs, as well as adjuvants, immunostimulatory agents and/or immunosuppressive agents. In one embodiment, the agent is a chemotherapeutic agent. The antibodies, bispecifics, and compositions can be administered in combination with radiation.

Chemotherapeutic agents suitable for coadministration with the antibodies and conjugates of the present invention in the treatment of tumors include, for example: taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Further agents include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine) and temozolomide.

Agents that delete or inhibit immunosuppressive activities, for example, by immune cells (for example regulatory T-cells, NKT cells, macrophages, myeloid-derived suppressor cells, immature or suppressive dendritic cells) or suppressive factors produced by the tumor or host cells in the local microenvironment of the tumor (for example, TGFbeta, indoleamine 2,3 dioxygenase—IDO), may also be administered with the antibodies and conjugates of the present invention. Such agents include antibodies and small molecule drugs such as IDO inhibitors such as 1 methyl tryptophan or derivatives.

Suitable agents for coadministration with the antibodies and bispecifics of the present invention for treatment of such immune disorders include for example, immunosuppressive agents such as rapamycin, cyclosporin and FK506; anti-TNFa agents such as etanercept, adalimumab and infliximab; and steroids. Examples of specific natural and synthetic steroids include, for example: aldosterone, beclomethasone, betamethasone, budesonide, cloprednol, cortisone, cortivazol, deoxycortone, desonide, desoximetasone, dexamethasone, difluorocortolone, fluclorolone, flumethasone, flunisolide, fluocinolone, fluocinonide, fluocortin butyl, fluorocortisone, fluorocortolone, fluorometholone, flurandrenolone, fluticasone, halcinonide, hydrocortisone, icomethasone, meprednisone, methylprednisolone, paramethasone, prednisolone, prednisone, tixocortol and triamcinolone.

Suitable agents for coadministration with the antibodies and bispecifics of the present invention for inducement or enhancement of an immune response include, for example, adjuvants and/or immunostimulatory agents, non-limiting examples of which have been disclosed hereinbefore. A preferred immunostimulatory agent is a TLR3 agonist, such as Poly IC.

The present invention is further illustrated by the following examples which should not be construed as further limiting. The contents of Sequence Listing, figures and all references, patents and published patent applications cited throughout this application are expressly incorporated herein by reference.

EXAMPLES

Example 1

Generation of CD27-Specific Human Monoclonal Antibodies

Human anti-CD27 monoclonal antibodies were generated by immunizing the HC2/KCo7 strain of HuMAb® transgenic mice ("HuMAb" is a Trade Mark of Medarex, Inc., Princeton, N.J.) with a soluble human CD27 antigen. HC2/KCo7 HuMAb mice were generated as described in U.S. Pat. Nos. 5,770,429 and 5,545,806, the entire disclosures of which are hereby incorporated by reference.

Antigen and Immunization: The antigen was a soluble fusion protein comprising a CD27 extracellular domain fused with an antibody Fc domain (recombinant human CD27-Fc chimeric protein (R&D Systems). The antigen was mixed with Complete Freund's (Sigma) adjuvant for the first immunization. Thereafter, the antigen was mixed with Incomplete Freund's (Sigma). Additional mice were immunized with the soluble CD27 protein in RIBI MPL plus TDM adjuvant system (Sigma). 5-25 micrograms soluble recombinant CD27 antigen in PBS or $5 \times 10^6$ CHO cells transfected for surface expression of human CD27 in PBS were mixed 1:1 with the adjuvant. Mice were injected with 100 microliters of the prepared antigen into the peritoneal cavity every 14 days. Animals that developed anti-CD27 titers were given an iv injection of 10 micrograms soluble recombinant CD27 antigen three to four days prior to fusion. Mouse spleens were harvested, and the isolated splenocytes used for hybridoma preparation.

Hybridoma Preparation: The P3×63Ag8.653 murine myeloma cell line (ATCC CRL 1580) was used for the fusions. RPMI 1640 (Invitrogen) containing 10% FBS, and was used to culture the myeloma cells. Additional media supplements were added to the Hybridoma growth media, which included: 3% Origen-Hybridoma Cloning Factor (Igen), 10% FBS (Sigma), L-glutamine (Gibco) 0.1% gentamycin (Gibco), 2-mercaptoethanol (Gibco), HAT (Sigma; $1.0 \times 10^4$ M hypoxanthine, $4.0 \times 10^{-7}$ M aminopterin, $1.6 \times 10^{-5}$ M thymidine), or HT (Sigma; $1.0 \times 10^{-4}$ M hypoxanthine, $1.6 \times 10^{-5}$ M thymidine) media.

Spleen cells were mixed with the P3×63Ag8.653 myeloma cells in a 6:1 ratio and pelleted by centrifugation. Polyethylene glycol was added dropwise with careful mixing to facilitate fusion. Hybridomas were allowed to grow out for one to two weeks until visible colonies become established. Supernatant was harvested and used for initial screening for human IgG via ELISA using a human kappa chain specific capture and a human Fc specific detection. IgG positive supernatants were then assayed for CD27 specificity via flow cytometry or using a ELISA to detect anti-CD27.

Hybridomas producing specific human monoclonal antibodies (human mAbs; IgG) were subcloned and expanded. The human mAbs produced were then purified by protein A column chromatography according to standard conditions which led to the isolation of a number of antibodies of particular interest, which were designated as 4B7-1B3 (also referred to herein as 4B7), 3H12-1C8 (also referred to herein as 3H12), 1F5-1H5 (also referred to herein as 1F5), 2C2-1A10 (also referred to herein as 2C2), 2G9-1D11 (also referred to herein as 2G9), 1H8-B4 (also referred to herein as 1H8), 3H12-1E12 (also referred to herein as 3H12), 3G1-1A11 (also referred to herein as 3G1) (1B10), 4A2-B11 (also referred to herein as 4A2), 3A10-G10 (also referred to herein as 3A10), 2G11-B5 (also referred to herein as 2G11), 4H11-G11 (also referred to herein as 4H11), 2H3-E8 (also referred to herein as 2H3), 4A7-B3 (also referred to herein as 4A7), 3H8-1B11 (also referred to herein as 3H8) and 1G5-1B9 (also referred to herein as 1G5).

The hybridomas were also screened for cross-reactivity with rhesus macaque CD27 and all were positive for binding.

Example 2

Determination of Affinity and Rate Constants of Human mAbs by Surface Plasmon Resonance (SPR)

Binding affinity and binding kinetics of various human anti-CD27 antibodies from Example 1 were examined by Biacore™ surface plasmon resonance (SPR) analysis using a Biacore™ 2000 SPR instrument (Biacore AB, Uppsala, Sweden) according to the manufacturer's guidelines.

Purified recombinant human CD27/TNFRSF7/Fc chimera (R&D Systems Catalog No. 382-CD) protein was covalently linked to a Biacore™ CM5 sensor chip (carboxymethylated dextran covalently attached to a gold surface; Biacore Product No. BR-1000-14) using standard amine coupling chemistry with an Amine Coupling Kit provided by Biacore according to the manufacturer's guidelines (BIAcore Product No. BR-1000-50, comprising coupling reagents N-hydroxysuccinimide (NHS) and 1-Ethyl-3-(3-dimethylaminopropyl) carbodiimide hydrochloride (EDC)). Low levels of ligand were immobilised to limit any effects of mass transport of analyte on kinetic parameters, such that the $R_{MAX}$ observed was in the order of 100-400 RU.

Binding was measured by flowing the antibodies over the sensor chip in HBS-EP buffer (HBS-EP buffer, Biacore Product No. BR-1001-88: 4-(2-hydroxyethyl)-1-piperazineethanesulfonic acid (HEPES) 0.01M, sodium chloride 0.15M ethylenediaminetetraacetic acid (EDTA) 3 mM, Surfactant P20 0.005%), at concentrations ranging from 1.56 to 50 nM and at a flow rate of 30 μl/minute for 180 seconds. The antigen-antibody association and dissociation kinetics were followed for either 480 seconds or 1200 seconds for antibodies with slower dissociation rates.

Corresponding controls were conducted in each case using a blank flowcell with no protein immobilized for "background" subtraction. Sequential injections of 10 mM HCl for 10 seconds at 50 μl/min followed by 10 mM Glycine pH 2.0 for 30 seconds at 50 μl/min was used as the regeneration conditions throughout the study.

Biacore's BIAevaluation software version 3.2 (Biacore AB, Uppsala, Sweden) was used in each case to derive kinetic parameters from the concentration series of analyte diluted in HBS-EP running buffer. The association and dissociation curves were fitted to a 1:1 Langmuir binding model using Biacore™ BIAevaluation software (Biacore AB) according to the manufacturer's guidelines.

The affinity and kinetic parameters (with background subtracted) as determined are shown in FIG. 1.

For each antibody, the figures shown are the mean of two separate series of experiments, using separately prepared flow cells in each case, (where ka=rate constant of association, kd=rate constant of dissociation, $K_D$=dissociation equilibrium constant (measure of affinity), $K_A$=association equilibrium constant, Rmax=maximum SPR response signal).

Example 3

ELISA Assay to Determine Human mAb Binding Characteristics on CD27

Microtiter plates were coated with soluble or recombinant human or macaque CD27 in PBS, and then blocked with 5% bovine serum albumin in PBS. Protein A purified human mAbs and an isotype control were added at saturating concentrations and incubated at 37° C. The plates were washed with PBS/Tween and then incubated with a goat-anti-human IgG Fc-specific polyclonal reagent conjugated to alkaline phosphatase at 37° C. After washing, the plates were developed with pNPP substrate (1 mg/ml), and analyzed at OD 405-650 using a microtiter plate reader. Representatives binding curves are shown in FIG. 2. The results were also used to estimate the 50% saturating concentration (C value in 4-parameter fit curve) as shown in Table 1 below.

Figure 3:
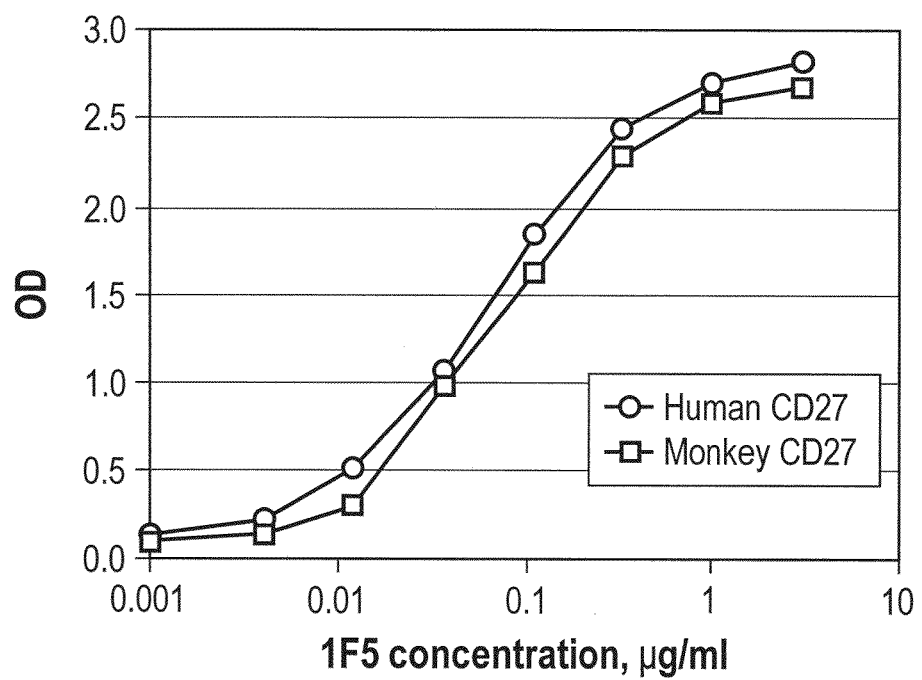
FIG. 3 is a graph showing binding by ELISA of 1F5 to purified recombinant human or monkey (macaque) CD27.

To establish that cynomolgus macques are a relevant model for testing anti-CD27 mAbs, various concentrations of purified macaque CD27 or human CD27 were captured to ELISA plates with anti-Flag antibody, followed by incubation with anti-human CD27 mAb. A goat anti-human IgG Fc-HRP antibody and substrate Super Blue TMB were used for detection. Results are shown in Table 1, which indicate similar binding to CD27 from macque and human. Representative binding curves for antibody 1F5 are also shown in FIG. 3.

TABLE 1

Characterization of selected anti-CD27 mAb

| mAb | Half-max binding to human CD27(M)** | Half-max binding to human CD27(μg/ml)** | Half-max binding to monkey CD27(μg/ml)** |
|---|---|---|---|
| 1G5 | 4.9E−10 | 0.074 | 0.065 |
| 1H8 | 4.3E−10 | 0.064 | 0.105 |
| 3H12 | 5.7E−10 | 0.085 | 0.123 |
| 3H8 | 4.6E−10 | 0.069 | 0.065 |
| 2G9 | 4.3E−10 | 0.064 | 0.069 |
| 1F5 | 3.9E−10 | 0.059 | 0.12 |
| 3A10 | 6.3E−10 | 0.094 | no binding |
| 2C2 | 3.0E−10 | 0.045 | 0.034 |

**estimated by binding to CD27 coated plates in an ELISA format

In a further experiment, to establish similar distribution of 1F5 binding to peripheral blood cells, PBMCs were isolated from whole blood of 3 humans and 3 cynomolgus macaques. The cells were stained with 1F5 mAb together with markers to delineate the major T cell and B cell populations that express CD27. The following table (Table 2) summarizes the mean±standard error of results for human and macaque cells with respect to the percent of cells expressing CD27 and the intensity of expression (MFI). These data establish a similar distribution of 1F5 binding to peripheral blood cells from human and monkey.

TABLE 2

| Analysis | CD4+ T cells | | CD8+T cells | | B cells (CD20+) | | NK cells | |
|---|---|---|---|---|---|---|---|---|
| | human | monkey | human | monkey | human | monkey | human | monkey |
| % CD27+[b] | 84 ± 5 | 81 ± 1 | 70 ± 12 | 90 ± 1 | 37 ± 4 | 15 ± 1 | 11 ± 4 | 88 ± 6 |
| MFI[c] | 1517 ± 123 | 416 ± 14 | 1415 ± 153 | 519 ± 11 | 893 ± 101 | 491 ± 113 | 667 ± 28 | 1050 ± 42 |

Example 4

4A: Blocking of sCD70 Binding by ELISA

Figure 4:
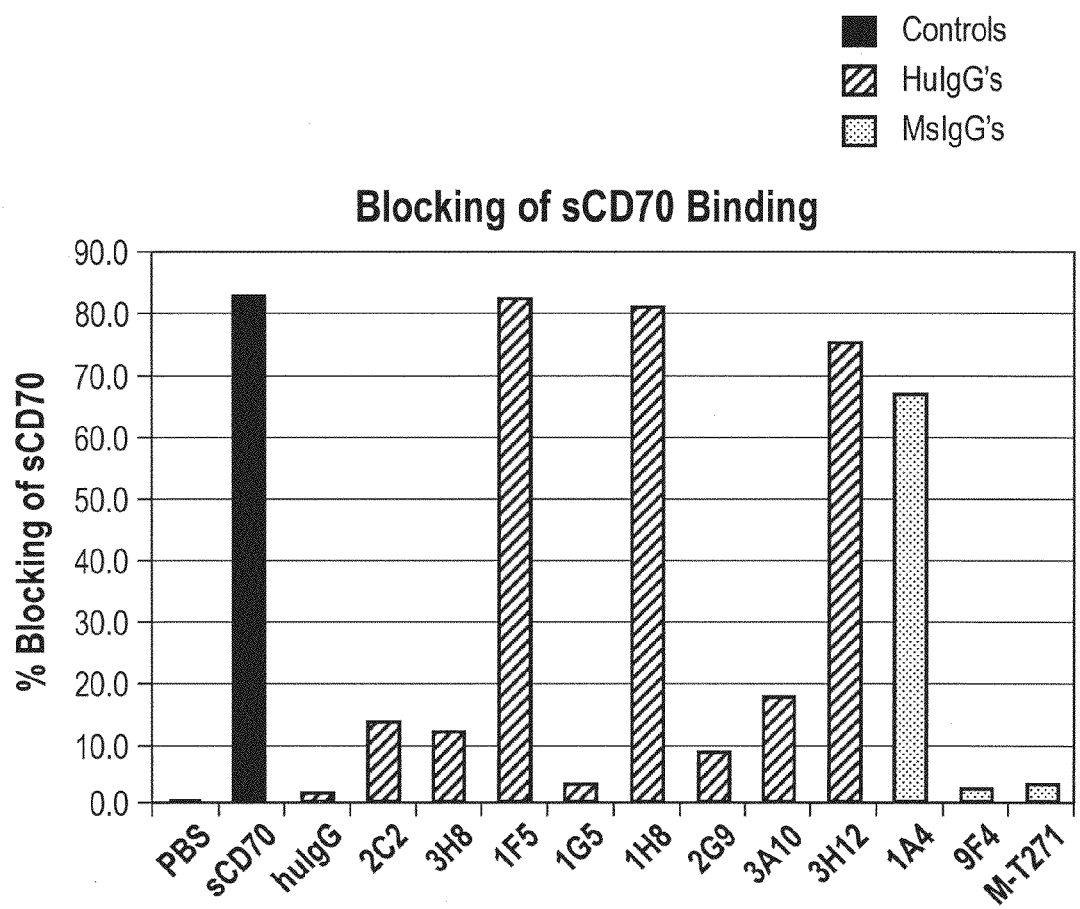
FIG. 4 is a graph depicting the effect of human anti-CD27 antibodies (2C2, 3H8, 1F5, 1G5, 1H8, 2G9, 3A10 and 3H12) and MsIgG's (1A4, 9F4, and M-T271) on the binding of soluble CD70 (sCD70) to CD27 protein (shown as % blocking) by ELISA.

The effect of the human mAbs from Example 1 on the binding of soluble CD70 (sCD70) to CD27 protein was measured by ELISA. A microtiter plate was coated with 1 μg/ml soluble recombinant human CD27/Fc chimera from R&D Systems at 1 μg/mL., then blocked with 5% PBA. The anti-CD27 antibodies ([final]=25 μg/mL) were premixed with soluble human recombinant CD70-biotin from US Biologicals ([final]=0.5 μg/mL) and added to the plate. CD27-captured rCD70 was detected with streptavidin-HRP and substrate Super Blue TMB. The results (shown as % blocking) are shown in FIG. 4 with controls as indicated. These results show that several of the antibodies (including 1F5, 1H8, 3H12 and 1A4) had the property of blocking or at least significantly inhibiting the binding of sCD70.

Figure 5:
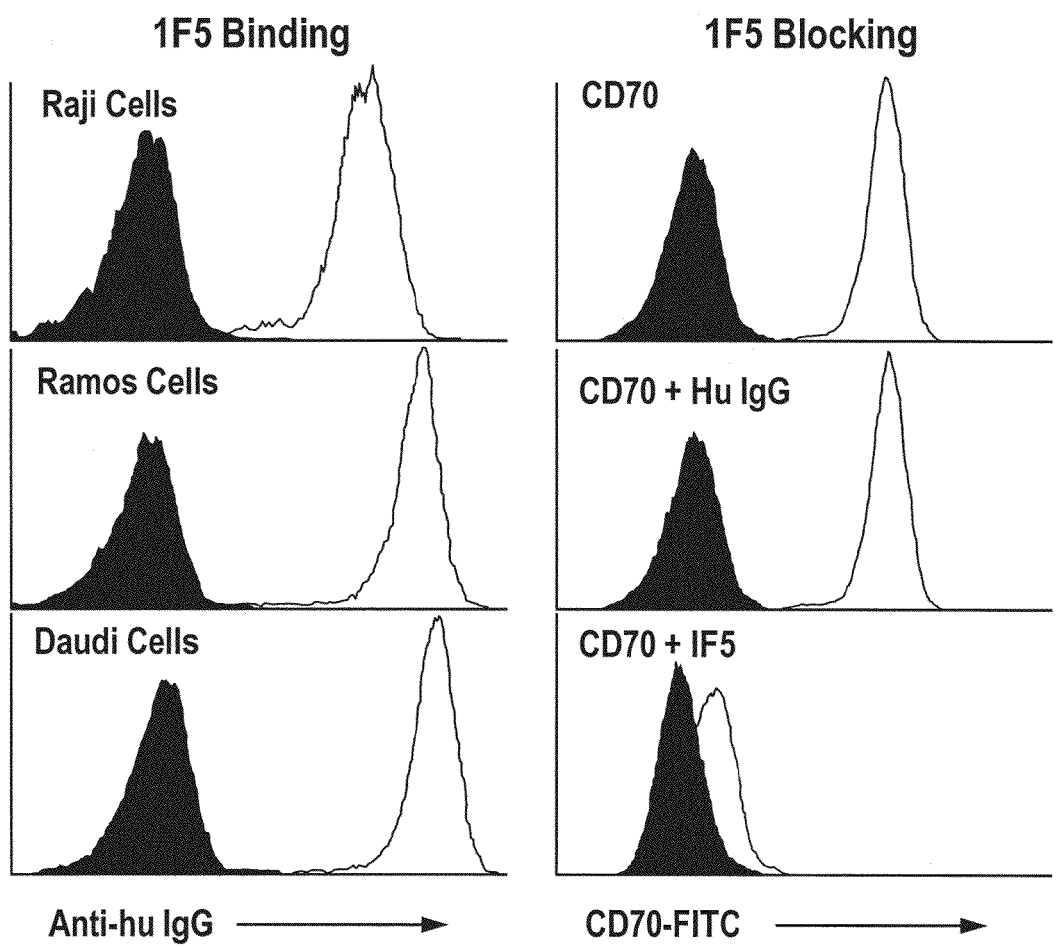
FIG. 5 is a flow cytometric analysis of 1F5 binding to human lymphoblastoid cell lines, and blocking of sCD70 binding.
Figure 6A:
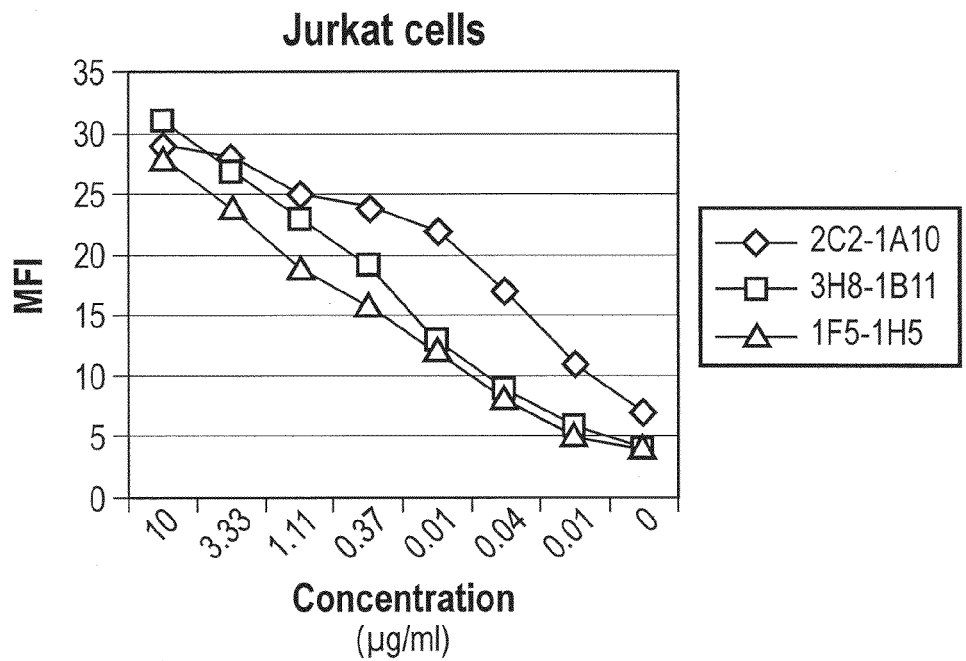
FIGS. 6A-D are graphs showing the binding of human anti-CD27 antibodies (2C2, 3H8, and 1F5) to CD27 on Jurkat cells (FIG. 4A), Raji cells (FIG. 4B), Ramos cells (FIG. 4C), and Daudi cells (FIG. 4D) as assessed by flow cytometry.
Figure 6B:
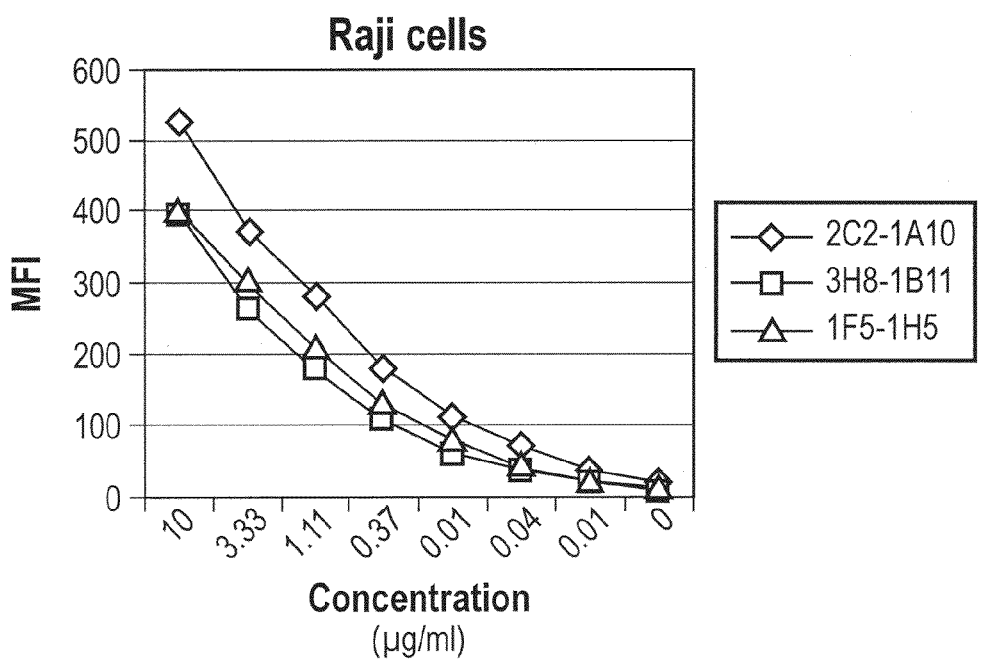
Figure 6C:
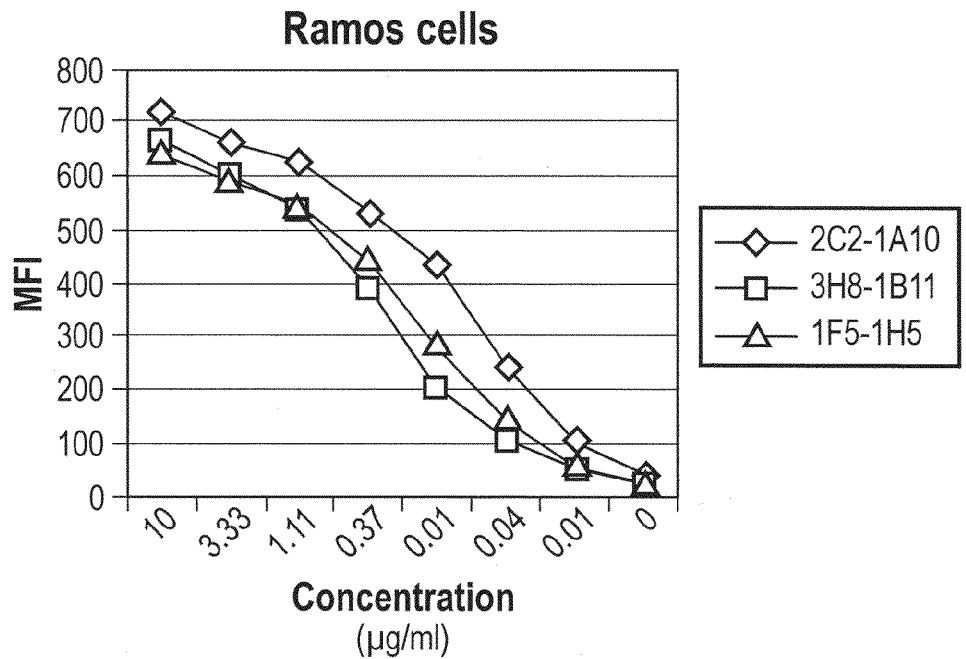
Figure 6D:
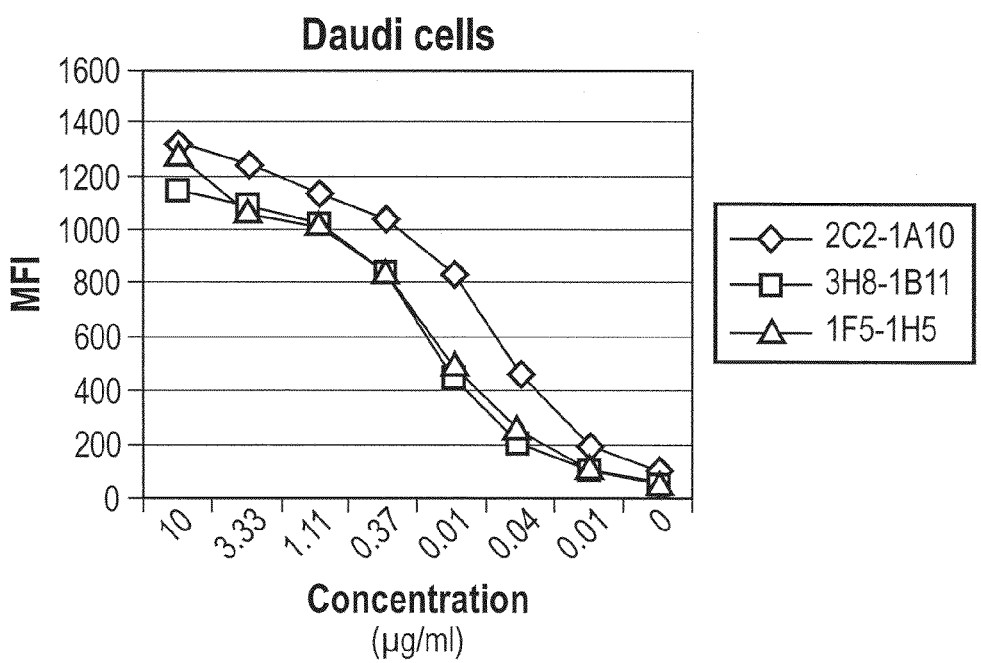

4B: CD27 mAb Binds to CD27 on Human Lymphoblastoid Cell Lines and Blocks Ligand (CD70) Binding Binding of anti-human CD27 mAb 1F5 to human lymphoblastoid cell lines, and blocking of sCD70 binding, was analysed by flow cytometry using a Becton Dickinson FACSCanto II flow cytometer. The results are shown in FIG. 5, and show that 1F5 effectively binds to a variety of cell lines and competitively inhibits binding of sCD70.

Example 5

Binding of Human mAbs to Cells Expressing Human CD27

The ability of anti-CD27 human mAbs to bind to CD27 on cells expressing human CD27 on their surface was investigated by flow cytometry as follows.

Antibodies were tested for binding to human cell lines expressing human D27 on their surface. Protein A purified human mAbs 2C2, 3H8 and 1F5 were incubated with Jurkat, Raji, Ramos and Daudi cells expressing human CD27, as well as control cells at 4° C. All antibodies were used at saturating concentrations. After 1 hour, the cells were washed with PBS containing 0.1% BSA and 0.05% $NaN_3$ (PBA) and the bound antibodies were detected by incubating the cells with a PE labeled goat anti-human IgG Fc-specific probe, at 4° C. The excess probe was washed from the cells with PBA and the cell associated fluorescence was determined by analysis using a LSR™ instrument (BD Biosciences, NJ, USA) according to the manufacturer's directions.

Figure 7:
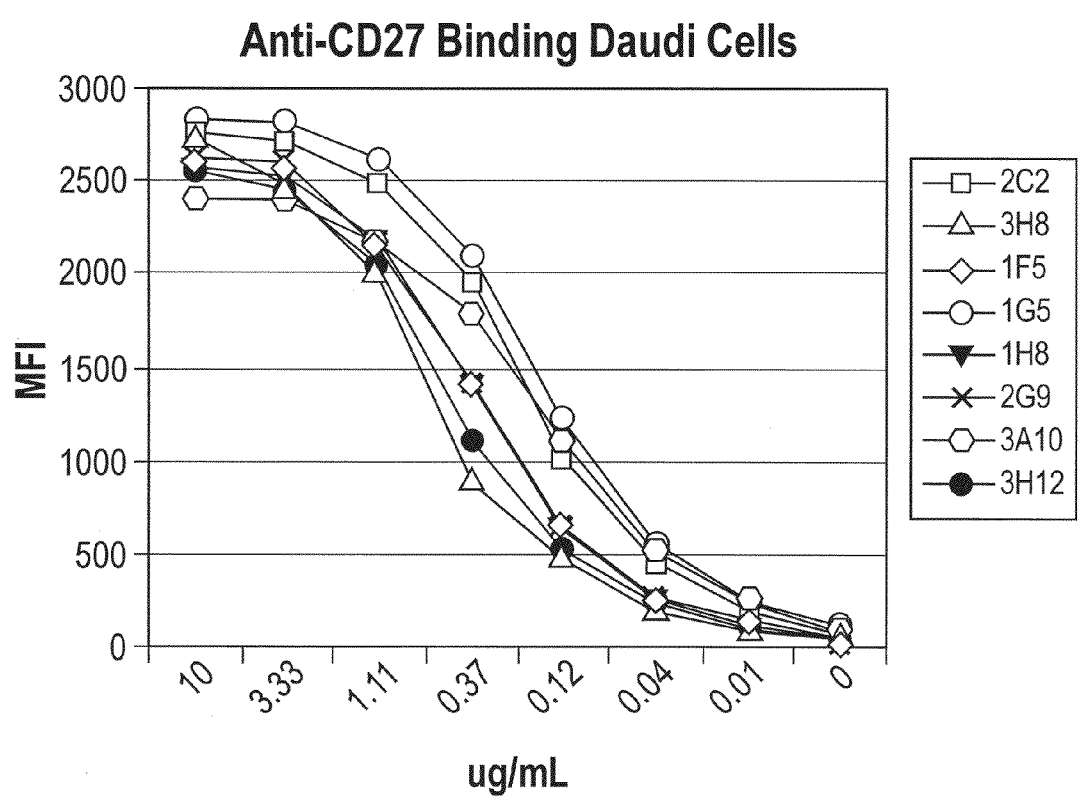
FIG. 7 is a graph showing the binding of human anti-CD27 antibodies (2C2, 3H8, 1F5, 1G5, 1H8, 2G9, 3A10 and 3H12) to CD27 on Daudi cells as assessed by flow cytometry.

As shown in FIGS. 6 and 7, the human mAbs demonstrated high level binding to cells expressing human CD27. These data demonstrate that these antibodies bind efficiently and specifically to human CD27 expressed on live cells compared to the control cells.

Example 6

Cross-Blocking/Competition of Human mAbs Determined by ELISA

Figure 8:
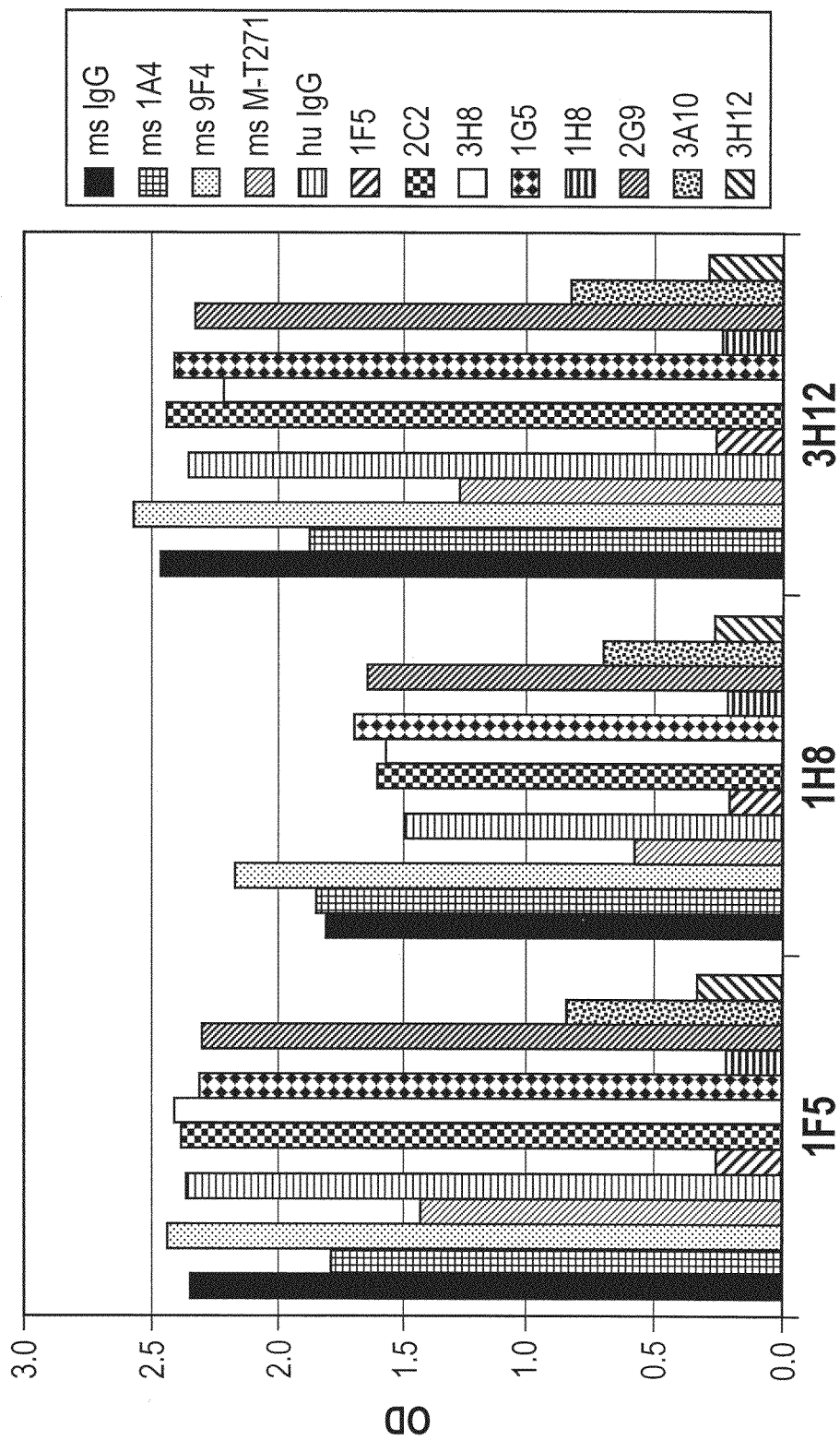
FIG. 8 is a bar graph showing the results of an anti-CD27 cross-blocking ELISA experiment, demonstrating that antibodies 1F5, 1H8 and 3H12 are capable of cross-blocking each other and thus bind to the same epitope.
Figure 9:
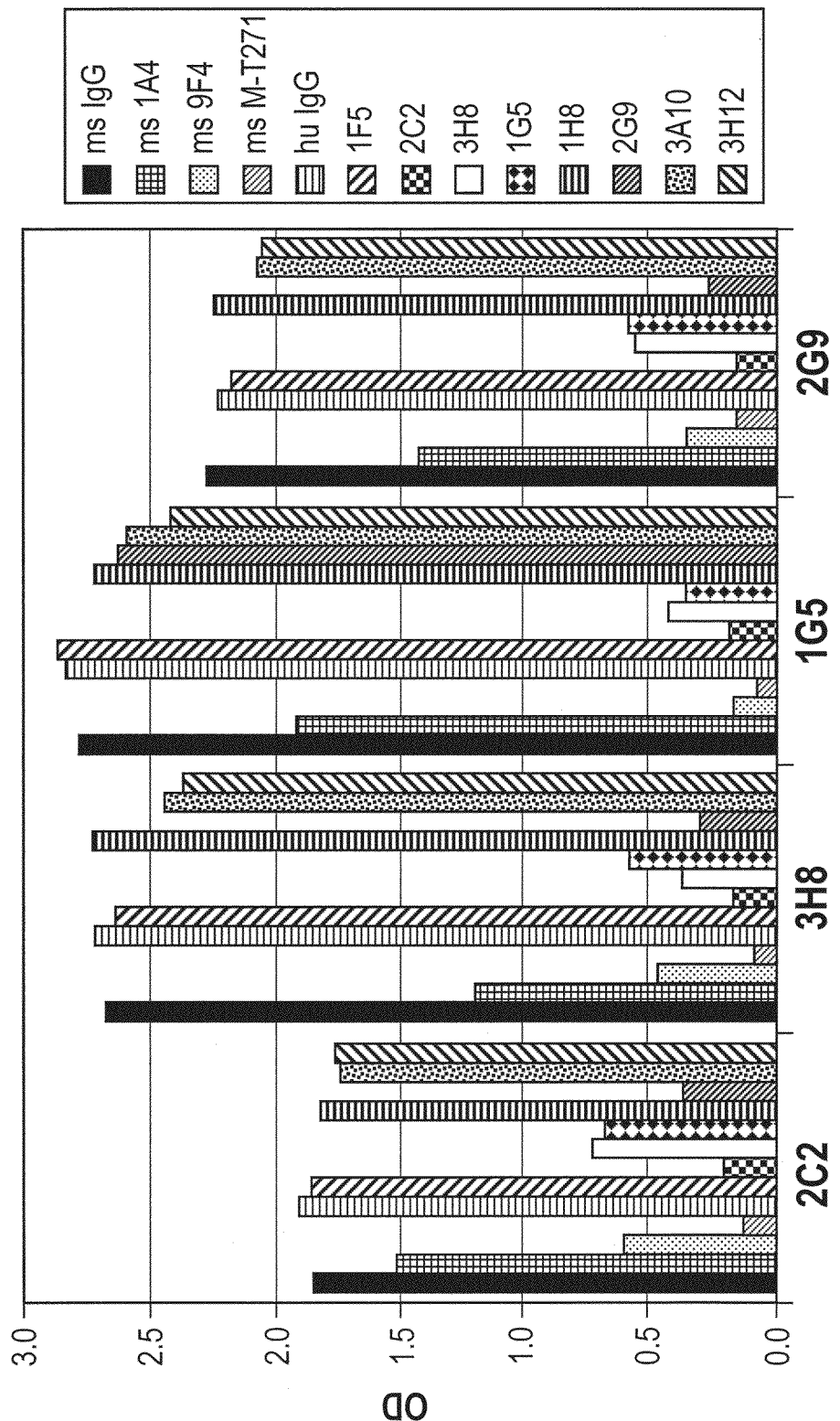
FIG. 9 is a bar graph showing the results of an anti-CD27 cross-blocking ELISA experiment, demonstrating that antibodies 2C2, 3H8, 1G5 and 2G9 are capable of cross-blocking each other and thus bind to the same epitope.
Figure 10:
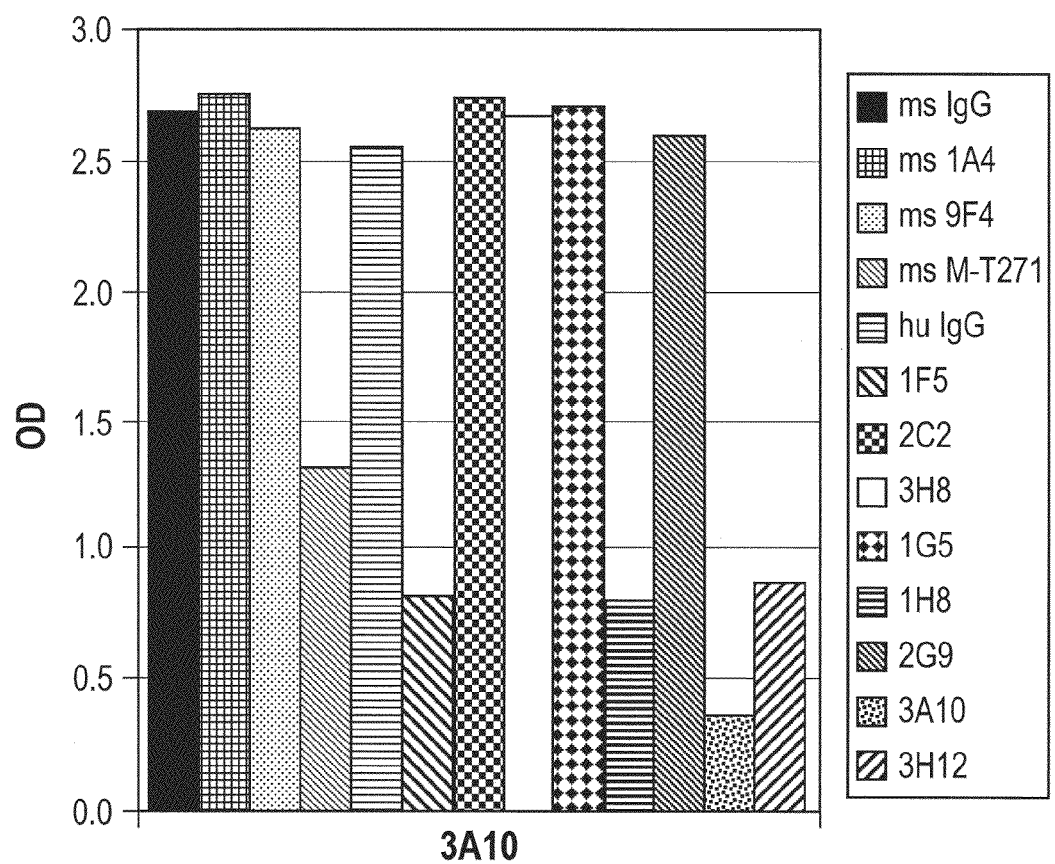
FIG. 10 is a bar graph showing the results of an anti-CD27 cross-blocking ELISA experiment, demonstrating that the binding of antibody 3A10 to CD27 is not fully cross-blocked by any of the other anti-CD27 antibodies tested, thus indicating that 3A10 binds a unique epitope, but 3A10 binding is partially cross-blocked by antibodies 1F5, 1H8 and 3H12, indicating that the epitope for 3A10 may be close to the epitope bound by antibodies 1F5, 1H8 and 3H12.

A microtiter plate was coated with a recombinant human CD27-Fc chimeric fusion protein, then blocked with 5% BSA in PBS. Unconjugated human mAbs (20 μg/mL) were mixed with horseradish peroxidase labeled secondary antibodies (0.5 μg/mL), then added to the plate and incubated at 37° C. The plates were washed with PBS/Tween and developed with TMB substrate and analyzed at OD 450 using a microtiter plate reader. The results, shown in FIGS. 8 to 10, indicate that a first set of the human mAbs (comprising mAbs 1F5, 1H8 and 3H12) cross-competed with each other (see FIG. 8), that a further set of the human mAbs (comprising mAbs 2C2, 3H8, 1G5, and 2G9) also cross-competed with each other (see FIG. 9), and that human mAb 3A10 binds a unique epitope but may bind at a site distinct from but possibly close to the binding sites of mAbs 1F5, 1H8, and 3H12 since these antibodies were able to partially cross-block the binding of 3A10 to CD27 (see FIG. 10).

Example 7

Complement Dependent Cellular Cytotoxicity (CDCC or CDC)

Figure 11:
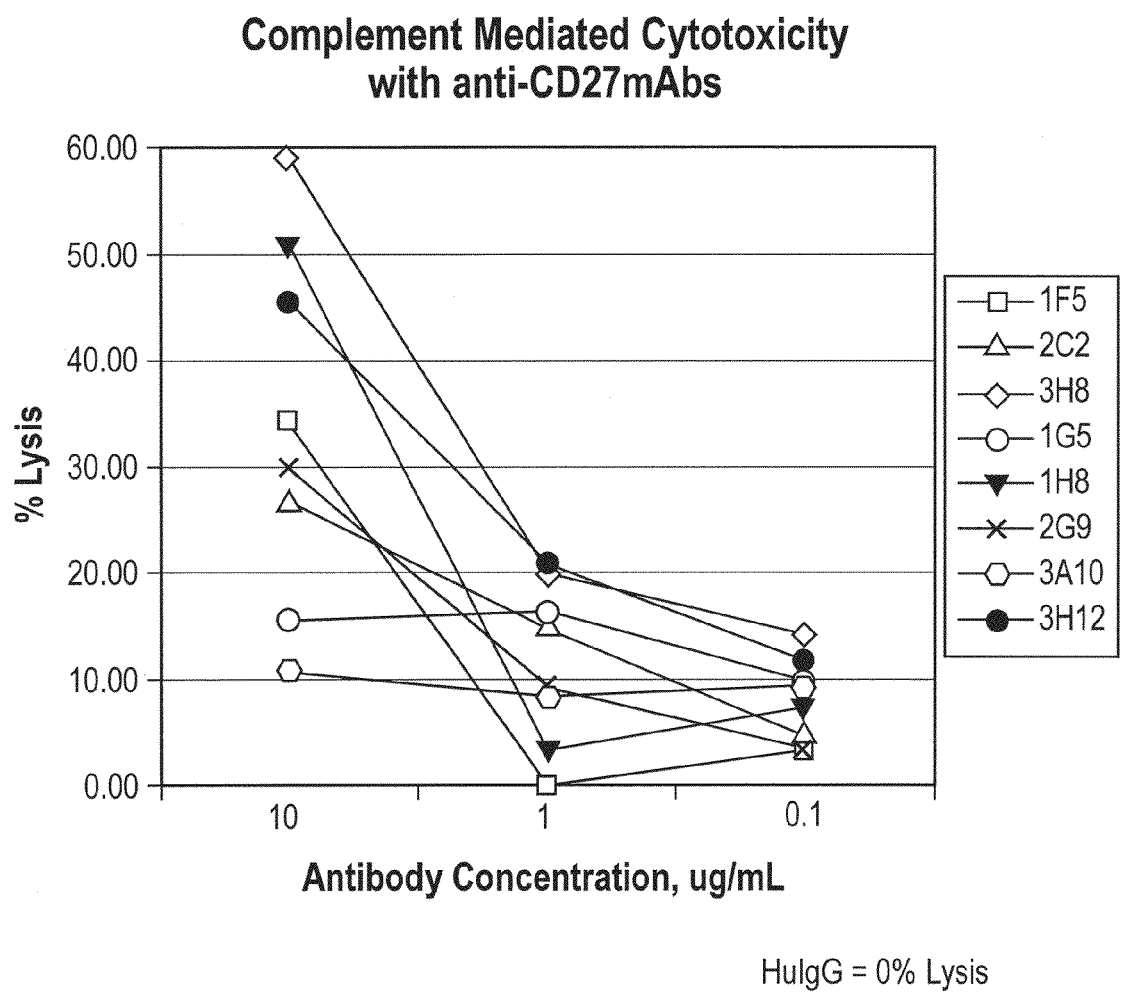
FIG. 11 is a graph depicting the results of a complement dependent cellular cytotoxicity (CDCC) assay using mAbs 1F5, 2C2, 3H8, 1G5, 1H8, 2G9, 3A10 and 3H12.

Target cells (Lymphoma Raji cells) were cultured (in AIM-V medium) for 1-2 hours at 37° C., 5% $CO_2$ in the presence of anti-CD27 antibodies and rabbit complement (final dilution of 1:15) in a final volume of 150 ul. Appropriate controls with a leak signal (targets only) and MAX signal (targets with Lysol™ detergent at 12% for a final concentration of 4%) were included as well. Cells were adjusted to $1\times10^6$/ml and 50 ul were added to each well (to give 50,000 cells/well). Wells were then resuspended and 100 ul of the cell suspension was transferred to an opaque, white plate. To each of these wells, 100 uL of Promega CellTiter Glo reagent was added and the plate was mixed for 2 minutes at room temperature. The plate was allowed to incubate for 10 minutes to stabilize the luminescent signal. Luminescence was recorded on a Perkin Elmer Victor X4 plate reader. Cytotoxicity was determined with the following formula: (100−((sample−MAX)/(leak−MAX)))×100. Results (shown as % lysis) are shown in FIG. 11 from which it can be seen that a number of the anti-CD27 antibodies displayed significant CDCC activity.

Figure 12:
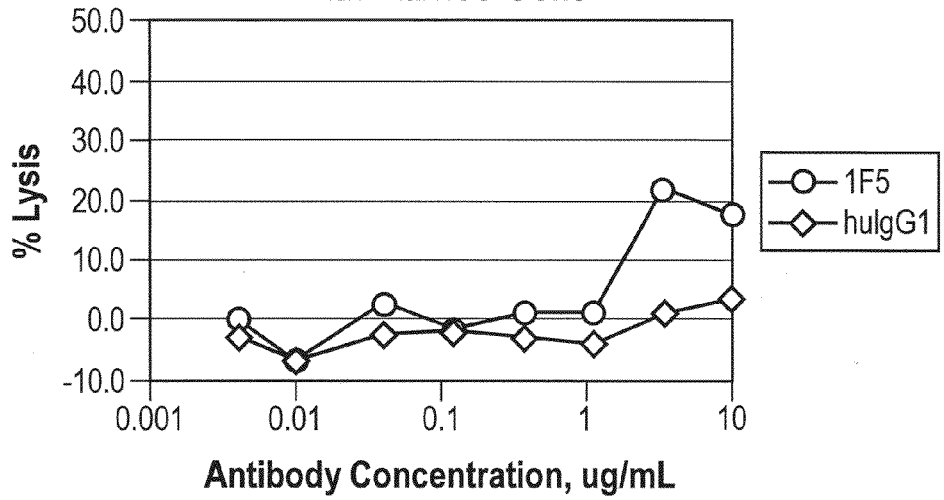
FIG. 12 is a graph depicting the results of a further complement dependent cellular cytotoxicity (CDCC) assay using mAb 1F5

In a further experiment, target cells (Ramos cells) were washed and loaded with Calcein AM (Molecular Probes). Loaded cells were then washed again and resuspended to $1\times10^6$/ml in culture media (RPMI+10% FBS). Target cells were cultured for 2 hours at 37° C., 5% $CO_2$ in the presence of anti-CD27 antibodies and rabbit complement (final dilution of 1:15) in a final volume of 150 ul. Appropriate controls with a leak signal (targets only) and MAX signal (targets with Triton X-100 at 20% for a final concentration of 2%) were included as well. Following the incubation, 75 ul of supernatant from the wells were transferred into an opaque, black plate. Fluorescence (Ex 485; Em 535) was recorded on a Perkin Elmer Victor X4 plate reader. Specific cytotoxicity was determined using the following formula: (experimental−spontaneous lysis)/(maximum lysis−spontaneous lysis)×100. The results, shown in FIG. 12, indicate that anti-CD27 mAb (1F5) showed at least 10% CDC activity in Ramos cells at an antibody concentration of 314/ml.

Example 8

Antibody Dependent Cell-Mediated Cytotoxicity (ADCC)

Figure 13:
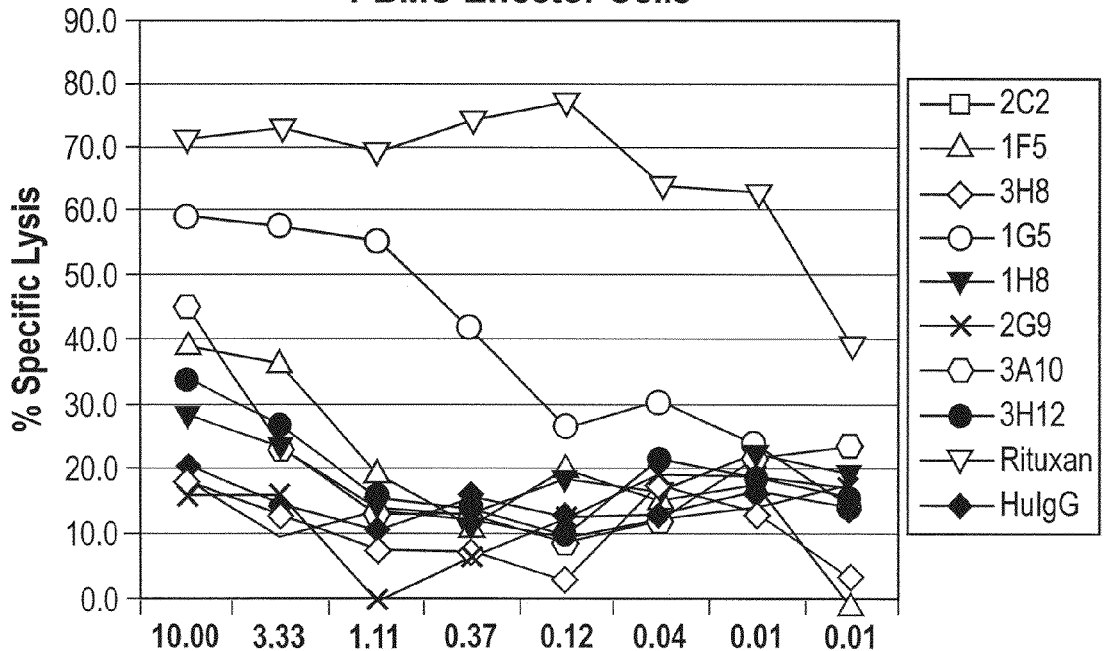
FIG. 13 is a graph depicting the results of an antibody dependent cell-mediated cytotoxicity (ADCC) assay using mAbs 2C2, 1F5, 3H8, 1G5, 1H8, 2G9, 3A10, 3H12, Rituxan and HuIgG.

Targets cells (Lymphoma Raji cells) were washed and loaded with BATDA reagent (Perkin Elmer). Loaded cells were then washed again and resuspended to $2\times10^5$/ml in culture media (RPMI+10% FBS). Effector cells were prepared and adjusted to appropriate concentrations in culture media to yield desired effector:target ratios (100:1-50:1). In a round bottom plate, target cells, effector cells and antibody were added in a final volume of 150 ul. Appropriate controls were used, including a leak signal (targets only), a spontaneous lysis signal (targets+effectors), and a maximum lysis signal (targets+Lysol™ detergent at 12% for a final concentration of 4%). Cells were pelleted in the plate and incubated for 2 hours at 37° C., 5% $CO_2$. Following the incubation, 20 ul of supernatant from the wells were transferred into an opaque, white plate. To each of these wells, 200 ul of Europium solution (Perkin Elmer) was added and the plate was mixed for 15 minutes. Time-resolved fluorescence was recorded on a Perkin Elmer Victor X4 plate reader. Specific cytotoxicity was determined using the following formula: (experimental−spontaneous lysis)/(maximum lysis−spontaneous lysis)×100. Results (shown as % lysis) are shown in FIG. 13 from which it can be seen that a number of the anti-CD27 antibodies displayed significant ADCC activity.

Figure 14:
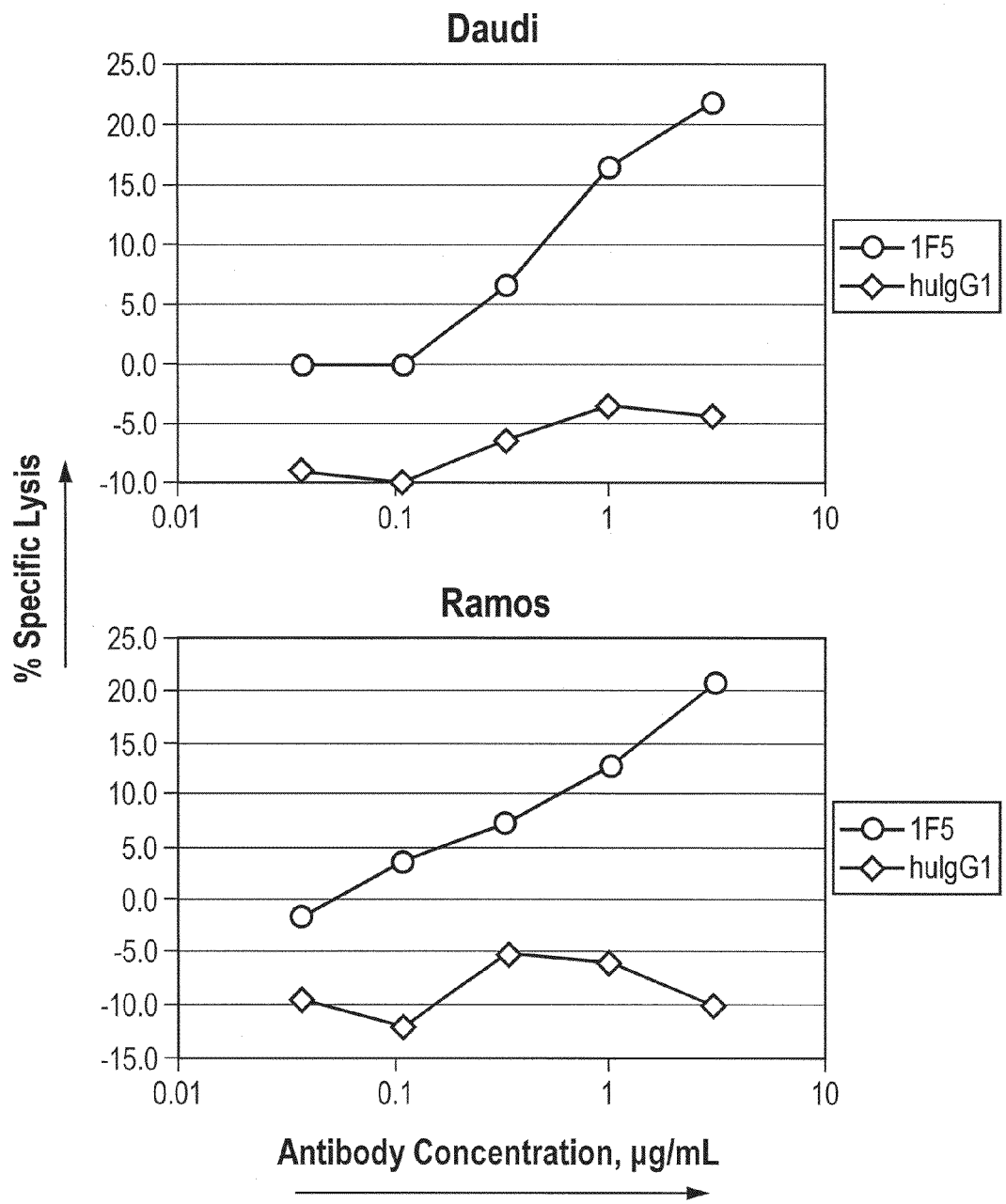
FIG. 14 is a graph depicting the results of a further antibody dependent cell-mediated cytotoxicity (ADCC) using mAb 1F5

In a further experiment, target cells (Lymphoma Ramos and Daudi cells) were washed and loaded with Calcein AM (Molecular Probes) Loaded cells were then washed again and resuspended to $1\times10^5$/ml in culture media (RPMI+10% FBS). Effector cells were prepared and adjusted to appropriate concentrations in culture media to yield desired effector: target ratios (75:1). In a round bottom plate, target cells, effector cells and antibody were added in a final volume of 150 ul. Appropriate controls were used, including a leak signal (targets only), a spontaneous lysis signal (targets+effectors), and a maximum lysis signal (targets+Triton X-100 at 20% for a final concentration of 2%). Cells were pelleted in the plate and incubated for 4 hours at 37° C., 5% $CO_2$. Following the incubation, 75 ul of supernatant from the wells were transferred into an opaque, black plate. Fluorescence (Ex 485; Em 535) was recorded on a Perkin Elmer Victor X4 plate reader. Specific cytotoxicity was determined using the following formula: (experimental−spontaneous lysis)/(maximum lysis−spontaneous lysis)×100. The results, shown in FIG. 14 indicate that anti-CD27 mAb (1F5) showed at least 10% ADCC activity (measured as specific cytotoxicity) in Daudi and Ramos cells at an antibody concentration of 3 μg/ml and ratio of effector:target cells of 75:1.

Example 9

Antibody Sequencing

As described above in Example 1, human mAbs from hybridomas producing specific human mAbs IgG were purified by protein A column chromatography which led to the isolation of a panel of antibodies (human mAbs) of particular interest. The $V_H$ and $V_L$ coding regions of human mAbs 4B7, 3H12, 1F5, 2C2, 2G9, 1H8, 3H12, 3G1 (1B10) 4A2, 3A10, 2G11, 4H11, 2H3, 4A7, 3H8 and 1G5 were identified using RNA from the corresponding hybridomas. RNA was reverse transcribed to cDNA, the V coding regions were amplified by PCR and the PCR product was sequenced. The following are the nucleic and amino acid sequences of the $V_H$ and $V_L$ regions of the human mAbs (in the case of the amino acid sequences, the Complementarity Determining Regions (CDRs) are underlined).

3H8 VH (VH 3-7; D7-27; JH2)
$V_H$ nucleic acid sequence (SEQ ID NO: 5)

```
atggagttggggctgagctgggttttccttgttgctattttagaaggtg tccagtgtgaggtgcagctggtggagtctgggggaggcttggtccagcc tggggggtccctgagactctcctgtgcagcctctggattcaccttagt agttattggatggcctgggtccgccaggctccagggaagggctggagt ggctgggcaatataaagcaagatggaagtgagaaatactatgtggactc tgtgaagggccgattcaccatctccagagacaacgccaagaactcactg tatctacaaatgaacagcctgagagccgaggacacggctgtgtattact
``` gtgtgagggaactggggatggactggtacttcgatctctggggccgtgg caccctggtcactgtctcctca $V_H$ amino acid sequence (SEQ ID NO: 6) (including signal peptide in underlined italics):

*MELGLSWVFLVAILEGVQC*EVQLVESGGGLVQPGGSLRLSCAASGFTF
SSYWMAWVRQAPGKGLEWLGNIKQDGSEKYYVDSVKGRFTISRDNAKN
SLYLQMNSLRAEDTAVYYCVRELGMDWYFDLWGRGTLVTVSS $V_H$ "mature" amino acid sequence (SEQ ID NO: 7) excluding signal peptide:

EVQLVESGGGLVQPGGSLRLSCAASGFTFSSYWMAWVRQAPGKGLEWL
GNIKQDGSEKYYVDSVKGRFTISRDNAKNSLYLQMNSLRAEDTAVYYC
VRELGMDWYFDLWGRGTLVTVSS $V_H$ CDR1 (SEQ ID NO: 8):        GFTFSSYW $V_H$ CDR2 (SEQ ID NO: 9):        IKQDGSEK $V_H$ CDR3 (SEQ ID NO: 10):       VRELGMDWYFDL

3H8 VK #2 (VK 3-11; JK1)
$V_L$ nucleic acid sequence (SEQ ID NO: 11)

```
Atggaagcccagctcagcttctcttcctcctgctactctggctccca gataccaccggagaaattgtgttgacacagtctccagccaccctgtct ttgtctccaggggaaagagccaccctctcctgcagggccagtcagagt gttgacagctacttagcctggtaccaacagaaacctggccaggctccc aggctcctcatctatgatgcatccaacagggccactggcatcccagcc aggttcagtggcagtgggtctgggacagacttcactctcaccatcagc aacctagagcctgaagattttgcagtttattactgtcagcagcgtagc aactggcctccgacgttcggccaagggaccaaggtggaaatcaaa
```

$V_L$ amino acid sequence (SEQ ID NO: 12) (including signal peptide in underlined italics):

*MEAPAQLLFLLLLWLPDTTG*EIVLTQSPATLSLSPGERATLSCRASQS
VDSYLAWYQQKPGQAPRLLIYDASNRATGIPARFSGSGSGTDFTLTIS
NLEPEDFAVYYCQQRSNWPPTFGQGTKVEIK $V_L$ amino acid sequence (SEQ ID NO: 13) excluding signal peptide:

EIVLTQSPATLSLSPGERATLSCRASQSVDSYLAWYQQKPGQAPRLLI
YDASNRATGIPARFSGSGSGTDFTLTISNLEPEDFAVYYCQQRSNWPP
TFGQGTKVEIK $V_L$ CDR1 (SEQ ID NO: 14):       QSVDSY $V_L$ CDR2 (SEQ ID NO: 15):       DAS $V_L$ CDR3 (SEQ ID NO: 16):       QQRSNWPPT

3H8 VK #3 (VK 3-11; JK1)
A further light chain was also found to be active as follows (though only the above light chain (3H8-1B11 VK #2) was used in the above Examples):

V<sub>L</sub> nucleic acid sequence (SEQ ID NO: 17)

```
Atggaagcccagctcagcttctcttcctcctgctactctggctccca
gataccaccggagaaattgtgttgacacagtctccagccaccctgtct
ttgtctccaggggaaagagccaccctctcctgcagggccagtcagagt
gttagcagctacttagcctggtaccaacagaaacctggccaggctccc
aggctcctcatctatgatgcatccagcagggccactggcatcccagac
aggttcagtggcagtgggtctgggacagacttcactctcaccatcagc
agactggagcctgaagattttgcagtgtattactgtcagcagcgtagc
aactggcctccgacgttcggccaagggaccaaggtggaaatcaaa
```

V<sub>L</sub> amino acid sequence (SEQ ID NO: 18) (including signal peptide in underlined italics):

*MEAPAQLLFLLLLWLPDTTG*EIVLTQSPATLSLSPGERATLSCRASQS
VSSYLAWYQQKPGQAPRLLIYDASSRATGIPDRFSGSGSGTDFTLTIS
RLEPEDFAVYYCQQRSNWPPTFGQGTKVEIK

V<sub>L</sub> amino acid sequence (SEQ ID NO: 19) excluding signal peptide:

EIVLTQSPATLSLSPGERATLSCRASQSVSSYLAWYQQKPGQAPRLLI
YDASSRATGIPDRFSGSGSGTDFTLTISRLEPEDFAVYYCQQRSNWPP
TFGQGTKVEIK

V<sub>L</sub> CDR1 (SEQ ID NO: 20):    QSVSSY

V<sub>L</sub> CDR2 (SEQ ID NO: 21):    DAS

V<sub>L</sub> CDR3 (SEQ ID NO: 22):    QQRSNWPPT

2C2 VH (VH 3-33; D1-7; JH4)
V<sub>H</sub> nucleic acid sequence (SEQ ID NO: 23)

```
Atggagtttgggctgagctgggttttcctcgttgctcttttaagaggtgt
ccagtgtcaggtgcaactggtggagtctgggggaggcgtggtccagcctg
ggaggtccctgcgactctcctgtgcagcgtctggattcaccttcagtagc
tatgacatacactgggtccgccaggctccaggcaaggggctggagtgggt
ggcagttatatggaatgatggaagtaataaatactatgcagactccgtga
agggccgattcaccatctccagagacaattccacgaactcgctgtttctg
caaatgaacagcctgagagccgaggacacggctgtgtattattgtgtggg
aggaactgctgaccttaacactgggaccagggaaccctggtcaccgtct
cctca
```

V<sub>H</sub> amino acid sequence (SEQ ID NO: 24) (including signal peptide in underlined italics):

*MEFGLSWVFLVALLRGVQC*QVQLVESGGGVVQPGRSLRLSCAASGFTFSS
YDIHWVRQAPGKGLEWVAVIWNDGSNKYYADSVKGRFTISRDNSTNSLFL
QMNSLRAEDTAVYYCVGGTADLEHWDQGTLVTVSS

V<sub>H</sub> amino acid sequence (SEQ ID NO: 25) excluding signal peptide:

QVQLVESGGGVVQPGRSLRLSCAASGFTFSSYDIHWVRQAPGKGLEWVAV
IWNDGSNKYYADSVKGRFTISRDNSTNSLFLQMNSLRAEDTAVYYCVGGT
ADLEHWDQGTLVTVSS

V<sub>H</sub> CDR1 (SEQ ID NO: 26):
GFTFSSYD

V<sub>H</sub> CDR2 (SEQ ID NO: 27):
IWNDGSNK

V<sub>H</sub> CDR3 (SEQ ID NO: 28):
VGGTADLEHWDQ

2C2 VK (VK 1D-16; JK4)
V<sub>L</sub> nucleic acid sequence (SEQ ID NO: 29)

```
Atgagggtcctcgctcagctcctggggctcctgctgctctgtttcccagg
tgccagatgtgacatccagatgacccagtctccatcctcactgtctgcat
ctgtaggagacagagtcaccatcacttgtcgggcgagtcagggtattagc
agctggttagcctggtatcagcagaaaccagagaaagcccctaagtccct
gatctatgctgcatccagtttgcaaagtggggtcccatcaaggttcagcg
gcagtggatctgggacagatttcactctcaccatcagcagcctgcagcct
gaagattttgcaacttattactgccaacagtataatagttaccctctcac
tttcggcggagggaccaaggtggagatcaaa
```

V<sub>L</sub> amino acid sequence (SEQ ID NO: 30) (including signal peptide in underlined italics):

*MRVLAQLLGIILLCFPGARC*DIQMTQSPSSLSASVGDRVTITCRASQGIS
SWLAWYQQKPEKAPKSLIYAASSLQSGVPSRFSGSGSGTDFTLTISSLQP
EDFATYYCQQYNSYPLTFGGGTKVEIK

V<sub>L</sub> amino acid sequence (SEQ ID NO: 31) excluding signal peptide:

DIQMTQSPSSLSASVGDRVTITCRASQGISSWLAWYQQKPEKAPKSLIYA
ASSLQSGVPSRFSGSGSGTDFTLTISSLQPEDFATYYCQQYNSYPLTFGG
GTKVEIK

V<sub>L</sub> CDR1 (SEQ ID NO: 32):
QGISSW

V<sub>L</sub> CDR2 (SEQ ID NO: 33):
AAS

V<sub>L</sub> CDR3 (SEQ ID NO: 34):
QQYNSYPLT

1F5 VH (VH 3-33; D7-27; JH4)
V<sub>H</sub> nucleic acid sequence (SEQ ID NO: 35)

```
Atggagtttgggctgagctgggttttcctcgttgctcttttaagaggtgt
ccagtgtcaggtgcagctggtggagtctgggggaggcgtggtccagcctg
ggaggtccctgagactctcctgtgcagcgtctggattcaccttcagtagt
``` tatgacatgcactgggtccgccaggctccaggcaaggggctggagtgggt ggcagttatatggtatgatggaagtaataaatactatgcagactccgtga agggccgattcaccatctccagagacaattccaagaacacgctgtatctc caaatgaacagcctgagagccgaggacacggctgtgtattactgtgcgag aggtagtggtaactggggtttctttgactactggggccagggaaccctgg tcaccgtctcctca $V_H$ amino acid sequence (SEQ ID NO: 36) (including signal peptide in underlined italics):

*MEFGLSWVFLVALLRGVQC*QVQLVESGGGVVQPGRSLRLSCAASGFTFSS

YDMHWVRQAPGKGLEWVAVIWYDGSNKYYADSVKGRFTISRDNSKNTLYL

QMNSLRAEDTAVYYCARGSGNWGFFDYWGQGTLVTVSS $V_H$ amino acid sequence (SEQ ID NO: 37) excluding signal peptide:

QVQLVESGGGVVQPGRSLRLSCAASGFTFSSYDMHWVRQAPGKGLEWVAV

IWYDGSNKYYADSVKGRFTISRDNSKNTLYLQMNSLRAEDTAVYYCARGS

GNWGFFDYWGQGTLVTVSS $V_H$ CDR1 (SEQ ID NO: 38):
GFTFSSYD $V_H$ CDR2 (SEQ ID NO: 39):
IWYDGSNK $V_H$ CDR3 (SEQ ID NO: 40):
ARGSGNWGFFDY

1F5 VK #2 (VK 1D-16; JK1)
$V_L$ nucleic acid sequence (SEQ ID NO: 41)

Atgagggtcctcgctcagctcctggggctcctgctgctctgtttccagg tgccagatgtgacatccagatgacccagtctccatcctcactgtctgcat ctgtaggagacagagtcaccatcacttgtcgggcgagtcagggtattagc aggtggttagcctggtatcagcagaaaccagagaaagcccctaagtccct gatctatgctgcatccagtttgcaaagtggggtcccatcaaggttcagcg gcagtggatctgggacagatttcactctcaccatcagcagcctgcagcct gaagattttgcaacttattactgccaacagtataatactaccctcggac gttcggccaagggaccaaggtggaaatcaaa $V_L$ amino acid sequence (SEQ ID NO: 42) (including signal peptide in underlined italics):

*MRVLAQLLGLLLLCFPGARC*DIQMTQSPSSLSASVGDRVTITCRASQGIS

RWLAWYQQKPEKAPKSLIYAASSLQSGVPSRFSGSGSGTDFTLTISSLQP

EDFATYYCQQYNTYPRTFGQGTKVEIK $V_L$ amino acid sequence (SEQ ID NO: 43) excluding signal peptide:

DIQMTQSPSSLSASVGDRVTITCRASQGISRWLAWYQQKPEKAPKSLIYA

ASSLQSGVPSRFSGSGSGTDFTLTISSLQPEDFATYYCQQYNTYPRTFGQ

GTKVEIK $V_L$ CDR1 (SEQ ID NO: 44):
QGISRW $V_L$ CDR2 (SEQ ID NO: 45):
AAS $V_L$ CDR3 (SEQ ID NO: 46):
QQYNTYPRT

1H8 VH (VH 3-33; D7-27; JH4)
$V_H$ nucleic acid sequence (SEQ ID NO: 47)

Atggagtttgggctgagctgggttttcctcgttgctcttttaagaggtgt ccagtgtcaggtgcagctggtggagtctgggggaggcgtggtccagcctg ggaggtccctgagactctcctgtgcagcgtctggattcaccttcaatatc tatgacatgcactgggtccgccaggctccaggcaaggggctggagtgggt ggcagttatatggtatgatggaagtaatcaatactatgcagactccgtga agggccgattcaccatctccagagacaattccaagaacacgctgtatctg caaatgaacattttgagagccgaggacacggctgtgtattactgtgcgag aggtactcactgggggtactttgactactggggccagggaaccctggtca ccgtctcctca $V_H$ amino acid sequence (SEQ ID NO: 48) (including signal peptide in underlined italics):

*MEFGLSWVFLVALLRGVQC*QVQLVESGGGVVQPGRSLRLSCAASGFTFNI

YDMHWVRQAPGKGLEWVAVIWYDGSNQYYADSVKGRFTISRDNSKNTLYL

QMNILRAEDTAVYYCARGTHWGYFDYWGQGTLVTVSS $V_H$ amino acid sequence (SEQ ID NO: 49) excluding signal peptide:

QVQLVESGGGVVQPGRSLRLSCAASGFTFNIYDMHWVRQAPGKGLEWVAV

IWYDGSNQYYADSVKGRFTISRDNSKNTLYLQMNILRAEDTAVYYCARGT

HWGYFDYWGQGTLVTVSS $V_H$ CDR1 (SEQ ID NO: 50):
GFTFNIYD $V_H$ CDR2 (SEQ ID NO: 51):
IWYDGSNQ $V_H$ CDR3 (SEQ ID NO: 52):
ARGTHWGYFDY

1H8 VK (VK 1D-16; JK1)
$V_L$ nucleic acid sequence (SEQ ID NO: 53)

Atgagggtcctcgctcagctcctggggctcctgctgctctgtttccc aggtgccagatgtgacatccagatgacccagtctccatcctcactgt ctgcatctgtaggagacagagtcaccatcacttgtcgggcgagtcag ggtattagcagctggttagcctggtatcagcagaaaccagagaaagc cctaagtccctgatctatgctgcatccaatttgcaaagtggggtcc catcaaggttcagcggcagtggatctgggacagatttcactctcacc -continued atcagcagcctgcagcctgaagattttgcaacttattactgccaaca gtataatagttaccctcggacgttcggccaagggaccaaggtggaaa tcaaa $V_L$ amino acid sequence (SEQ ID NO: 54) (including signal peptide in underlined italics):

*MRVLAQLLGLLLLCFPGARC*DIQMTQSPSSLSASVGDRVTITCRAS
QGISSWLAWYQQKPEKAPKSLIYAASNLQSGVPSRFSGSGSGTDFT
LTISSLQPEDFATYYCQQYNSYPRTFGQGTKVEIK $V_L$ amino acid sequence (SEQ ID NO: 55) excluding signal peptide:

DIQMTQSPSSLSASVGDRVTITCRASQGISSWLAWYQQKPEKAPKSL
IYAASNLQSGVPSRFSGSGSGTDFTLTISSLQPEDFATYYCQQYNSY
PRTFGQGTKVEIK $V_L$ CDR1 (SEQ ID NO: 56):  QGISSW $V_L$ CDR2 (SEQ ID NO: 57):  AAS $V_L$ CDR3 (SEQ ID NO: 58):  QQYNSYPRT

1G5 VH (VH 3-33; D6-19; JH2)
$V_H$ nucleic acid sequence (SEQ ID NO: 59)

Atggagtttgggctgagctgggttttcctcgttgctcttttaagaggt gtccagtgtcaggtgcaactggtggagtctgggggaggcgtggtccag cctggggaggtccctgagactctcctgtgcagcgtctggattcagcttc agtagctatggcatgcactgggtccgccaggctccaggcaagggactg gagtgggtggcacttctatggtatgatggtagccataaagactttgca gactccgtgaagggccgattcaccatctccagagacaattccaagaac acgctagatctgcaaatgaacagcctgagagccgaggacacggctgtg tattactgtgcgagagagggtttagcagtacctggtcactggtacttc gatctctggggccgtggcaccctggtcactgtctcctca $V_H$ amino acid sequence (SEQ ID NO: 60) (including signal peptide in underlined italics):

*MEFGLSWVFLVALLRGVQC*QVQLVESGGGVVQPGRSLRLSCAASGFSF
SSYGMHWVRQAPGKGLEWVALLWYDGSHKDFADSVKGRFTISRDNSKN
TLDLQMNSLRAEDTAVYYCAREGLAVPGHWYFDLWGRGTLVTVSS $V_H$ amino acid sequence (SEQ ID NO: 61) excluding signal peptide:

QVQLVESGGGVVQPGRSLRLSCAASGFSFSSYGMHWVRQAPGKGLEWV
ALLWYDGSHKDFADSVKGRFTISRDNSKNTLDLQMNSLRAEDTAVYYC
AREGLAVPGHWYFDLWGRGTLVTVSS $V_H$ CDR1 (SEQ ID NO: 62):  GFSFSSYG $V_H$ CDR2 (SEQ ID NO: 63):  LWYDGSHK $V_H$ CDR3 (SEQ ID NO: 64):  AREGLAVPGHWYFDL

1G5 VK (VK 1-13; JK1)
$V_L$ nucleic acid sequence (SEQ ID NO: 65)

Atgagggtccccgctcagctcctggggcttctgctgctctggctccc aggtgccagatgtgccatccagttgacccagtctccatcctccctgt ctgcatctgtaggagacagagtcaccatcacttgccgggcaagtcag ggcattagcagtgctttagcctggtatcagcagaaaccagggaaagc tcctaagctcctgatctatgatgcctccagtttggaaagtggggtcc catcaaggttcagcggcagtggatctgggacagatttcactctcacc atcagcagcctgcagcctgaagattttgcaacttattactgtcaaca gtttaatacttaccctcggacgttcggccaagggaccaaggtggaaa tcaaa $V_L$ amino acid sequence (SEQ ID NO: 66) (including signal peptide in underlined italics):

*MRVPAQLLGLLLLWLPGARC*AIQLTQSPSSLSASVGDRVTITCRASQ
GISSALAWYQQKPGKAPKLLIYDASSLESGVPSRFSGSGSGTDFTLT
ISSLQPEDFATYYCQQFNTYPRTFGQGTKVEIK $V_L$ amino acid sequence (SEQ ID NO: 67) excluding signal peptide:

AIQLTQSPSSLSASVGDRVTITCRASQGISSALAWYQQKPGKAPKLL
IYDASSLESGVPSRFSGSGSGTDFTLTISSLQPEDFATYYCQQFNTY
PRTFGQGTKVEIK $V_L$ CDR1 (SEQ ID NO: 68):  QGISSA $V_L$ CDR2 (SEQ ID NO: 69):  DAS $V_L$ CDR3 (SEQ ID NO: 70):  QQFNTYPRT

2G9 VH (VH 3-33; D1-7; JH4)
$V_H$ nucleic acid sequence (SEQ ID NO: 71)

Atggagtttgggctgagctgggttttcctcgttgctcttttaagaggt gtccagtgtcaggtgcagttggtggagtctgggggaggcgtggtccag cctggggaggtccctgcgactctcctgtgcagcgtctggattcaccctc agtagccatgacatacactgggtccgccaggctccaggcaaggggctg gagtgggtggcagttatatggaatgatggaagtaataaatactatgca gactccgtgaagggccgattcaccatctccagagacaattccacgaac tcgctgtttctgcaaatgaacagcctgagagccgaggacacggctgtg tattattgtgtgagaggaactgctgaccttgaacactgggaccaggga accctggtcaccgtctcctca $V_H$ amino acid sequence (SEQ ID NO: 72) (including signal peptide in underlined italics):

*MEFGLSWVFLVALLRGVQC*QVQLVESGGGVVQPGRSLRLSCAASGFTL
SSHDIHWVRQAPGKGLEWVAVIWNDGSNKYYADSVKGRFTISRDNSTN
SLFLQMNSLRAEDTAVYYCVRGTADLEHWDQGTLVTVSS

V_H amino acid sequence (SEQ ID NO: 73) excluding signal peptide:

```
QVQLVESGGGVVQPGRSLRLSCAASGFTLSSHDIHWVRQAPGKGLEW
VAVIWNDGSNKYYADSVKGRFTISRDNSTNSLFLQMNSLRAEDTAVY
YCVRGTADLEHWDQGTLVTVSS

V_H CDR1 (SEQ ID NO: 74):     GFTLSSHD

V_H CDR2 (SEQ ID NO: 75):     IWNDGSNK

V_H CDR3 (SEQ ID NO: 76):     VRGTADLEHWDQ
```

2G9 VK (VK 1D-16; JK4)
V_L nucleic acid sequence (SEQ ID NO: 77)

```
Atgagggtcctcgctcagctcctggggctcctgctgctctgtttccca
ggtgccagatgtgacatccagatgacccagtctccatcctcactgtctc
gcatctgtaggagacagagtcaccatcacttgtcgggcgagtcagggt
attagcagctggttagcctggtatcagcagaaaccagagaaagcccct
aagtccctgatctatgctgcatccagtttgcaaagtggggtcccatca
aggttcagcggcagtggatctgggacagatttcactctcaccatcagc
agcctgcagcctgaagattttgcaacttattactgccaacagtataat
agttaccctctcactttcggcggagggaccaaggtggagatcaaa
```

V_L amino acid sequence (SEQ ID NO: 78) (including signal peptide in underlined italics):

```
MRVLAQLLGLLLLCFPGARCDIQMTQSPSSLSASVGDRVTITCRASQ
GISSWLAWYQQKPEKAPKSLIYAASSLQSGVPSRFSGSGSGTDFTLT
ISSLQPEDFATYYCQQYNSYPLTFGGGTKVEIK
```

V_L amino acid sequence (SEQ ID NO: 79) excluding signal peptide:

```
DIQMTQSPSSLSASVGDRVTITCRASQGISSWLAWYQQKPEKAPKSL
IYAASSLQSGVPSRFSGSGSGTDFTLTISSLQPEDFATYYCQQYNSY
PLTFGGGTKVEIK

V_L CDR1 (SEQ ID NO: 80):     QGISSW

V_L CDR2 (SEQ ID NO: 81):     AAS

V_L CDR3 (SEQ ID NO: 82):     QQYNSYPLT
```

3A10 VH (VH 3-33; D3-10; JH3)
V_H nucleic acid sequence (SEQ ID NO: 83)

```
Atggagtttgggctgagctgggttttcctcgttgctcttttaagaggtgt
ccagtgtcaggtgcagctggtggagtctgggggaggcgtggtccagcctg
ggaggtccctgagactctcctgtgcagcgtctggattcaccttcagtcat
tatggcatgcactgggtccgccaggctccaggcaaggggccggagtgggt
ggcaattatatggtatgatggaagtaataaatactatgcagactccgtga
agggccgattcaccatctccagagacaattccaagaacacgctggatctg
caaatgaacagcctgagagccgaggacacggctgtgtattactgtgcgag
agatggatggactactatggttcggggacttaatgttttgatatctggg
gccaagggacaatggtcaccgtctcttca
```

V_H amino acid sequence (SEQ ID NO: 84) (including signal peptide in underlined italics):

```
MEFGLSWVFLVALLRGVQCQVQLVESGGGVVQPGRSLRLSCAASGFTFSH
YGMHWVRQAPGKGPEWVAIIWYDGSNKYYADSVKGRFTISRDNSKNTLDL
QMNSLRAEDTAVYYCARDGWTTMVRGLNVFDIWGQGTMVTVSS
```

V_H amino acid sequence (SEQ ID NO: 85) excluding signal peptide:

```
QVQLVESGGGVVQPGRSLRLSCAASGFTFSHYGMHWVRQAPGKGPEWVAI
IWYDGSNKYYADSVKGRFTISRDNSKNTLDLQMNSLRAEDTAVYYCARDG
WTTMVRGLNVFDIWGQGTMVTVSS

V_H CDR1 (SEQ ID NO: 86):
GFTFSHYG

V_H CDR2 (SEQ ID NO: 87):
IWYDGSNK

V_H CDR3 (SEQ ID NO: 88):
ARDGWTTMVRGLNVFDI
```

3A10 VK #1 (VK 1D-16; JK5)
V_L nucleic acid sequence (SEQ ID NO: 89)

```
Atgagggtcctcgctcagctcctggggctcctgctgctctgtttcccagg
tgccagatgtgacatccagatgacccagtctccatcctcactgtctgcat
ctgtaggagacagagtcaccatcacttgtcgggcgagtcaggatattagc
agctggttagcctggtatcagcagaaaccagagaaagcccctaagtccct
gatctatgctgcatccagtttgcaaagtggggtcccatcaaggttcagcg
gcagtggatctgggacagatttcactctcaccatcagcagcctgcagcct
gaagattttgcaacttattactgccaacagtataatagttaccctcccac
cttcggccaagggacacgactggagattaaa
```

V_L amino acid sequence (SEQ ID NO: 90) (including signal peptide in underlined italics):

```
MRVLAQLLGIILLCFPGARCDIQMTQSPSSLSASVGDRVTITCRASQDIS
SWLAWYQQKPEKAPKSLIYAASSLQSGVPSRFSGSGSGTDFTLTISSLQP
EDFATYYCQQYNSYPPTFGQGTRLEIK
```

V_L amino acid sequence (SEQ ID NO: 91) excluding signal peptide:

```
DIQMTQSPSSLSASVGDRVTITCRASQDISSWLAWYQQKPEKAPKSLIYA
ASSLQSGVPSRFSGSGSGTDFTLTISSLQPEDFATYYCQQYNSYPPTFGQ
GTRLEIK

V_L CDR1 (SEQ ID NO: 92):
QDISSW
```

V_L CDR2 (SEQ ID NO: 93):
AAS

V_L CDR3 (SEQ ID NO: 94):
QQYNSYPPT

3A10 VK #4 (VK 1-13; JK5)
A further light chain was also found to be active as follows (though only the above light chain (3H8-1B11 VK #1) was used in the above Examples):
V_L nucleic acid sequence (SEQ ID NO: 95)

Atgagggtcctcgctcagctcctggggcttctgctgctctggctcccagg tgccagatgtgccatccagttgacccagtctccatcctcctgtctgcat ctgtaggagacagagtcaccatcacttgccgggcaagtcagggcattagc agtgctttagcctggtatcagcagaaaccagagaaagcccctaagtccct gatctatgctgcatccagtttgcaaagtggggtcccatcaaggttcagcg gcagtggatctgggacagatttcactctcaccatcagcagcctgcagcct gaagattttgcaacttattactgccaacagtataatagttaccctcccac cttcggccaagggacacgactggagattaaa V_L amino acid sequence (SEQ ID NO: 96) (including signal peptide in underlined italics):

*MRVLAQLLGLLLLWLPGARC*AIQLTQSPSSLSASVGDRVTITCRAS<u>QGIS</u>

<u>SALA</u>WYQQKPEKAPKSLIY<u>AAS</u>SLQSGVPSRFSGSGSGTDFTLTISSLQP

EDFATYYC<u>QQYNSYPPT</u>FGQGTRLEIK

V_L amino acid sequence (SEQ ID NO: 97) excluding signal peptide:

AIQLTQSPSSLSASVGDRVTITCRAS<u>QGISSALA</u>WYQQKPEKAPKSLIY<u>A</u>

<u>AS</u>SLQSGVPSRFSGSGSGTDFTLTISSLQPEDFATYYC<u>QQYNSYPPT</u>FGQ

GTRLEIK

V_L CDR1 (SEQ ID NO: 98):
QGISSA

V_L CDR2 (SEQ ID NO: 99):
AAS

V_L CDR3 (SEQ ID NO: 100):
QQYNSYPPT

3H12 VH (VH 3-33; D7-27; JH4)
V_H nucleic acid sequence (SEQ ID NO: 101)

atggagtttgggctgagctgggttttcctcgttgctcttttaagaggtgt ccagtgtcaggtgcagctggtggagtctgggggaggcgtggtccagcctg ggaggtccctgagactctcctgtgcaacgtctggattcaccttcagtagc tatgacatgcactgggtccgccaggctccaggcaaggggctggagtgggt ggcagttatttggtatgatggaagtaataaatactatgcagactccgtga agggccgattcaccatctccagagacaattccaagaacacgctgtatctc caaatgaacagcctgggagacgaggacacggctgtgtattactgtgcgag aggtagtggtaactggggtttctttgactactggggccagggaaccctgg tcaccgtctcctca V_H amino acid sequence (SEQ ID NO: 102) (including signal peptide in underlined italics):

*MEFGLSWVFLVALLRGVQC*QVQLVESGGGVVQPGRSLRLSCATS<u>GFTFSS</u>

<u>YD</u>MHWVRQAPGKGLEWVAV<u>IWYDGSNK</u>YYADSVKGRFTISRDNSKNTLYL

QMNSLGDEDTAVYYC<u>ARGSGNWGFFDY</u>WGQGTLVTVSS

V_H amino acid sequence (SEQ ID NO: 103) excluding signal peptide:

QVQLVESGGGVVQPGRSLRLSCATS<u>GFTFSSYD</u>MHWVRQAPGKGLEWVAV

<u>IWYDGSNK</u>YYADSVKGRFTISRDNSKNTLYLQMNSLGDEDTAVYYC<u>ARGS</u>

<u>GNWGFFDY</u>WGQGTLVTVSS

V_H CDR1 (SEQ ID NO: 104):
GFTFSSYD

V_H CDR2 (SEQ ID NO: 105):
IWYDGSNK

V_H CDR3 (SEQ ID NO: 106):
ARGSGNWGFFDY

3H12 VK #2 (VK 1D-16; JK1)
V_L nucleic acid sequence (SEQ ID NO: 107)

Atgagggtcctcgctcagctcctggggctcctgctgctctgtttcccagg tgccagatgtgacatccagatgacccagtctccatcctcactgtctgcat ctgtaggagacagagtcaccatcacttgtcgggcgagtcagggtattagc aggtggttagcctggtatcagcagaaaccagagaaagcccctaagtccct gatctatgctgcatccagtttgcaaagtggggtcccatcaaggttcagcg gcagtggatctgggacagatttcactctcaccatcagcagcctgcagcct gaagattttgcaacttattactgccaacagtataatacttaccctcggac gttcggccaagggaccaaggtggaaatcaaa V_L amino acid sequence (SEQ ID NO: 108) (including signal peptide in underlined italics):

*MRVLAQLLGLLLLCFPGARC*DIQMTQSPSSLSASVGDRVTITCRAS<u>QGIS</u>

<u>RW</u>LAWYQQKPEKAPKSLIY<u>AAS</u>SLQSGVPSRFSGSGSGTDFTLTISSLQP

EDFATYYC<u>QQYNTYPRT</u>FGQGTKVEIK

V_L amino acid sequence (SEQ ID NO: 109) excluding signal peptide:

DIQMTQSPSSLSASVGDRVTITCRAS<u>QGISRW</u>LAWYQQKPEKAPKSLIY<u>A</u>

<u>AS</u>SLQSGVPSRFSGSGSGTDFTLTISSLQPEDFATYYC<u>QQYNTYPRT</u>FGQ

GTKVEIK

V_L CDR1 (SEQ ID NO: 110):
QGISRW

-continued

V$_L$ CDR2 (SEQ ID NO: 111):
AAS

V$_L$ CDR3 (SEQ ID NO: 112):
QQYNTYPRT
ALIGNMENTS ARE SHOWN IN FIGS 15 AND 16

Example 10

In Vivo Non-Human Primate Study

Figure 17:
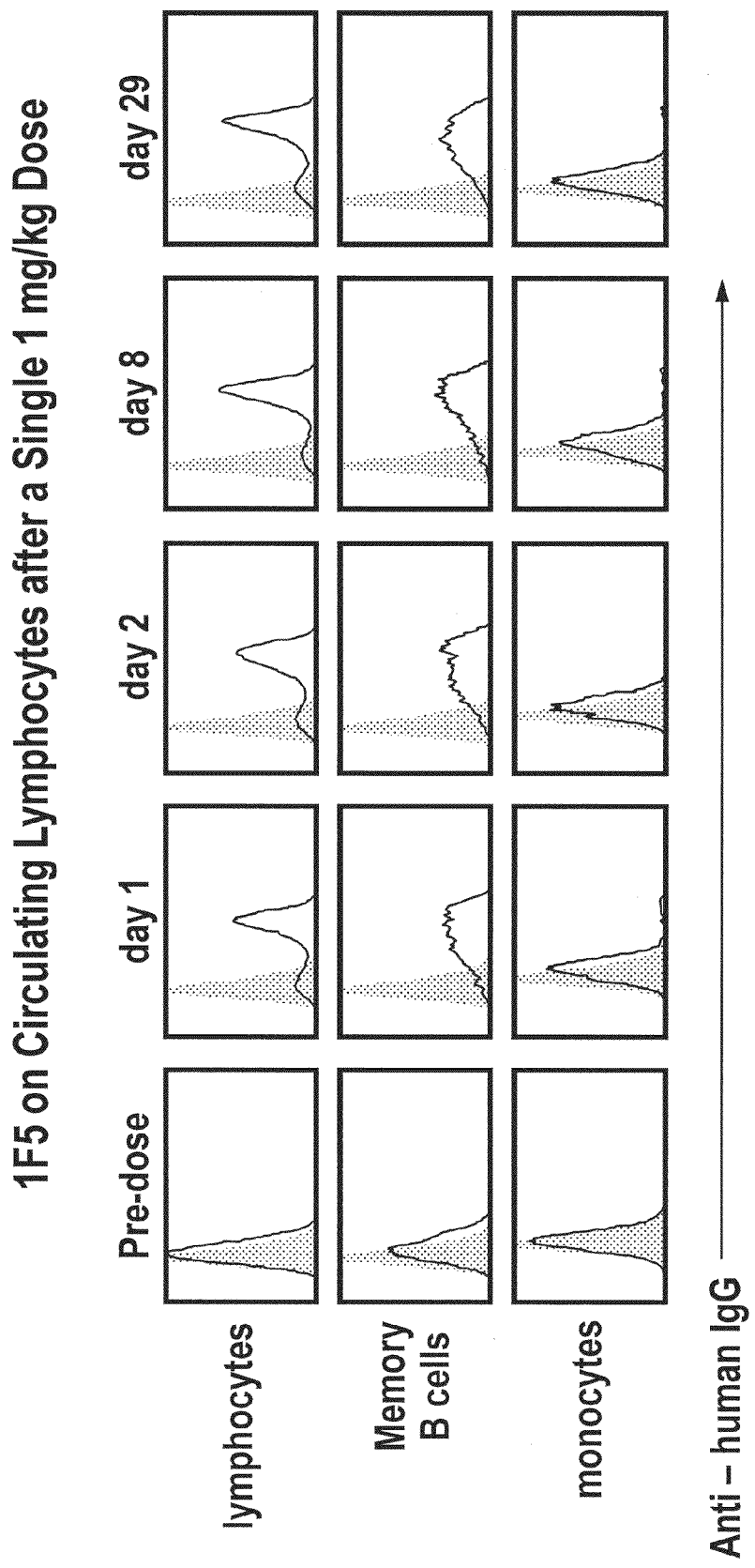
FIGS. 17 and 18 show results from an in vivo non-human primate study using mAb 1F5. In particular.

To assess tolerance of anti-human CD27 mAb 1F5 in non-human primates, 3 cynomolgus monkeys were treated with one i.v. dose of 1, 3 or 10 mg/kg of 1F5. Animals were followed for 29 days. Total lymphocytes (based on side and forward scatter size), memory B cells (CD20+ and CD95 bright), and monocytes (based on side and forward scatter size) were stained with anti-human IgG antibody (bold line) and compared to unstained controls (shaded histogram). The results are shown in FIG. 17. These results show that the 1F5 mAb was bound to the surface of circulating lymphocytes know to express CD27 for the entire duration of the study. Monocytes, cells that do not express CD27 did not have 1F5 binding.

In addition, to determine the effect of 1F5 on circulating lymphocyte populations, lymphocytes were stained with subset markers and the % positive cells plotted vs time in FIG. 17 for each animal treated at the different doses (square points=1 mg/kg; circle points=3 mg/kg; triangle points=10 mg/kg). Results are shown in FIG. 18.

Figure 18:
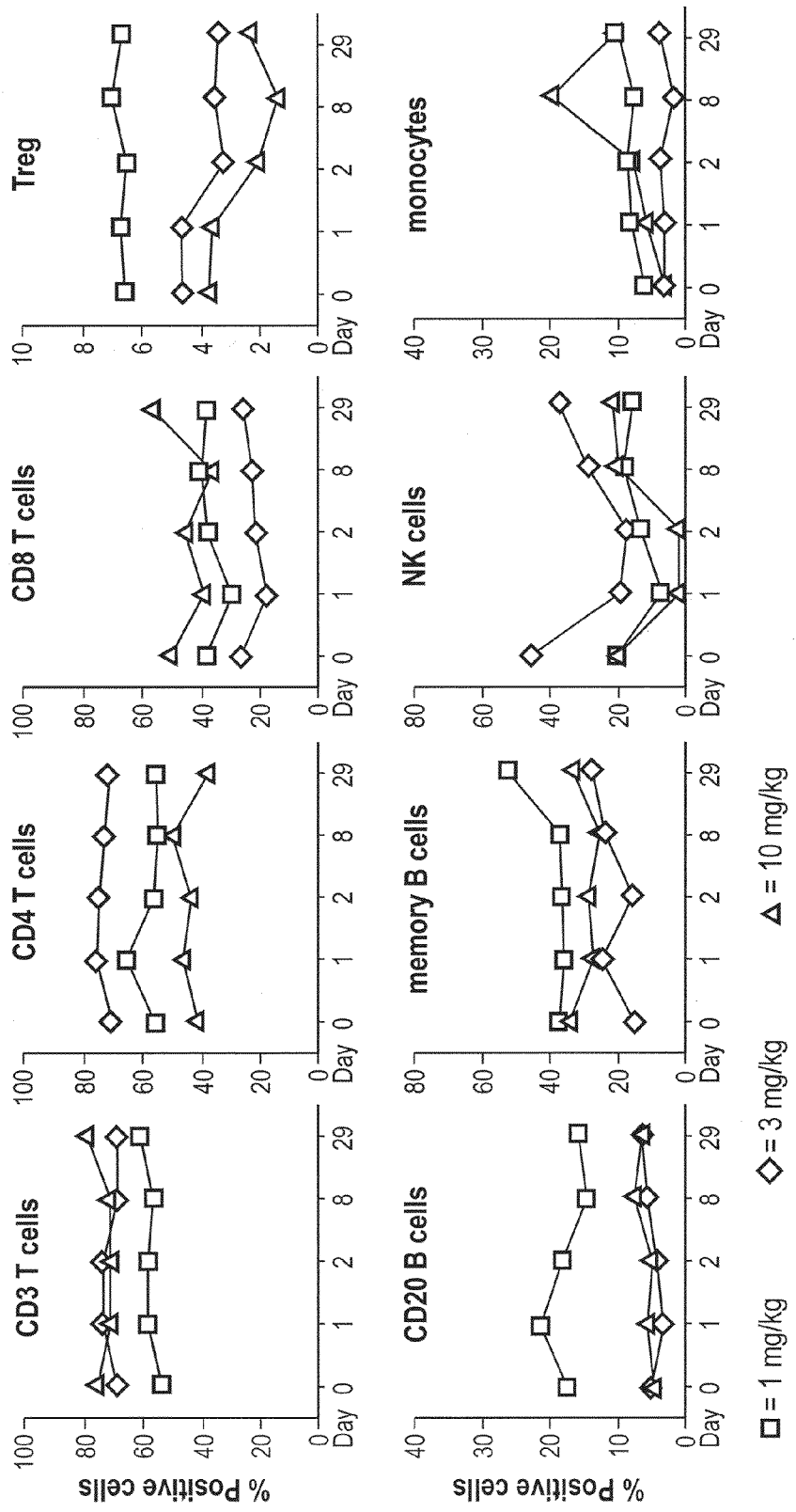

Collectively, the results from these studies, shown in FIGS. 17 and 18, demonstrate that 1F5 was well tolerated and did not significantly deplete circulating lymphocytes (other than some transient depletion of NK cells) after a single 1-10 mg/kg dose. In addition, there was no elevation in body temperatures and no detectable levels of TNF-α, IL-6 or IL-1β.

Example 11

Figure 19:
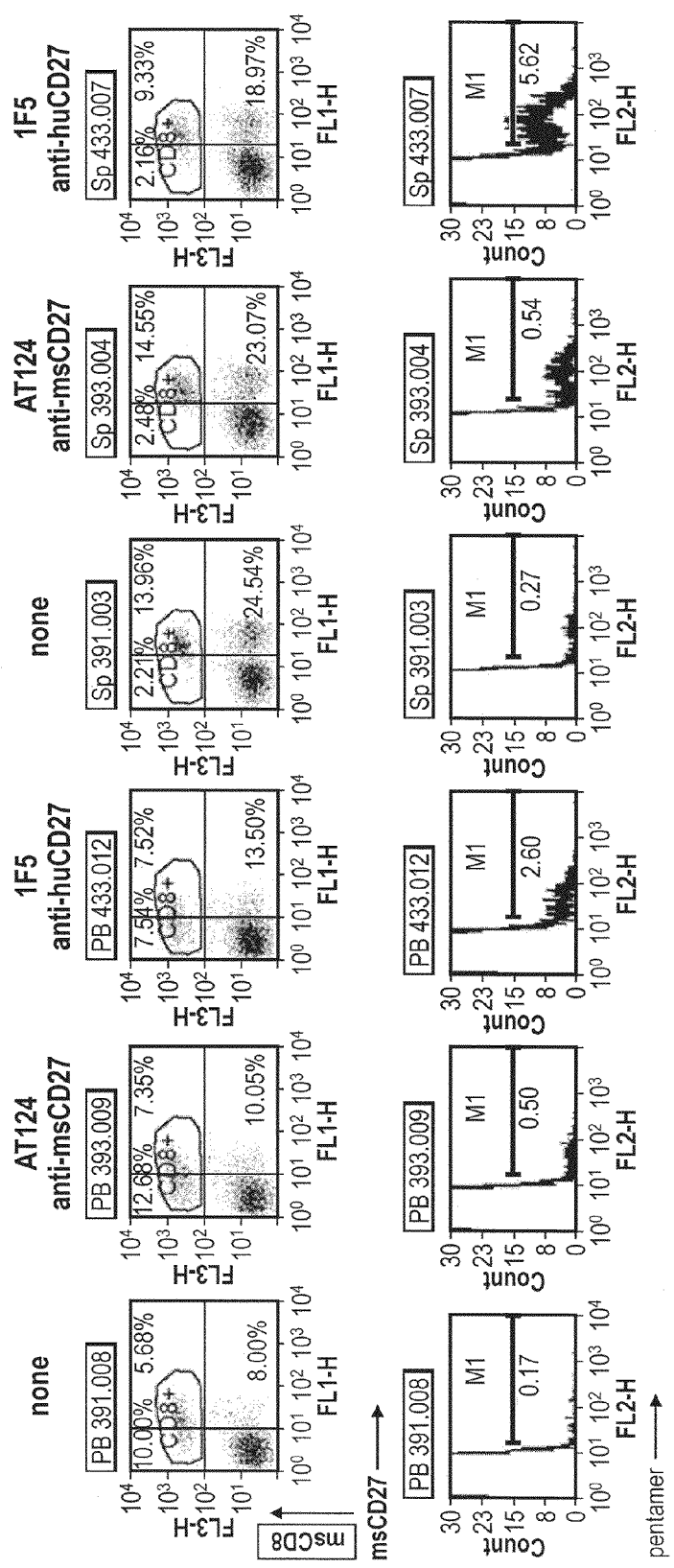
FIG. 19 depicts the results of a pentamer staining assay on mouse peripheral blood cells and splenocytes.
Figure 21:
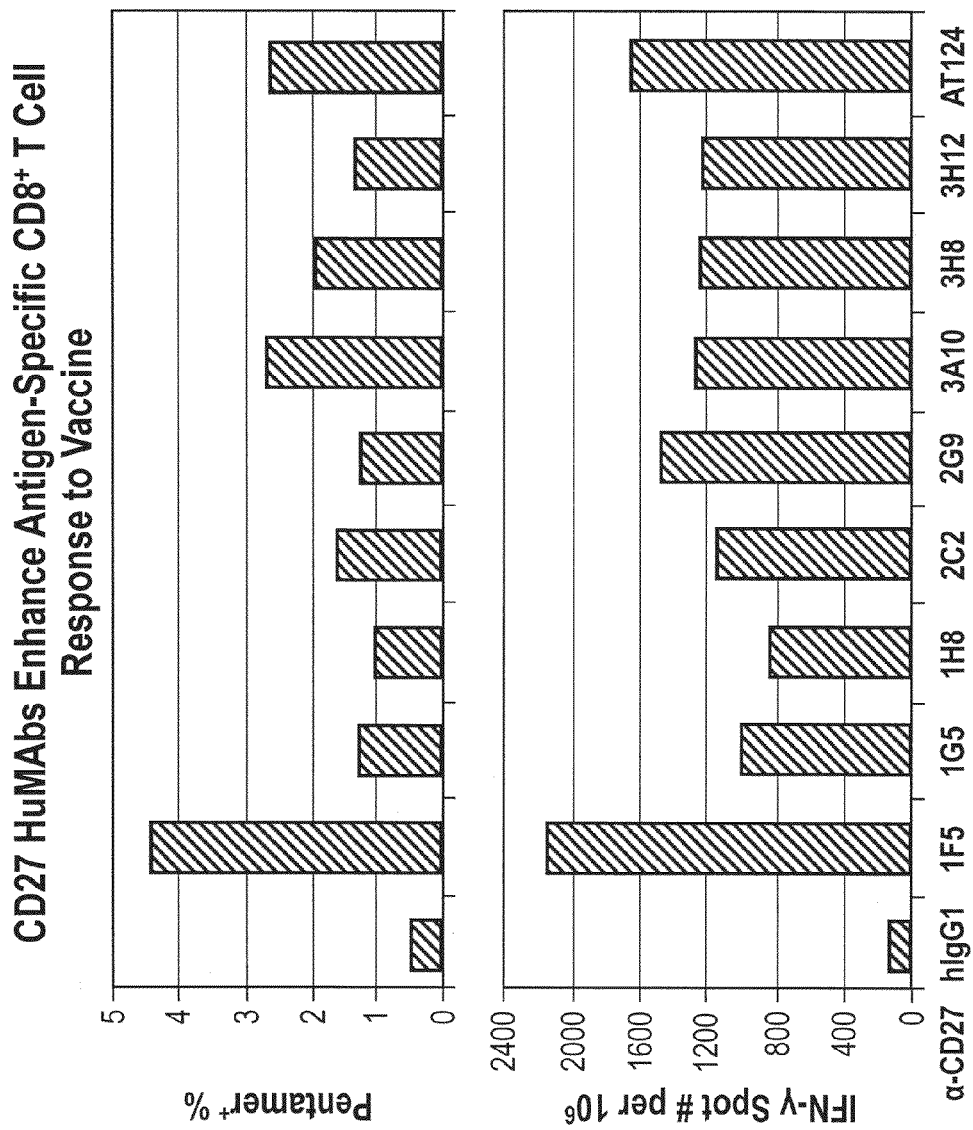
FIG. 21 shows enhancement by anti-CD27 mAbs of T cell responses to a vaccine antigen in a transgenic mouse model by pentamer staining and IFN ELISPOT.

Anti-CD27 mAbs Enhanced Antigen-Specific CD8+ T-Cell Proliferation and Activation Pentamer Staining on Mouse Peripheral Blood Cells and Splenocytes Human CD27 transgenic mice (huCD27-Tg) were intravenously injected with 5 mg of chicken ovalbumin and the panel of fully human antibodies recognizing human CD27 generated as in Example 1 (CD27 human mAbs). Rat anti-mouse CD27 clone AT124 and irrelevant human IgG1 were included as positive and negative controls, respectively. Each antibody (250 µg) was co-injected with ovalbumin on day 0 and an additional 250 µg of antibody alone on day 1. Peripheral blood and spleen cells were harvested on day 7. Splenocytes ($1 \times 10^6$) or whole blood (100 µl) were used for staining. After Fc-receptor blocking, cells were stained with 10 µl of H-2Kb/SIINFEKL (SEQ ID NO: 119), a tetrameric complex of mouse MHC complexed with the peptide T cell epitope from ovalbumin (Beckman Coulter), or a similar pentameric complex (ProImmune), anti-CD8 (eBioscience) and anti-huCD27 mAb or anti-msCD27 mAb (BD Biosciences) at room temperature for 30 minutes. Cells were then RBC-lysed, washed and fixed, and at least 100,000 events were acquired in Flow Cytometer LSR (BD Biosciences). The fraction of tetramer- or pentamer-positive cells in the CD8$^+$ or CD27$^+$ gated population was determined. Results are shown in FIGS. 19 and 21 from which it can be seen that the anti-CD27 antibodies significantly enhanced immune responses.

Example 12

ELISPOT Assay

Figure 20:
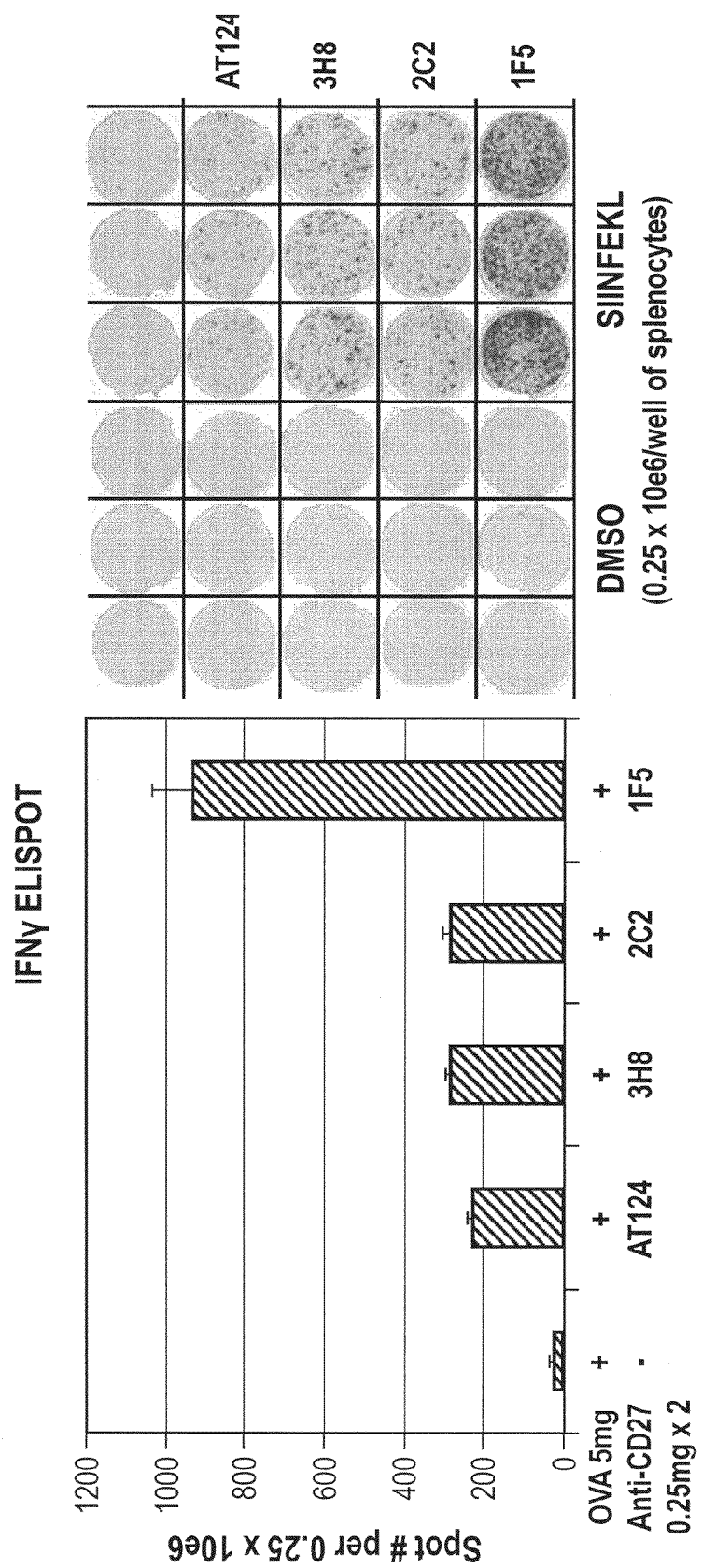
FIG. 20 depicts the results of an ELISPOT assay and enhanced IFNγ production using anti-CD27 antibodies.

Splenocytes ($2.5 \times 10^5$ and $0.5 \times 10^5$) from the pentamer staining preparation of Example 8 above were placed on an anti-IFNγ monoclonal antibody (mAb) coated plate in triplicate wells after RBC lysis. SIINFEKL (SEQ ID NO: 119) peptide was added at a final concentration of 2 µg/ml. A background control was set up for each sample in triplicate in the absence of peptide. The stimulation was maintained at 37° C. in a tissue culture incubator overnight. ELISPOT detection was performed using an ELISPOT kit (BD Biosciences) following the manufacturer's protocol. IFNγ-spot number was counted. Results are shown in FIGS. 20 and 21, from which it can be seen that anti-CD27 mAbs significantly enhanced T-cell activity.

Example 13

Anti-CD27 mAb Enhances T Cell Responses to a Vaccine Antigen

Figure 22:
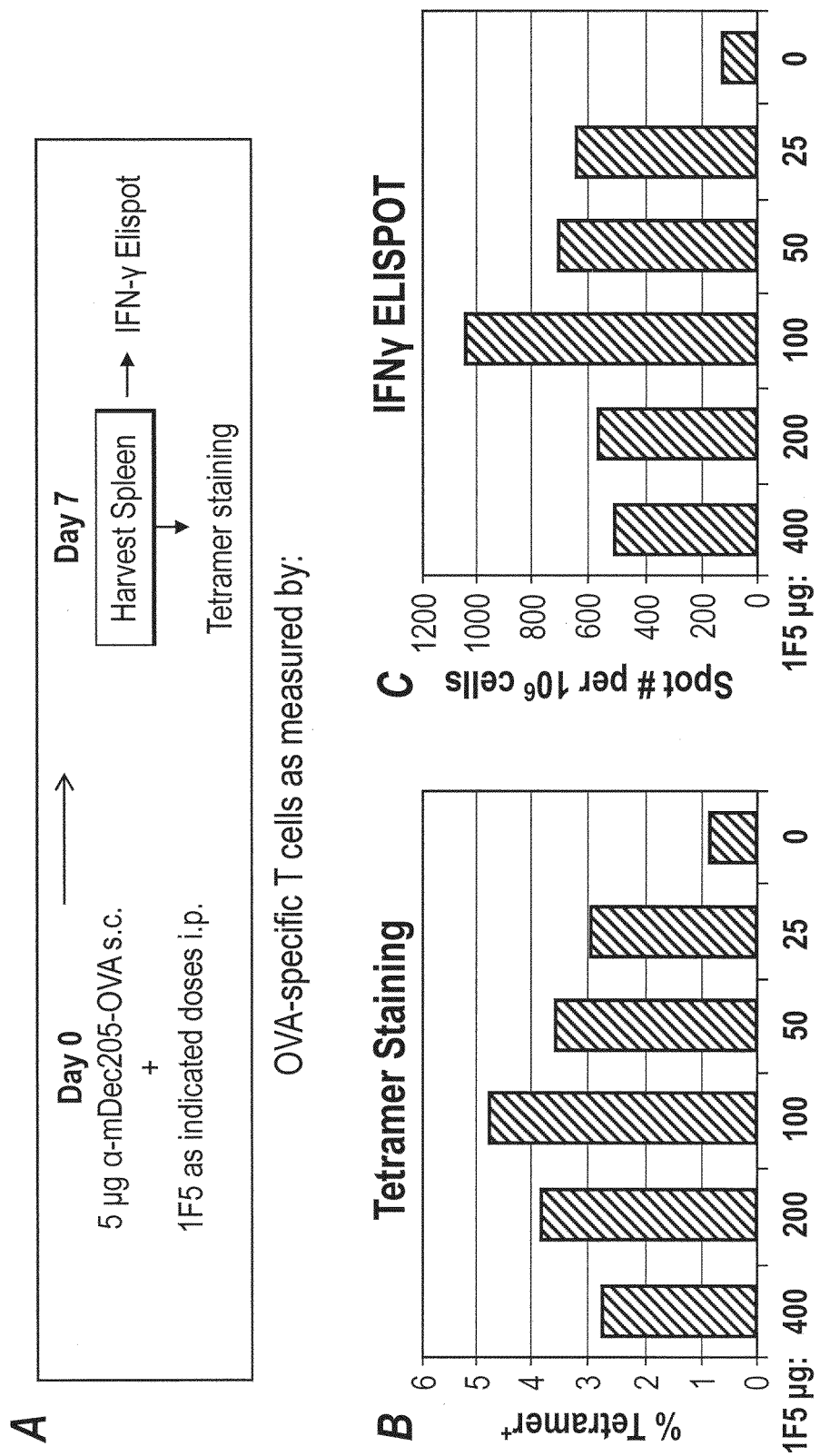
FIGS. 22A-C are the protocol for and results of an experiment showing that anti-CD27 enhances T cell responses to an APC-targeted vaccine (α-DEC205-OVA).

HuCD27 transgenic mice were immunized with 5 µh (s.c.) of the APC-targeted vaccine comprising an anti-mouse DEC-205 IgG antibody fused to ovalbumin (OVA) (referred to as α-mDEC-205-OVA), in combination with the anti-CD27 human mAb 1F5 (i.p.) at various doses (25, 50, 100, 200 or 400 µg). One week later splenocytes were analyzed for CD8+ T cell reactivity to the OVA SIINFEKL (SEQ ID NO: 119) peptide (OVA peptide 257-264) by tetramer staining (% tetramer positive of all CD8+ shown) and IFN-γ ELISPOT by the procedure as generally described in Examples 8 and 9 respectively. The results are shown in FIGS. 22A-C, wherein FIG. 22A shows the protocol used, FIG. 22B shows the results of the tetramer staining experiment and FIG. 22C shows the results of the IFN-gamma ELISPOT experiment. These results indicate that the co-administered human mAb 1F5 significantly enhanced the T-cell responses to the vaccine component administered.

Example 14

Synergistic Effect of Anti-CD27 mAb (1F5) and TLR Agonist (Poly IC) on T Cell Responses to Vaccine (Anti-DEC205-OVA)

huCD27-Tg (transgenic) and wild-type (WT) mouse littermates were intraperitoneally injected with anti-CD27 mAb 1F5 (50 µg) on day −3, and then subcutaneously via 4 paws injected with anti-mDec205-OVA (5 µg) plus Poly IC 0, 25, 50 or 100 µg on day 0, Spleens were collected on day 7 and assessed by tetramer staining, IFNγ-ELISPOT and IFNγ-ICS. Mean±SD of positive IFNγ-ICS among gated CD8 T cells from 3 mice per group were calculated and a panel of representative Dot Plots was collected. The results, shown in FIGS. 23A-D, indicate that the anti-CD27 human mAb acted synergistically with TLR3 agonist Poly IC to enhance the T-cell responses to the vaccine component administered.

Example 15

Figure 24:
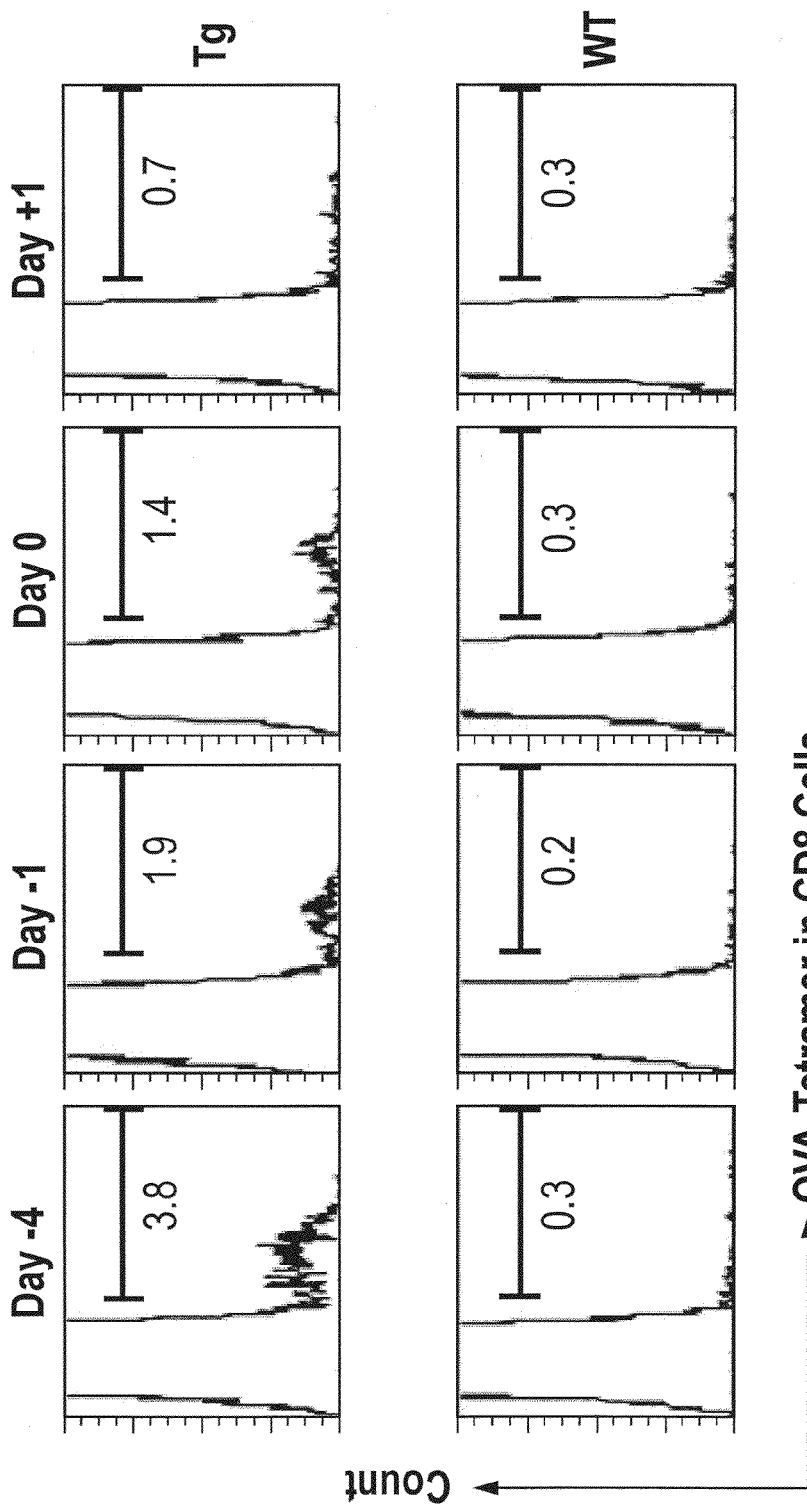
FIGS. 24 and 25 show results from a study of administration of ant-CD27 mAb prior to vaccine in the presence or absence of T:LR agonst and show the significance of timing of the aministration of the antibody relative to the vaccine.
Figure 25:
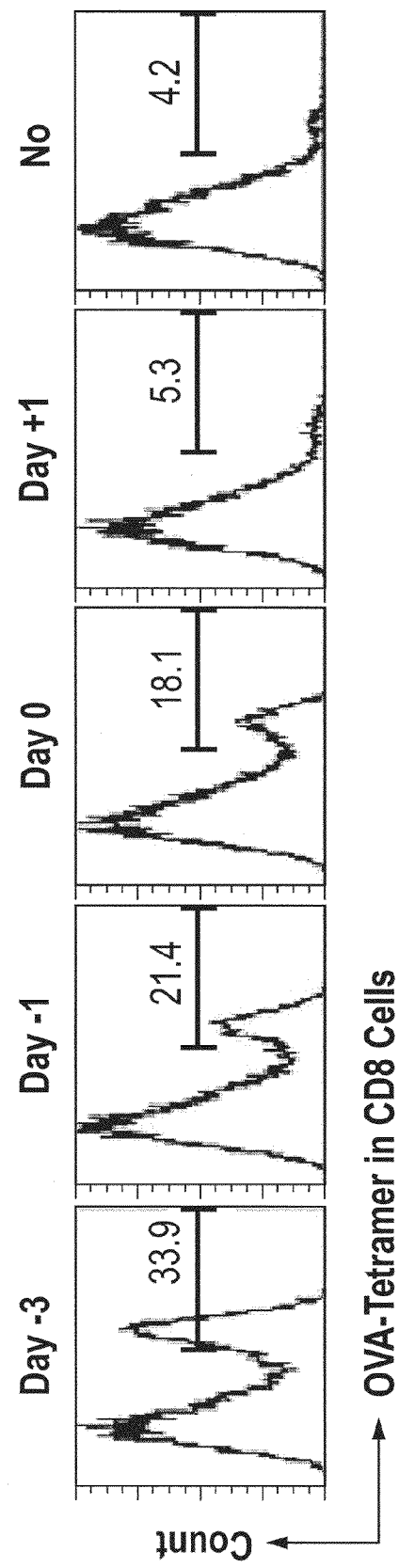
Figure 28:
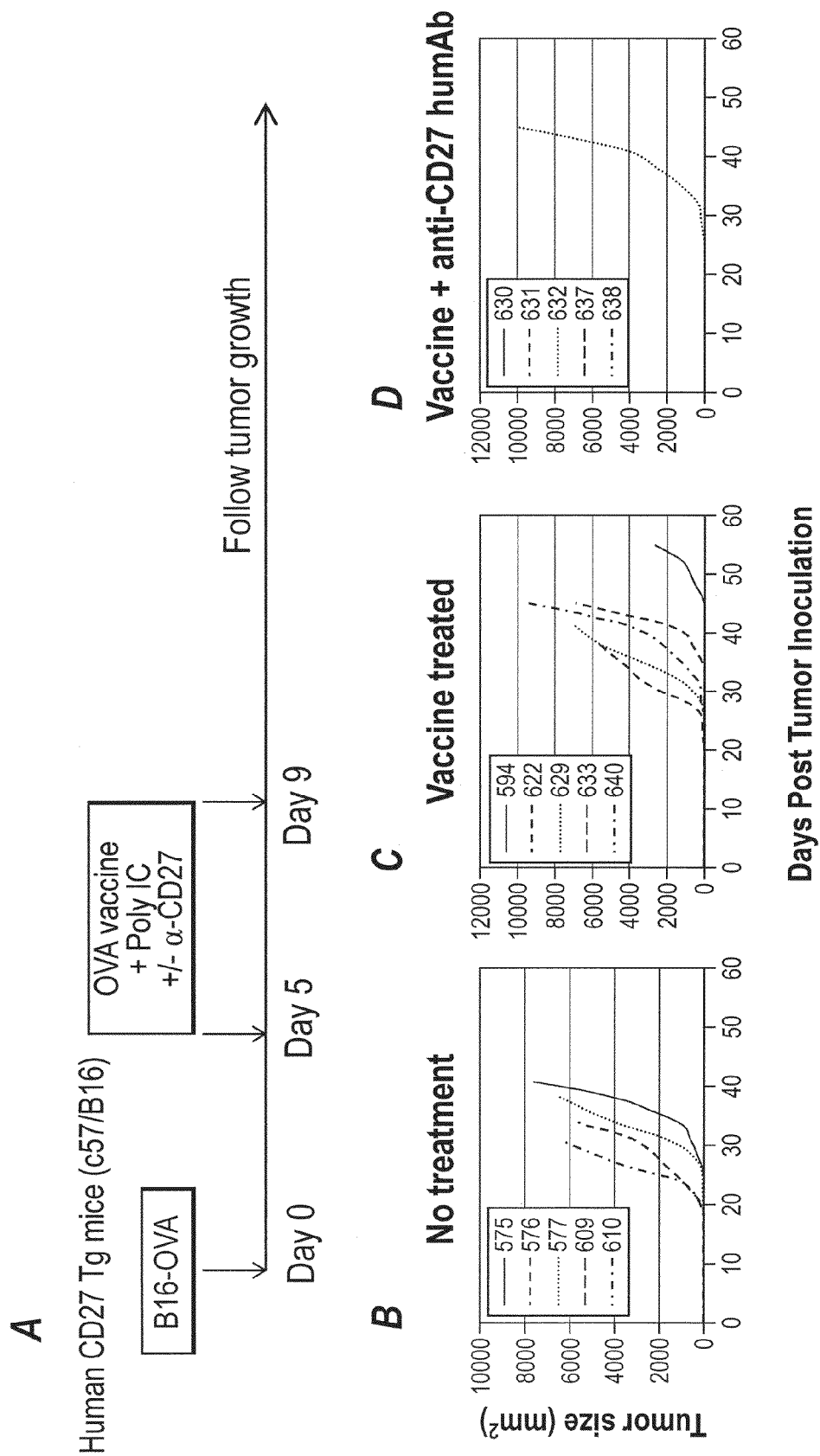
FIGS. 28A-D are the protocol for and results of an experiment showing that anti-CD27 enhances the efficacy of an α-DEC205-OVA vaccine in a MO4 (B16-OVA) melanoma challenge model.

Administration of Anti-CD27 mAb Prior to Dec205-Targeted Vaccine in the Absence or Presence of TLR Agonist huCD27-Tg mice and wild type (WT) littermates were intraperitoneally injected with anti-CD27 mAb (50 μg) on various days related to vaccine as indicated in FIG. 28, and subcutaneously via 4 paws injected with anti-mDec205-OVA (5 μg) plus or minus TLR agonist Poly IC-LC (20 μg) on day 0, Spleens were collected on day 7 and assessed by tetramer staining and IFNγ-ELISPOT. A representative panel of tetramer staining among gated CD8 T cells is shown in FIGS. 24 and 25. IFNγ-ELISPOT showed a similar pattern.

These results show that, surprisingly, when anti-CD27 antibody is administered in combination with a vaccine in the presence or absence of TLR agonist, T-cell activation is greater when the antibody is administered before the vaccine, for example a day or more before the vaccine (antigen) is administered.

Example 16

Figure 26:
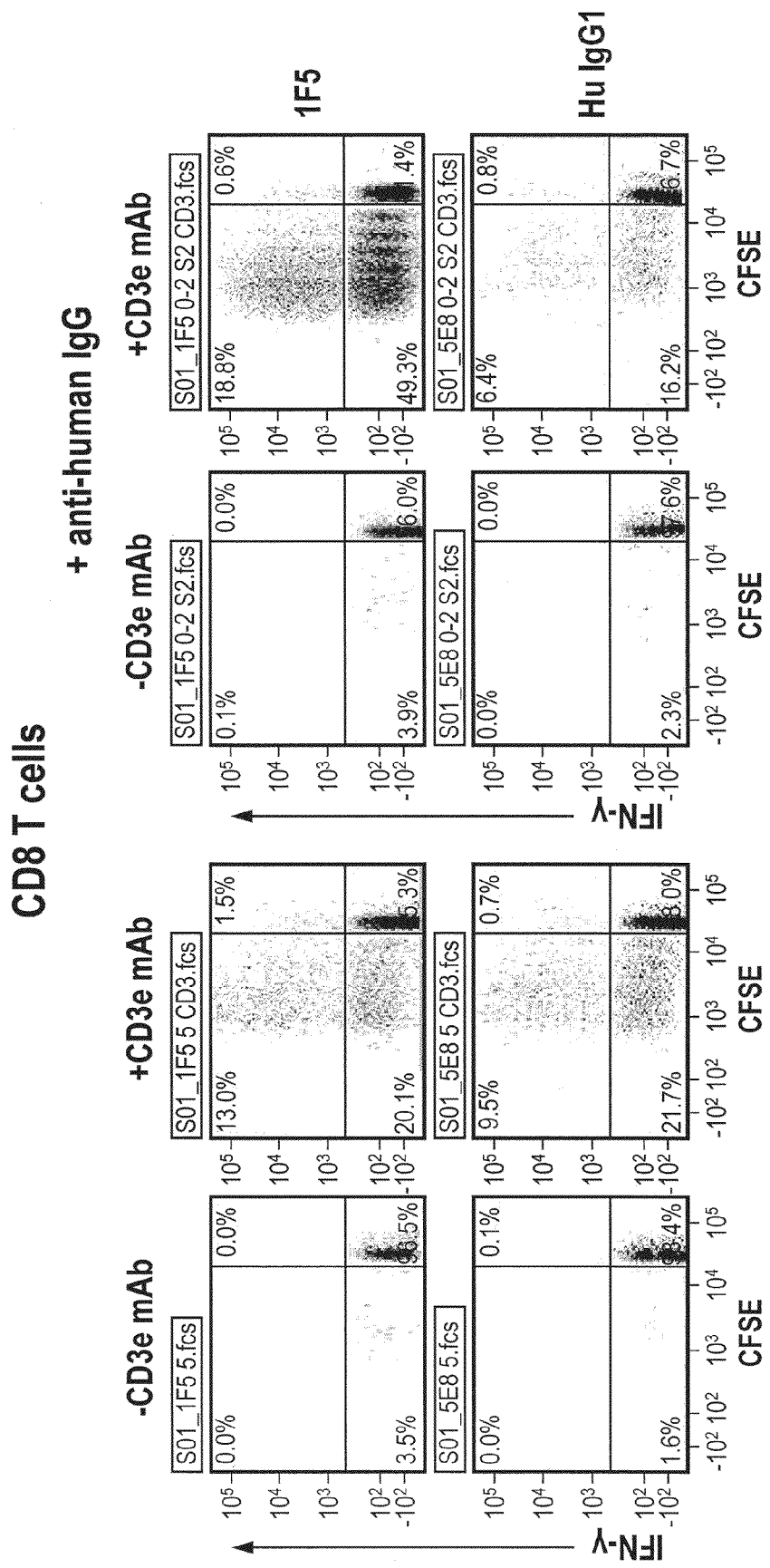
FIGS. 26 and 27 show results from administration of anti-CD27 mAb in combination with TCR activation ion T-cells from human CD27 transgenic mice, as shown by both proliferation and cytokine production.
Figure 27:
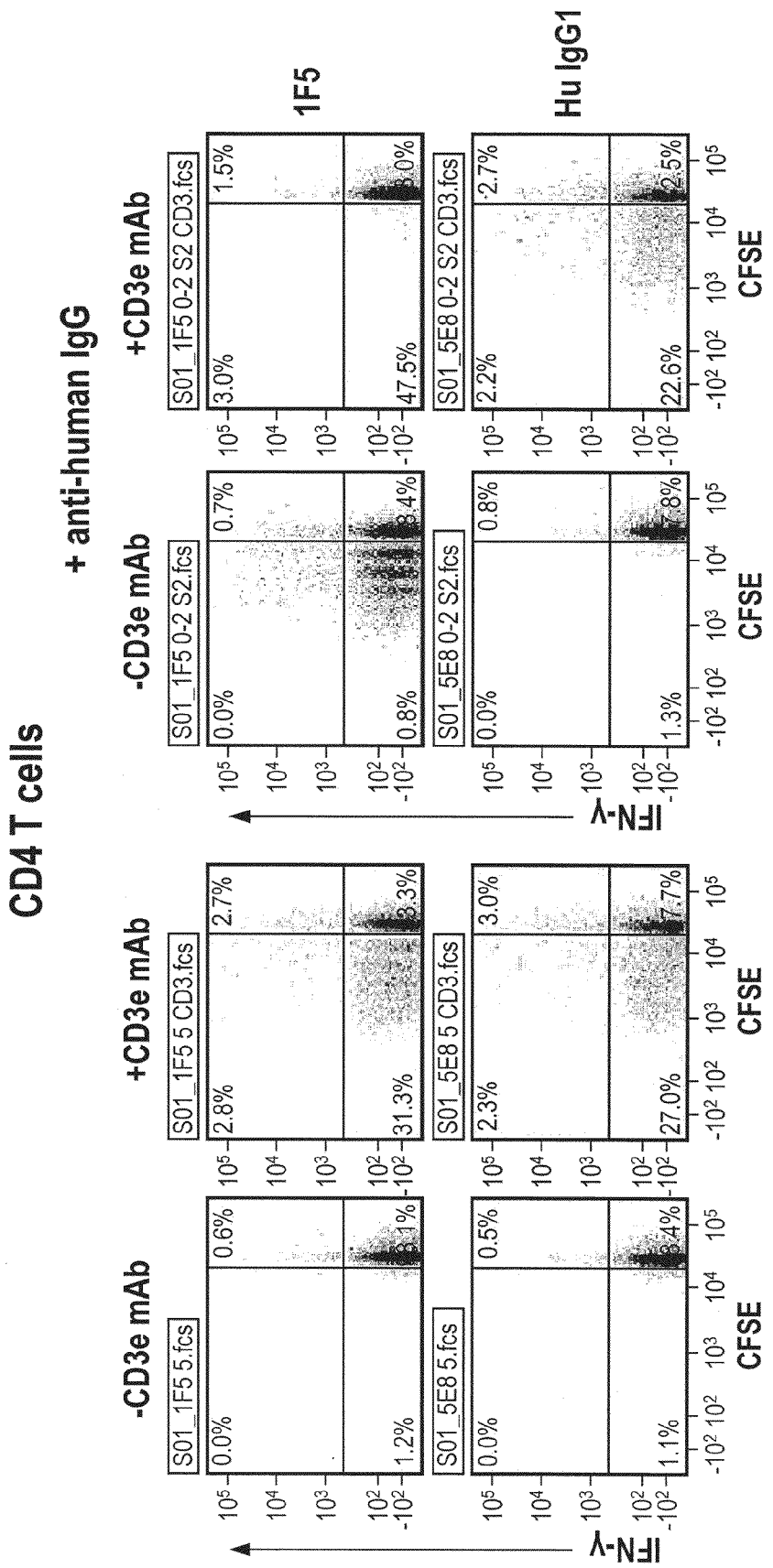

Anti-CD27 mAb Combined with TCR Activation Activates T-Cells from Human CD27 Transgenic Mice To assess the T cell activation capability of 1F5 mAb, T cells were purified from spleen of hCD27-Tg mice by negative selection with beads. Cells were labeled with CFSE and incubated with 0.2 μg/ml of anti-CD27 human mAb 1F5 or isotype control for 3 days. The cross-linking anti-human IgG was passed through an endotoxin removal column before use. IFNγ-ICS and CSFE dilution among CD8 and CD4 T cells are shown in FIGS. 26 and 27. TNFa-ICS showed the same pattern as IFNg. As shown in FIGS. 26 and 27, when combined with TCR activation, 1F5 mAb effectively induces proliferation and cytokine production from T cells in vitro. The data show that both cross-linking with anti-human IgG and T cell receptor activation with anti-CD3 mAb were required for 1F5 induced proliferation and cytokine production.

Example 17

Anti-CD27 mAb Enhances the Efficacy of Vaccine in a MO4 Melanoma Challenge Model To assess in vivo anti-tumor activity, huCD27-Tg and WT control, 8 mice per group, were subcutaneously inoculated with $0.3 \times 10^5$ MO4 cells on day 0. On day 5 and 12, these mice were intraperitoneally injected with anti-CD27 mAb 1F5 (50 μg); on day 8 and 15, additional doses of CD27 HuMab (50 μg) and vaccinated with anti-mDec205-OVA (5 μg). Tumor growth was measured with calipers 2 times a week. Results are shown in FIG. 24.

In a further study, huCD27-Tg and WT control, 5 mice per group, were subcutaneously inoculated with $1 \times 10^5$ MO4 cells on day 0. On day 5 and 12, these mice were vaccinated with anti-mDec205-OVA (5 μg) plus the TLR agonist Poly IC-LC (10 μg) intraperitoneally. On days 6 and 13, mice were injected with anti-CD27 mAb 1F5 (50 μg). Tumor growth was measured with calipers 2 times a week as indicated in the protocol illustrated in FIG. 28A. The results, shown in FIGS. 28B, C and D, show the effect of no treatment (FIG. 28B), vaccine treatment alone (FIG. 28C), or vaccine treatment in combination with anti-CD27 treatment (FIG. 28D) on tumor size in the mice as a function of the number of days post tumor inoculation. The results demonstrate that the combination treatment with anti-CD27 mAb (1F5) significantly prolonged survival of tumor challenged mice.

Example 18

1F5 Exhibits Potent Anti-Tumor Activity in a Syngeneic Transgenic Mouse Tumor Challenge Model of the $BCL_1$ B-Lymphoma To assess in vivo anti-tumor activity of 1F5, groups of 9-10 hCD27 transgenic mice (Balb/c background) were challenged with $10^7$ $BCL_1$ B-lymphoma cells administered intravenously on Day 0. Animals were then treated with 5 doses of anti-human CD27 mAb 1F5 as indicated. As shown in FIGS. 29A and 29B, significantly prolonged survival of tumor challenged mice, in a dose dependent manner.

Example 19

Tumor Killing in Raji Xenograph SCID Mouse Model

CB.17 SCID mice (purchased from Taconic) were maintained in a pathogen-free mouse facility. Lymphoma Raji cells ($1 \times 10^5$) were subcutaneously injected into SCID mice, 4 mice per group. On day 6, these mice were treated with CD27 human mAbs via intraperitoneal administration, 0.5 mg per dose and dosed twice a week for 3 weeks. Tumor growth was measured with calipers 3 times a week. Results of tumor growth and Kaplan-Meier analysis are shown in FIGS. 30A and 30B, from which is can be seen that the anti-CD27 mAbs significantly prolonged survival of the tumor challenged mice.

In a further experiment, CB.17 SCID mice (purchased from Taconic) were maintained in a pathogen-free mouse facility. Human lymphoma Raji cells ($5 \times 10^5$) were subcutaneously injected into SCID mice on day 0, 6 mice per group. On day 5, these mice were treated with anti-CD27 mAb 1F5 via intraperitoneal administration, 0.033, 0.1 or 0.3 mg per dose and dosed twice a week for 3 weeks. Tumor growth was measured with calipers 2 times a week.

Figure 31:
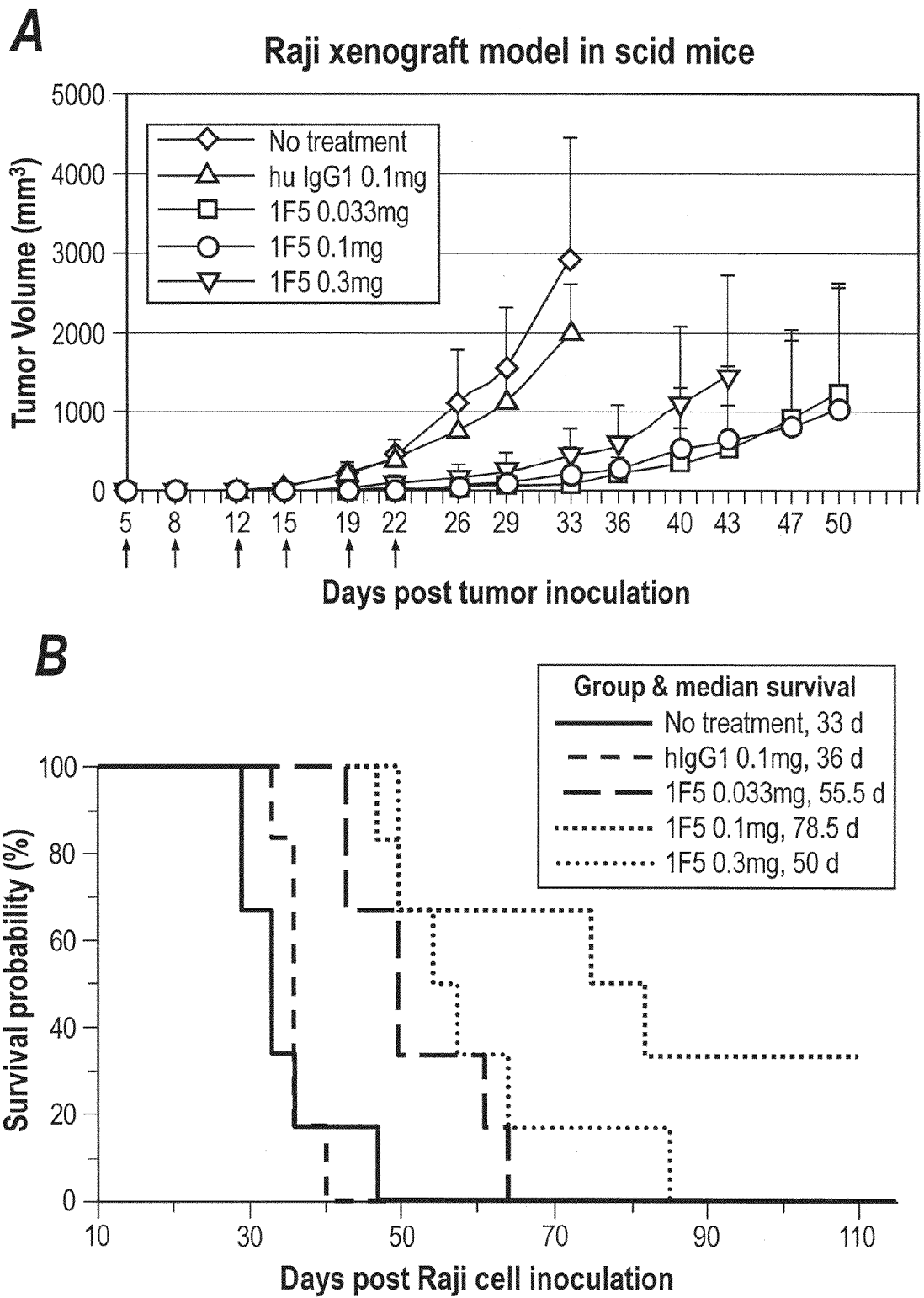
Figure 32:
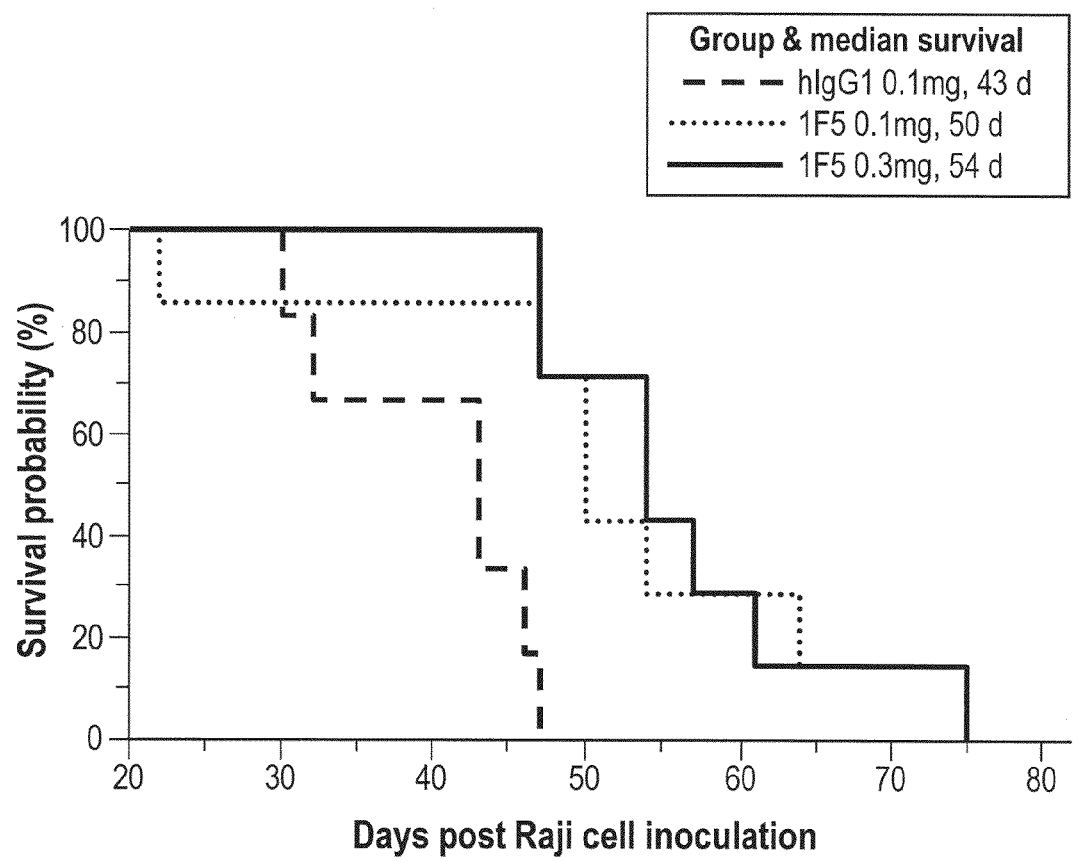

The results, shown in FIG. 31A, indicate that the anti-CD27 mAb (1F5) significantly inhibited tumor growth and thus significantly prolonged survival of the tumor challenged mice. A Kaplan-Meier survival plot of the data is also provided in FIG. 31B, which shows that median survival was increased by at least 10 days in mice from the treated group compared to the control group. A further xenograft experiment was conducted with 1G5 and results are shown in FIG. 32.

Example 20

Tumor Killing in Daudi Xenograft SCID Mouse Model

CB.17 SCID mice (purchased from Taconic) were maintained in a pathogen-free mouse facility. Human lymphoma Daudi cells ($1 \times 10^6$) were subcutaneously injected into SCID mice on day 0, 6 mice per group. On day 5, these mice were treated with anti-CD27 human mAb 1F5 via intraperitoneal administration, 0.033, 0.1 or 0.3 mg per dose and dosed twice a week for 3 weeks. Tumor growth was measured with calipers 2 times a week.

The results, shown in FIG. 33, indicate that the anti-CD27 mAb (1F5) significantly inhibited tumor growth (FIG. 33A) and thus significantly prolonged survival of the tumor challenged mice (Kaplan-Meier plot in FIG. 33B).

Example 21

Anti- CD27 mAb Engineered to not Bind Fc Receptors does not Enhance T Cell Responses to a Vaccine Antigen HuCD27 transgenic mice were immunized with 5 μg (s.c.) of APC-targeted vaccine comprising an anti-mouse DEC-205 IgG antibody fused to ovalbumin (OVA) (referred to as α-mDEC-205-OVA), in combination with the anti-CD27 human mAb 1F5 (i.p.) or mAb 1F5 mutant (Fc portion mutated to prevent Fc receptor binding) or control IgG mAb. One week later, splenocytes were analyzed for CD8+ T cell reactivity to the OVA SIINFEKL (SEQ ID NO: 119) peptide (OVA peptide 257-264) by IFN-γ ELISPOT by the procedure as generally described.

Figure 34:
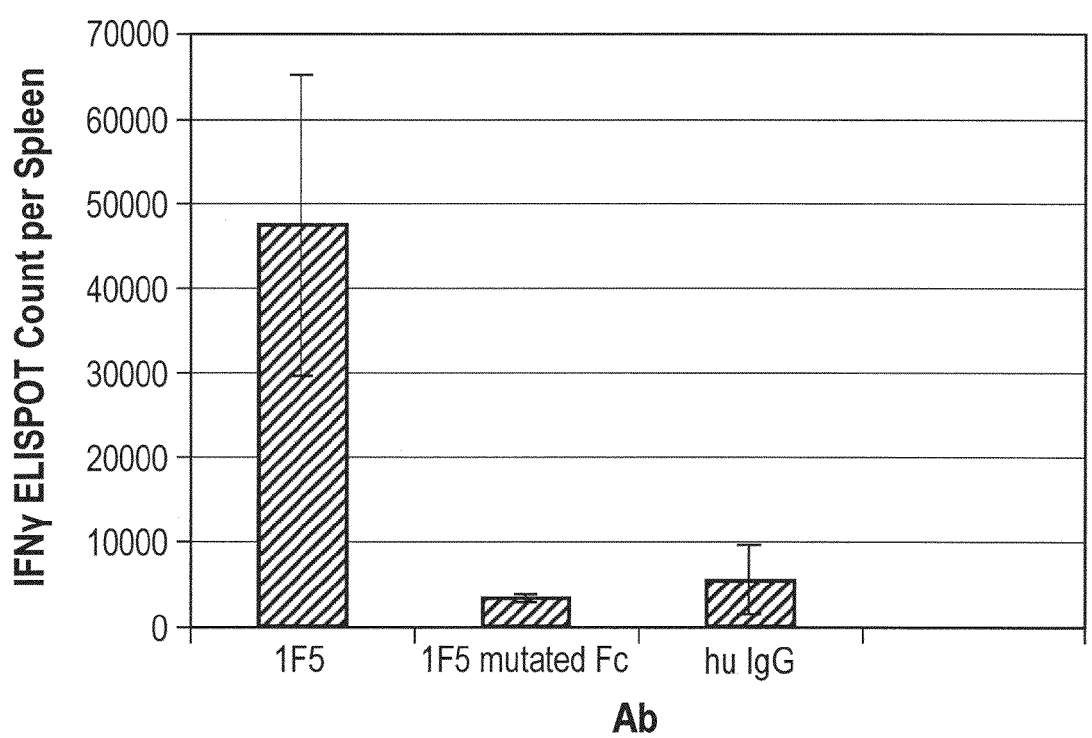
FIG. 34 shows the results of an ELISPOT assay and that enhanced antigen-specific IFNg production using anti-CD27 antibody is abrogated when the Fc portion of the IgG is unable to engage Fc receptors.

The results, shown in FIG. 34, demonstrate that the altered human mAb 1F5 does not enhance the T-cell responses to the vaccine, and thus would be an effective agent for blocking the CD70/CD27 pathway.

EQUIVALENTS

Those skilled in the art will recognize, or be able to ascertain using no more than routine experimentation, many equivalents of the specific embodiments of the invention described herein. Such equivalents are intended to be encompassed by the following claims.

SUMMARY OF SEQUENCE LISTING

| SEQ ID NO: | DESCRIPTION |
| --- | --- |
| 1 | Human CD27 (GenBank Accession No.: AAH12160.1) |
| 2 | Human CD70 (GenBank Accession No.: NP_001243) |
| 3 | $V_H$ 3-33 germline sequence is provided (Genbank Accession No AAP44382) |
| 4 | $V_H$ 3-7 germline sequence is provided (Genbank Accession No AAP44389) |
| 5 | 3H8-1B11 VH nucleic acid |
| 6 | 3H8-1B11 VH amino acid including signal peptide |
| 7 | 3H8-1B11 VH "mature" amino acid excluding signal peptide |
| 8 | 3H8-1B11 VH CDR1 amino acid |
| 9 | 3H8-1B11 VH CDR2 amino acid |
| 10 | 3H8-1B11 VH CDR3 amino acid |
| 11 | 3H8-1B11 VL #2 nucleic acid |
| 12 | 3H8-1B11 VL #2 amino acid including signal peptide |
| 13 | 3H8-1B11 VL #2 "mature" amino acid excluding signal peptide |
| 14 | 3H8-1B11 VL #2 CDR1 amino acid |
| 15 | 3H8-1B11 VL #2 CDR2 amino acid |
| 16 | 3H8-1B11 VL #2 CDR3 amino acid |
| 17 | 3H8-1B11 VL #3 nucleic acid |
| 18 | 3H8-1B11 VL #3 amino acid including signal peptide |
| 19 | 3H8-1B11 VL #3 "mature" amino acid excluding signal peptide |
| 20 | 3H8-1B11 VL #3 CDR1 amino acid |
| 21 | 3H8-1B11 VL #3 CDR2 amino acid |
| 22 | 3H8-1B11 VL #3 CDR3 amino acid |
| 23 | 2C2-1A10 VH nucleic acid |
| 24 | 2C2-1A10 VH amino acid including signal peptide |
| 25 | 2C2-1A10 VH "mature" amino acid excluding signal peptide |
| 26 | 2C2-1A10 VH CDR1 amino acid |
| 27 | 2C2-1A10 VH CDR2 amino acid |
| 28 | 2C2-1A10 VH CDR3 amino acid |
| 29 | 2C2-1A10 VL nucleic acid |
| 30 | 2C2-1A10 VL amino acid including signal peptide |
| 31 | 2C2-1A10 VL "mature" amino acid excluding signal peptide |
| 32 | 2C2-1A10 VL CDR1 amino acid |
| 33 | 2C2-1A10 VL CDR2 amino acid |
| 34 | 2C2-1A10 VL CDR3 amino acid |
| 35 | 1F5-1H5 VH nucleic acid |
| 36 | 1F5-1H5 VH amino acid including signal peptide |
| 37 | 1F5-1H5 VH "mature" amino acid excluding signal peptide |
| 38 | 1F5-1H5 VH CDR1 amino acid |
| 39 | 1F5-1H5 VH CDR2 amino acid |
| 40 | 1F5-1H5 VH CDR3 amino acid |
| 41 | 1F5-1H5 VL #2 nucleic acid |
| 42 | 1F5-1H5 VL #2 amino acid including signal peptide |
| 43 | 1F5-1H5 VL #2 "mature" amino acid excluding signal peptide |
| 44 | 1F5-1H5 VL #1 CDR1 amino acid |
| 45 | 1F5-1H5 VL #2 CDR2 amino acid |
| 46 | 1F5-1H5 VL #2 CDR3 amino acid |
| 47 | 1H8-B4 VH nucleic acid |
| 48 | 1H8-B4 VH amino acid including signal peptide |
| 49 | 1H8-B4 VH "mature" amino acid excluding signal peptide |
| 50 | 1H8-B4 VH CDR1 amino acid |
| 51 | 1H8-B4 VH CDR2 amino acid |
| 52 | 1H8-B4 VH CDR3 amino acid |
| 53 | 1H8-B4 VL nucleic acid |

SUMMARY OF SEQUENCE LISTING

| SEQ ID NO: | DESCRIPTION |
|---|---|
| 54 | 1H8-B4 VL amino acid including signal peptide |
| 55 | 1H8-B4 VL "mature" amino acid excluding signal peptide |
| 56 | 1H8-B4 VL CDR1 amino acid |
| 57 | 1H8-B4 VL CDR2 amino acid |
| 58 | 1H8-B4 VL CDR3 amino acid |
| 59 | 1G5-1B9 VH nucleic acid |
| 60 | 1G5-1B9 VH amino acid including signal peptide |
| 61 | 1G5-1B9 VH "mature" amino acid excluding signal peptide |
| 62 | 1G5-1B9 VH CDR1 amino acid |
| 63 | 1G5-1B9 VH CDR2 amino acid |
| 64 | 1G5-1B9 VH CDR3 amino acid |
| 65 | 1G5-1B9 VL nucleic acid |
| 66 | 1G5-1B9 VL amino acid including signal peptide |
| 67 | 1G5-1B9 VL "mature" amino acid excluding signal peptide |
| 68 | 1G5-1B9 VL CDR1 amino acid |
| 69 | 1G5-1B9 VL CDR2 amino acid |
| 70 | 1G5-1B9 VL CDR3 amino acid |
| 71 | 2G9-1D11 VH nucleic acid |
| 72 | 2G9-1D11 VH amino acid including signal peptide |
| 73 | 2G9-1D11 VH "mature" amino acid excluding signal peptide |
| 74 | 2G9-1D11 VH CDR1 amino acid |
| 75 | 2G9-1D11 VH CDR2 amino acid |
| 76 | 2G9-1D11 VH CDR3 amino acid |
| 77 | 2G9-1D11 VL nucleic acid |
| 78 | 2G9-1D11 VL amino acid including signal peptide |
| 79 | 2G9-1D11 VL "mature" amino acid excluding signal peptide |
| 80 | 2G9-1D11 VL CDR1 amino acid |
| 81 | 2G9-1D11 VL CDR2 amino acid |
| 82 | 2G9-1D11 VL CDR3 amino acid |
| 83 | 3A10-1G10 VH nucleic acid |
| 84 | 3A10-1G10 VH amino acid including signal peptide |
| 85 | 3A10-1G10 VH "mature" amino acid excluding signal peptide |
| 86 | 3A10-1G10 VH CDR1 amino acid |
| 87 | 3A10-1G10 VH CDR2 amino acid |
| 88 | 3A10-1G10 VH CDR3 amino acid |
| 89 | 3A10-1G10 VL #1 nucleic acid |
| 90 | 3A10-1G10 VL #1 amino acid including signal peptide |
| 91 | 3A10-1G10 VL #1 "mature" amino acid excluding signal peptide |
| 92 | 3A10-1G10 VL #1 CDR1 amino acid |
| 93 | 3A10-1G10 VL #1 CDR2 amino acid |
| 94 | 3A10-1G10 VL #1 CDR3 amino acid |
| 95 | 3A10-1G10 VL #4 nucleic acid |
| 96 | 3A10-1G10 VL #4 amino acid including signal peptide |
| 97 | 3A10-1G10 VL #4 "mature" amino acid excluding signal peptide |
| 98 | 3A10-1G10 VL #4 CDR1 amino acid |
| 99 | 3A10-1G10 VL #4 CDR2 amino acid |
| 100 | 3A10-1G10 VL #4 CDR3 amino acid |
| 101 | 3H12-1E12 VH nucleic acid |
| 102 | 3H12-1E12 VH amino acid including signal peptide |
| 103 | 3H12-1E12 VH "mature" amino acid excluding signal peptide |
| 104 | 3H12-1E12 VH CDR1 amino acid |
| 105 | 3H12-1E12 VH CDR2 amino acid |
| 106 | 3H12-1E12 VH CDR3 amino acid |
| 107 | 3H12-1E12 VL #2 nucleic acid |
| 108 | 3H12-1E12 VL #2 amino acid including signal peptide |
| 109 | 3H12-1E12 VL #2 "mature" amino acid excluding signal peptide |
| 110 | 3H12-1E12 VL #2 CDR1 amino acid |
| 111 | 3H12-1E12 VL #2 CDR2 amino acid |
| 112 | 3H12-1E12 VL #2 CDR3 amino acid |
| 113 | VH CDR3 consensus |
| 114 | VL CDR3 consensus |
| 115 | VH CDR2 consensus |
| 116 | VL CDR2 consensus |
| 117 | VH CDR1 consensus |
| 118 | VL CDR1 consensus |

The invention claimed is:

1. An isolated monoclonal antibody which binds to human CD27, wherein the antibody comprises:
   a heavy chain variable region CDR1 comprising SEQ ID NO: 38;
   a heavy chain variable region CDR2 comprising SEQ ID NO: 39;
   a heavy chain variable region CDR3 comprising SEQ ID NO: 40;
   a light chain variable region CDR1 comprising SEQ ID NO: 44;
   a light chain variable region CDR2 comprising SEQ ID NO: 45; and
   a light chain variable region CDR3 comprising SEQ ID NO: 46.

2. An isolated monoclonal antibody which binds to human CD27 and comprises a heavy chain variable region comprising SEQ ID NO:37.

3. An isolated monoclonal antibody which binds to human CD27 and comprises a light chain variable region comprising SEQ ID NO:43.

4. An isolated monoclonal antibody which binds to human CD27 and comprises a heavy chain variable region comprising SEQ ID NO:37 and a light chain variable region comprising SEQ ID NO:43.

5. An isolated monoclonal antibody that binds human CD27, wherein the antibody comprises a heavy chain variable region and a light chain variable region encoded by nucleotide sequences set forth in SEQ ID NOs:35 and 41, respectively.

6. A composition comprising the antibody of claim 1 and a carrier.

7. The composition of claim 6, further comprising an adjuvant.

8. The composition of claim 6, further comprising an immunostimulatory agent.

9. The composition of claim 8, wherein the immunostimulatory agent is selected from the group consisting of CD40 ligand, FLT 3 ligand, cytokines, colony-stimulating factors, an anti-CTLA-4 antibody, LPS (endotoxin), ssRNA, dsRNA, Bacille Calmette-Guerin (BCG), Levamisole hydrochloride, intravenous immune globulins and a Toll-like Receptor (TLR) agonist.

10. The composition of claim 9, wherein the Toll-like Receptor agonist is selected from the group consisting of a TLR3 agonist, a TLR4 agonist, a TLR5 agonist, a TLR7 agonist, a TLR8 agonist, and a TLR 9 agonist.

11. The composition of claim 6, further comprising an immunosuppressive agent.

12. The composition of claim 6, further comprising another antibody.

13. The composition of claim 6, further comprising an antigen.

14. The composition of claim 13, wherein the antigen comprises a tumor antigen, allergen or an autoantigen.

15. The composition of claim 14, wherein the tumor antigen is selected from the group consisting of βhCG, gp100 or Pme117, HER2/neu, WT1, mesothelin, CEA, gp100, MART1, TRP-2, melan-A, NY-ESO-1, NY-BR-1, NY-CO-58, MN (gp250), idiotype, MAGE-1, MAGE-3, MAGE-A3, Tyrosinase, Telomerase, SSX2 antigens, MUC-1 antigens, and germ cell derived tumor antigens.

16. A bispecific antibody comprising the antibody of claim 1 linked to a second molecule having a binding specificity which is different from the antibody.

17. The bispecific molecule of claim 16, wherein the second molecule binds to a T cell receptor.

18. The bispecific molecule of claim 17, wherein the T cell receptor is selected from the group consisting of CD3, CD40 and CD25.

19. The bispecific molecule of claim 16, wherein the second molecule binds to an NK receptor.

* * * * *

SEQUENCE LISTING

```
<160> NUMBER OF SEQ ID NOS: 120

<210> SEQ ID NO 1
<211> LENGTH: 260
<212> TYPE: PRT
```

<213> ORGANISM: Homo sapiens

<400> SEQUENCE: 1

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
                20                  25                  30

Trp Ala Gln Gly Lys Leu Cys Cys Gln Met Cys Glu Pro Gly Thr Phe
            35                  40                  45

Leu Val Lys Asp Cys Asp Gln His Arg Lys Ala Ala Gln Cys Asp Pro
        50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
                100                 105                 110

Arg Asp Lys Glu Cys Thr Glu Cys Asp Pro Leu Pro Asn Pro Ser Leu
            115                 120                 125

Thr Ala Arg Ser Ser Gln Ala Leu Ser Pro His Pro Gln Pro Thr His
        130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260

<210> SEQ ID NO 2
<211> LENGTH: 193
<212> TYPE: PRT
<213> ORGANISM: Homo sapiens

<400> SEQUENCE: 2

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
            35                  40                  45

Pro Leu Glu Ser Leu Gly Trp Asp Val Ala Glu Leu Gln Leu Asn His
        50                  55                  60

Thr Gly Pro Gln Gln Asp Pro Arg Leu Tyr Trp Gln Gly Gly Pro Ala
65                  70                  75                  80

```
Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
            115                 120                 125

Ala Val Gly Ile Cys Ser Pro Ala Ser Arg Ser Ile Ser Leu Leu Arg
            130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
                180                 185                 190

Pro
```

```
<210> SEQ ID NO 3
<211> LENGTH: 97
<212> TYPE: PRT
<213> ORGANISM: Homo sapiens

<400> SEQUENCE: 3

Val Gln Leu Val Glu Ser Gly Gly Val Val Gln Pro Gly Arg Ser
1               5                   10                  15

Leu Arg Leu Ser Cys Ala Ala Ser Gly Phe Thr Phe Ser Thr Tyr Gly
                20                  25                  30

Met His Trp Val Arg Gln Ala Pro Gly Lys Gly Leu Glu Trp Val Ala
            35                  40                  45

Ile Ile Trp Phe Asp Gly Ser Asn Thr Tyr Tyr Ala Asp Ser Val Arg
50                  55                  60

Gly Arg Phe Thr Ile Ser Arg Asp Ser Ser Lys Thr Leu Tyr Leu
65                  70                  75                  80

Glu Met Lys Ser Leu Arg Val Glu Asp Thr Ala Val Tyr Tyr Cys Ala
                85                  90                  95

Lys
```

```
<210> SEQ ID NO 4
<211> LENGTH: 97
<212> TYPE: PRT
<213> ORGANISM: Homo sapiens

<400> SEQUENCE: 4

Val Gln Leu Val Glu Ser Gly Gly Leu Val Gln Pro Gly Gly Ser
1               5                   10                  15

Leu Arg Leu Ser Cys Ala Ala Ser Gly Phe Thr Phe Ser Asn Ser Tyr
                20                  25                  30

Met Thr Trp Val Arg Gln Ala Pro Gly Lys Gly Leu Glu Trp Val Ala
            35                  40                  45

Asn Ile Lys Pro Asp Gly Ser Asp Lys Asn Tyr Ile Asn Ser Val Arg
50                  55                  60

Gly Arg Phe Thr Ile Ser Arg Asp Asn Ala Glu Lys Ser Ser Tyr Leu
65                  70                  75                  80

Gln Met Asn Ser Leu Arg Ala Glu Asp Thr Ala Ile Tyr Tyr Cys Val
                85                  90                  95

Thr
```

-continued

<210> SEQ ID NO 5
<211> LENGTH: 414
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atggagttgg ggctgagctg ggttttcctt gttgctattt tagaaggtgt ccagtgtgag      60
gtgcagctgg tggagtctgg gggaggcttg gtccagcctg gggggtccct gagactctcc     120
tgtgcagcct ctggattcac ctttagtagt tattggatgg cctgggtccg ccaggctcca     180
gggaaagggc tggagtggct gggcaatata aagcaagatg gaagtgagaa atactatgtg     240
gactctgtga agggccgatt caccatctcc agagacaacg ccaagaactc actgtatcta     300
caaatgaaca gcctgagagc cgaggacacg gctgtgtatt actgtgtgag ggaactgggg     360
atggactggt acttcgatct ctggggccgt ggcaccctgg tcactgtctc ctca           414

<210> SEQ ID NO 6
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Trp Met Ala Trp Val Arg Gln Ala Pro Gly Lys Gly Leu
    50                  55                  60

Glu Trp Leu Gly Asn Ile Lys Gln Asp Gly Ser Glu Lys Tyr Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Val Arg Glu Leu Gly Met Asp Trp Tyr Phe Asp Leu Trp
        115                 120                 125

Gly Arg Gly Thr Leu Val Thr Val Ser Ser
    130                 135

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Trp Met Ala Trp Val Arg Gln Ala Pro Gly Lys Gly Leu Glu Trp Leu
        35                  40                  45
Gly Asn Ile Lys Gln Asp Gly Ser Glu Lys Tyr Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Val Arg Glu Leu Gly Met Asp Trp Tyr Phe Asp Leu Trp Gly Arg Gly
            100                 105                 110
Thr Leu Val Thr Val Ser Ser
        115
```

```
<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Phe Thr Phe Ser Ser Tyr Trp
1               5
```

```
<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Lys Gln Asp Gly Ser Glu Lys
1               5
```

```
<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Arg Glu Leu Gly Met Asp Trp Tyr Phe Asp Leu
1               5                   10
```

```
<210> SEQ ID NO 11
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atggaagccc cagctcagct tctcttcctc ctgctactct ggctcccaga taccaccgga    60
gaaattgtgt tgacacagtc tccagccacc ctgtctttgt ctccagggga aagagccacc   120
ctctcctgca gggccagtca gagtgttgac agctacttag cctggtacca acagaaacct   180
ggccaggctc ccaggctcct catctatgat gcatccaaca gggccactgg catcccagcc   240
```

```
aggttcagtg gcagtgggtc tgggacagac ttcactctca ccatcagcaa cctagagcct    300
gaagattttg cagtttatta ctgtcagcag cgtagcaact ggcctccgac gttcggccaa    360
gggaccaagg tggaaatcaa a                                              381
```

```
<210> SEQ ID NO 12
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Asp Ser Tyr Leu Ala Trp Tyr Gln Gln Lys Pro Gly Gln Ala Pro
50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Asn Leu Glu Pro Glu Asp Phe Ala Val Tyr Tyr Cys Gln Gln Arg Ser
            100                 105                 110

Asn Trp Pro Pro Thr Phe Gly Gln Gly Thr Lys Val Glu Ile Lys
        115                 120                 125

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Asn Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 14
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 14

Gln Ser Val Asp Ser Tyr
1               5

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Ala Ser
1

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Arg Ser Asn Trp Pro Pro Thr
1               5

<210> SEQ ID NO 17
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atggaagccc cagctcagct tctcttcctc ctgctactct ggctcccaga taccaccgga      60
gaaattgtgt tgacacagtc tccagccacc ctgtctttgt ctccagggga aagagccacc     120
ctctcctgca gggccagtca gagtgttagc agctacttag cctggtacca acagaaacct     180
ggccaggctc ccaggctcct catctatgat gcatccagca gggccactgg catcccagac     240
aggttcagtg gcagtgggtc tgggacagac ttcactctca ccatcagcag actggagcct     300
gaagattttg cagtgtatta ctgtcagcag cgtagcaact ggcctccgac gttcggccaa     360
gggaccaagg tggaaatcaa a                                               381

<210> SEQ ID NO 18
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
                20                  25                  30
```

```
Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
 50                  55                  60

Arg Leu Leu Ile Tyr Asp Ala Ser Ser Arg Ala Thr Gly Ile Pro Asp
 65                  70                  75                  80

Arg Phe Ser Gly Ser Gly Ser Gly Thr Asp Phe Thr Leu Thr Ile Ser
                 85                  90                  95

Arg Leu Glu Pro Glu Asp Phe Ala Val Tyr Tyr Cys Gln Gln Arg Ser
            100                 105                 110

Asn Trp Pro Pro Thr Phe Gly Gln Gly Thr Lys Val Glu Ile Lys
        115                 120                 125
```

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Ser Arg Ala Thr Gly Ile Pro Asp Arg Phe Ser Gly
     50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gln Gly Thr Lys Val Glu Ile Lys
            100                 105
```

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Gln Ser Val Ser Ser Tyr
 1               5
```

<210> SEQ ID NO 21
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Asp Ala Ser
 1
```

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Gln Gln Arg Ser Asn Trp Pro Pro Thr
1               5

<210> SEQ ID NO 23
<211> LENGTH: 405
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23
atggagtttg ggctgagctg ggttttcctc gttgctcttt taagaggtgt ccagtgtcag      60
gtgcaactgg tggagtctgg gggaggcgtg gtccagcctg gaggtccct gcgactctcc     120 tgtgcagcgt ctggattcac cttcagtagc tatgacatac actgggtccg ccaggctcca     180
ggcaaggggc tggagtgggt ggcagttata tggaatgatg gaagtaataa atactatgca     240
gactccgtga agggccgatt caccatctcc agagacaatt ccacgaactc gctgtttctg     300
caaatgaaca gcctgagagc cgaggacacg gctgtgtatt attgtgtggg aggaactgct     360
gaccttgaac actgggacca gggaaccctg gtcaccgtct cctca                    405

<210> SEQ ID NO 24
<211> LENGTH: 135
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Asp Ile His Trp Val Arg Gln Ala Pro Gly Lys Gly Leu
    50                  55                  60

Glu Trp Val Ala Val Ile Trp Asn Asp Gly Ser Asn Lys Tyr Tyr Ala
65                  70                  75                  80

Asp Ser Val Lys Gly Arg Phe Thr Ile Ser Arg Asp Asn Ser Thr Asn
                85                  90                  95

Ser Leu Phe Leu Gln Met Asn Ser Leu Arg Ala Glu Asp Thr Ala Val
            100                 105                 110

Tyr Tyr Cys Val Gly Gly Thr Ala Asp Leu Glu His Trp Asp Gln Gly
        115                 120                 125

Thr Leu Val Thr Val Ser Ser
    130                 135

<210> SEQ ID NO 25
<211> LENGTH: 116

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Pro Gly Lys Gly Leu Glu Trp Val
        35                  40                  45

Ala Val Ile Trp Asn Asp Gly Ser Asn Lys Tyr Tyr Ala Asp Ser Val
    50                  55                  60

Lys Gly Arg Phe Thr Ile Ser Arg Asp Asn Ser Thr Asn Ser Leu Phe
65                  70                  75                  80

Leu Gln Met Asn Ser Leu Arg Ala Glu Asp Thr Ala Val Tyr Tyr Cys
                85                  90                  95

Val Gly Gly Thr Ala Asp Leu Glu His Trp Asp Gln Gly Thr Leu Val
            100                 105                 110

Thr Val Ser Ser
        115

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Phe Thr Phe Ser Ser Tyr Asp
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ile Trp Asn Asp Gly Ser Asn Lys
1               5

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Val Gly Gly Thr Ala Asp Leu Glu His Trp Asp Gln
1               5                   10

<210> SEQ ID NO 29
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
atgagggtcc tcgctcagct cctggggctc ctgctgctct gtttcccagg tgccagatgt    60
gacatccaga tgacccagtc tccatcctca ctgtctgcat ctgtaggaga cagagtcacc   120
atcacttgtc gggcgagtca gggtattagc agctggttag cctggtatca gcagaaacca   180
gagaaagccc ctaagtccct gatctatgct gcatccagtt tgcaaagtgg ggtcccatca   240
aggttcagcg gcagtggatc tgggacagat ttcactctca ccatcagcag cctgcagcct   300
gaagattttg caacttatta ctgccaacag tataatagtt accctctcac tttcggcgga   360
gggaccaagg tggagatcaa a                                             381
```

<210> SEQ ID NO 30
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Met Arg Val Leu Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser Ser Trp Leu Ala Trp Tyr Gln Gln Lys Pro Glu Lys Ala Pro
    50                  55                  60

Lys Ser Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Asn
            100                 105                 110

Ser Tyr Pro Leu Thr Phe Gly Gly Gly Thr Lys Val Glu Ile Lys
        115                 120                 125
```

<210> SEQ ID NO 31
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys
            100                 105

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gly Ile Ser Ser Trp
1               5

<210> SEQ ID NO 33
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Ala Ser
1

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Gln Tyr Asn Ser Tyr Pro Leu Thr
1               5

<210> SEQ ID NO 35
<211> LENGTH: 414
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
atggagtttg ggctgagctg ggttttcctc gttgctcttt taagaggtgt ccagtgtcag      60
gtgcagctgg tggagtctgg gggaggcgtg gtccagcctg gaggtccct gagactctcc     120 tgtgcagcgt ctggattcac cttcagtagt tatgacatgc actgggtccg ccaggctcca     180 ggcaagggc tggagtgggt ggcagttata tggtatgatg aagtaataa atactatgca      240 gactccgtga agggccgatt caccatctcc agagacaatt ccaagaacac gctgtatctc     300
caaatgaaca gcctgagagc cgaggacacg gctgtgtatt actgtgcgag aggtagtggt     360 aactgggtt ctttgacta ctggggccag ggaaccctgg tcaccgtctc ctca            414

<210> SEQ ID NO 36
<211> LENGTH: 138
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Asp Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Ser Gly Asn Trp Gly Phe Phe Asp Tyr Trp
        115                 120                 125

Gly Gln Gly Thr Leu Val Thr Val Ser Ser
    130                 135

<210> SEQ ID NO 37
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Asn Trp Gly Phe Phe Asp Tyr Trp Gly Gln Gly
            100                 105                 110

Thr Leu Val Thr Val Ser Ser
        115

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 38

Gly Phe Thr Phe Ser Ser Tyr Asp
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Trp Tyr Asp Gly Ser Asn Lys
1               5

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Arg Gly Ser Gly Asn Trp Gly Phe Phe Asp Tyr
1               5                   10

<210> SEQ ID NO 41
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
atgagggtcc tcgctcagct cctggggctc ctgctgctct gtttcccagg tgccagatgt      60
gacatccaga tgacccagtc tccatcctca ctgtctgcat ctgtaggaga cagagtcacc     120
atcacttgtc gggcgagtca gggtattagc aggtggttag cctggtatca gcagaaacca     180
gagaaagccc ctaagtccct gatctatgct gcatccagtt tgcaaagtgg ggtcccatca     240
aggttcagcg gcagtggatc tgggacagat ttcactctca ccatcagcag cctgcagcct     300
gaagattttg caacttatta ctgccaacag tataatactt accctcggac gttcggccaa     360
gggaccaagg tggaaatcaa a                                               381

<210> SEQ ID NO 42
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Arg Val Leu Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
                20                  25                  30

Ala Ser Val Gly Asp Arg Val Thr Ile Thr Cys Arg Ala Ser Gln Gly
            35                  40                  45

```
Ile Ser Arg Trp Leu Ala Trp Tyr Gln Gln Lys Pro Glu Lys Ala Pro
    50                  55                  60
Lys Ser Leu Ile Tyr Ala Ala Ser Ser Leu Gln Ser Gly Val Pro Ser
65                  70                  75                  80
Arg Phe Ser Gly Ser Gly Ser Gly Thr Asp Phe Thr Leu Thr Ile Ser
                85                  90                  95
Ser Leu Gln Pro Glu Asp Phe Ala Thr Tyr Tyr Cys Gln Gln Tyr Asn
            100                 105                 110
Thr Tyr Pro Arg Thr Phe Gly Gln Gly Thr Lys Val Glu Ile Lys
        115                 120                 125
```

```
<210> SEQ ID NO 43
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Ser Arg Trp
            20                  25                  30
Leu Ala Trp Tyr Gln Gln Lys Pro Glu Lys Ala Pro Lys Ser Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Asn Thr Tyr Pro Arg
                85                  90                  95
Thr Phe Gly Gln Gly Thr Lys Val Glu Ile Lys
            100                 105
```

```
<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gly Ile Ser Arg Trp
1               5
```

```
<210> SEQ ID NO 45
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Ala Ser
1
```

```
<210> SEQ ID NO 46
<211> LENGTH: 9
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 46

Gln Gln Tyr Asn Thr Tyr Pro Arg Thr
1               5

<210> SEQ ID NO 47
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
atggagtttg ggctgagctg ggttttcctc gttgctcttt taagaggtgt ccagtgtcag      60
gtgcagctgg tggagtctgg gggaggcgtg gtccagcctg gaggtccct gagactctcc     120 tgtgcagcgt ctggattcac cttcaatatc tatgacatgc actgggtccg ccaggctcca    180
ggcaaggggc tggagtgggt ggcagttata tggtatgatg aagtaatca atactatgca     240 gactccgtga agggccgatt caccatctcc agagacaatt ccaagaacac gctgtatctg    300
caaatgaaca ttttgagagc cgaggacacg gctgtgtatt actgtgcgag aggtactcac    360
tgggggtact ttgactactg gggccaggga accctggtca ccgtctcctc a             411
```

<210> SEQ ID NO 48
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Asn Ile Tyr Asp Met His Trp Val Arg Gln Ala Pro Gly Lys Gly Leu
    50                  55                  60

Glu Trp Val Ala Val Ile Trp Tyr Asp Gly Ser Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ile Leu Arg Ala Glu Asp Thr Ala Val
            100                 105                 110

Tyr Tyr Cys Ala Arg Gly Thr His Trp Gly Tyr Phe Asp Tyr Trp Gly
        115                 120                 125

Gln Gly Thr Leu Val Thr Val Ser Ser
    130                 135

<210> SEQ ID NO 49
<211> LENGTH: 118
<212> TYPE: PRT
<213> ORGANISM: Artificial Sequence
<220> FEATURE:

<223> OTHER INFORMATION: Description of Artificial Sequence: Synthetic
       polypeptide

<400> SEQUENCE: 49

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Ile Tyr
            20                  25                  30

Asp Met His Trp Val Arg Gln Ala Pro Gly Lys Gly Leu Glu Trp Val
        35                  40                  45

Ala Val Ile Trp Tyr Asp Gly Ser Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ile Leu Arg Ala Glu Asp Thr Ala Val Tyr Tyr Cys
                85                  90                  95

Ala Arg Gly Thr His Trp Gly Tyr Phe Asp Tyr Trp Gly Gln Gly Thr
            100                 105                 110

Leu Val Thr Val Ser Ser
        115

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Phe Thr Phe Asn Ile Tyr Asp
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Trp Tyr Asp Gly Ser Asn Gln
1               5

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Arg Gly Thr His Trp Gly Tyr Phe Asp Tyr
1               5                   10

<210> SEQ ID NO 53
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
atgagggtcc tcgctcagct cctggggctc ctgctgctct gtttcccagg tgccagatgt      60
gacatccaga tgacccagtc tccatcctca ctgtctgcat ctgtaggaga cagagtcacc     120
atcacttgtc gggcgagtca gggtattagc agctggttag cctggtatca gcagaaacca     180
gagaaagccc ctaagtccct gatctatgct gcatccaatt tgcaaagtgg ggtcccatca     240
aggttcagcg gcagtggatc tgggacagat ttcactctca ccatcagcag cctgcagcct     300
gaagattttg caacttatta ctgccaacag tataatagtt accctcggac gttcggccaa     360
gggaccaagg tggaaatcaa a                                               381
```

<210> SEQ ID NO 54
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Met Arg Val Leu Ala Gln Leu Leu Gly Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser Ser Trp Leu Ala Trp Tyr Gln Gln Lys Pro Glu Lys Ala Pro
    50                  55                  60

Lys Ser Leu Ile Tyr Ala Ala Ser Asn Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Asn
            100                 105                 110

Ser Tyr Pro Arg Thr Phe Gly Gln Gly Thr Lys Val Glu Ile Lys
        115                 120                 125
```

<210> SEQ ID NO 55
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Asn Ser Tyr Pro Arg
            85                  90                  95

Thr Phe Gly Gln Gly Thr Lys Val Glu Ile Lys
            100                 105

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gly Ile Ser Ser Trp
1               5

<210> SEQ ID NO 57
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Ala Ser
1

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Gln Tyr Asn Ser Tyr Pro Arg Thr
1               5

<210> SEQ ID NO 59
<211> LENGTH: 423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
atggagtttg ggctgagctg ggttttcctc gttgctcttt taagaggtgt ccagtgtcag      60
gtgcaactgg tggagtctgg gggaggcgtg gtccagcctg gaggtccct gagactctcc     120 tgtgcagcgt ctggattcag cttcagtagc tatggcatgc actgggtccg ccaggctcca    180
ggcaagggac tggagtgggt ggcacttcta tggtatgatg gtagccataa agactttgca    240
gactccgtga agggccgatt caccatctcc agagacaatt ccaagaacac gctagatctg    300
caaatgaaca gcctgagagc cgaggacacg gctgtgtatt actgtgcgag agagggttta    360
gcagtacctg gtcactggta cttcgatctc tggggccgtg gcaccctggt cactgtctcc    420
tca                                                                   423

<210> SEQ ID NO 60
<211> LENGTH: 141
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 60

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Ser Phe
        35                  40                  45

Ser Ser Tyr Gly Met His Trp Val Arg Gln Ala Pro Gly Lys Gly Leu
    50                  55                  60

Glu Trp Val Ala Leu Leu Trp Tyr Asp Gly Ser His Lys Asp Phe Ala
65                  70                  75                  80

Asp Ser Val Lys Gly Arg Phe Thr Ile Ser Arg Asp Asn Ser Lys Asn
                85                  90                  95

Thr Leu Asp Leu Gln Met Asn Ser Leu Arg Ala Glu Asp Thr Ala Val
            100                 105                 110

Tyr Tyr Cys Ala Arg Glu Gly Leu Ala Val Pro Gly His Trp Tyr Phe
        115                 120                 125

Asp Leu Trp Gly Arg Gly Thr Leu Val Thr Val Ser Ser
    130                 135                 140

<210> SEQ ID NO 61
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Trp Val
        35                  40                  45

Ala Leu Leu Trp Tyr Asp Gly Ser His Lys Asp Phe Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Arg Glu Gly Leu Ala Val Pro Gly His Trp Tyr Phe Asp Leu Trp
            100                 105                 110

Gly Arg Gly Thr Leu Val Thr Val Ser Ser
        115                 120

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Trp Tyr Asp Gly Ser His Lys
1               5

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Arg Glu Gly Leu Ala Val Pro Gly His Trp Tyr Phe Asp Leu
1               5                   10                  15

<210> SEQ ID NO 65
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
atgagggtcc ccgctcagct cctggggctt ctgctgctct ggctcccagg tgccagatgt    60
gccatccagt tgacccagtc tccatcctcc ctgtctgcat ctgtaggaga cagagtcacc   120
atcacttgcc gggcaagtca gggcattagc agtgctttag cctggtatca gcagaaacca   180
gggaaagctc ctaagctcct gatctatgat gcctccagtt tggaaagtgg ggtcccatca   240
aggttcagcg gcagtggatc tgggacagat ttcactctca ccatcagcag cctgcagcct   300
gaagattttg caacttatta ctgtcaacag tttaatactt accctcggac gttcggccaa   360
gggaccaagg tggaaatcaa a                                             381

<210> SEQ ID NO 66
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Arg Val Pro Ala Gln Leu Leu Gly Leu Leu Leu Leu Trp Leu Pro
1               5                   10                  15

Gly Ala Arg Cys Ala Ile Gln Leu Thr Gln Ser Pro Ser Ser Leu Ser
                20                  25                  30

Ala Ser Val Gly Asp Arg Val Thr Ile Thr Cys Arg Ala Ser Gln Gly
            35                  40                  45

Ile Ser Ser Ala Leu Ala Trp Tyr Gln Gln Lys Pro Gly Lys Ala Pro
        50                  55                  60

Lys Leu Leu Ile Tyr Asp Ala Ser Ser Leu Glu Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Phe Asn
            100                 105                 110

Thr Tyr Pro Arg Thr Phe Gly Gln Gly Thr Lys Val Glu Ile Lys
        115                 120                 125

<210> SEQ ID NO 67
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Thr Tyr Pro Arg
                85                  90                  95

Thr Phe Gly Gln Gly Thr Lys Val Glu Ile Lys
            100                 105

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gly Ile Ser Ser Ala
1               5

<210> SEQ ID NO 69
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Ala Ser
1

<210> SEQ ID NO 70
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 70

Gln Gln Phe Asn Thr Tyr Pro Arg Thr
1               5

<210> SEQ ID NO 71
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
atggagtttg ggctgagctg ggttttcctc gttgctcttt taagaggtgt ccagtgtcag      60
gtgcagttgg tggagtctgg gggaggcgtg gtccagcctg gaggtccct gcgactctcc     120 tgtgcagcgt ctggattcac cctcagtagc catgacatac actgggtccg ccaggctcca    180
ggcaaggggc tggagtgggt ggcagttata tggaatgatg gaagtaataa atactatgca    240
gactccgtga aggccgatt caccatctcc agagacaatt ccacgaactc gctgtttctg     300
caaatgaaca gcctgagagc cgaggacacg gctgtgtatt attgtgtgag aggaactgct    360
gaccttgaac actgggacca gggaaccctg gtcaccgtct cctca                    405

<210> SEQ ID NO 72
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Leu
        35                  40                  45

Ser Ser His Asp Ile His Trp Val Arg Gln Ala Pro Gly Lys Gly Leu
    50                  55                  60

Glu Trp Val Ala Val Ile Trp Asn Asp Gly Ser Asn Lys Tyr Tyr Ala
65                  70                  75                  80

Asp Ser Val Lys Gly Arg Phe Thr Ile Ser Arg Asp Asn Ser Thr Asn
                85                  90                  95

Ser Leu Phe Leu Gln Met Asn Ser Leu Arg Ala Glu Asp Thr Ala Val
            100                 105                 110

Tyr Tyr Cys Val Arg Gly Thr Ala Asp Leu Glu His Trp Asp Gln Gly
        115                 120                 125

Thr Leu Val Thr Val Ser Ser
    130                 135

<210> SEQ ID NO 73
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Leu Ser Ser His
            20                  25                  30

Asp Ile His Trp Val Arg Gln Ala Pro Gly Lys Gly Leu Glu Trp Val
        35                  40                  45

Ala Val Ile Trp Asn Asp Gly Ser Asn Lys Tyr Tyr Ala Asp Ser Val
    50                  55                  60

Lys Gly Arg Phe Thr Ile Ser Arg Asp Asn Ser Thr Asn Ser Leu Phe
65                  70                  75                  80

Leu Gln Met Asn Ser Leu Arg Ala Glu Asp Thr Ala Val Tyr Tyr Cys
                85                  90                  95

Val Arg Gly Thr Ala Asp Leu Glu His Trp Asp Gln Gly Thr Leu Val
            100                 105                 110

Thr Val Ser Ser
        115

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Phe Thr Leu Ser Ser His Asp
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ile Trp Asn Asp Gly Ser Asn Lys
1               5

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Val Arg Gly Thr Ala Asp Leu Glu His Trp Asp Gln
1               5                   10

<210> SEQ ID NO 77
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
atgagggtcc tcgctcagct cctggggctc ctgctgctct gtttcccagg tgccagatgt    60
gacatccaga tgacccagtc tccatcctca ctgtctgcat ctgtaggaga cagagtcacc   120
atcacttgtc gggcgagtca gggtattagc agctggttag cctggtatca gcagaaacca   180
gagaaagccc ctaagtccct gatctatgct gcatccagtt tgcaaagtgg ggtcccatca   240
aggttcagcg gcagtggatc tgggacagat ttcactctca ccatcagcag cctgcagcct   300
gaagattttg caacttatta ctgccaacag tataatagtt accctctcac tttcggcgga   360
gggaccaagg tggagatcaa a                                              381
```

<210> SEQ ID NO 78
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Met Arg Val Leu Ala Gln Leu Leu Gly Leu Leu Leu Cys Phe Pro
1               5                   10                  15

Gly Ala Arg Cys Asp Ile Gln Met Thr Gln Ser Pro Ser Ser Leu Ser
                20                  25                  30

Ala Ser Val Gly Asp Arg Val Thr Ile Thr Cys Arg Ala Ser Gln Gly
            35                  40                  45

Ile Ser Ser Trp Leu Ala Trp Tyr Gln Gln Lys Pro Glu Lys Ala Pro
        50                  55                  60

Lys Ser Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Asn
            100                 105                 110

Ser Tyr Pro Leu Thr Phe Gly Gly Gly Thr Lys Val Glu Ile Lys
        115                 120                 125
```

<210> SEQ ID NO 79
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95
```

Thr Phe Gly Gly Gly Thr Lys Val Glu Ile Lys
            100                 105

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Gly Ile Ser Ser Trp
1               5

<210> SEQ ID NO 81
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Ala Ser
1

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gln Gln Tyr Asn Ser Tyr Pro Leu Thr
1               5

<210> SEQ ID NO 83
<211> LENGTH: 429
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
atggagtttg ggctgagctg ggttttcctc gttgctcttt taagaggtgt ccagtgtcag      60
gtgcagctgg tggagtctgg gggaggcgtg gtccagcctg ggaggtccct gagactctcc     120
tgtgcagcgt ctggattcac cttcagtcat tatggcatgc actgggtccg ccaggctcca     180 ggcaagggc cggagtgggt ggcaattata tggtatgatg gaagtaataa atactatgca     240
gactccgtga agggccgatt caccatctcc agagacaatt ccaagaacac gctggatctg     300
caaatgaaca gcctgagagc cgaggacacg gctgtgtatt actgtgcgag agatggatgg     360
actactatgg ttcgggact taatgttttt gatatctggg gccaagggac aatggtcacc     420
gtctcttca                                                            429

<210> SEQ ID NO 84
<211> LENGTH: 143
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser His Tyr Gly Met His Trp Val Arg Gln Ala Pro Gly Lys Gly Pro
    50                  55                  60

Glu Trp Val Ala Ile Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Asp Leu Gln Met Asn Ser Leu Arg Ala Glu Asp Thr Ala Val
            100                 105                 110

Tyr Tyr Cys Ala Arg Asp Gly Trp Thr Thr Met Val Arg Gly Leu Asn
        115                 120                 125

Val Phe Asp Ile Trp Gly Gln Gly Thr Met Val Thr Val Ser Ser
    130                 135                 140

<210> SEQ ID NO 85
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser His Tyr
            20                  25                  30

Gly Met His Trp Val Arg Gln Ala Pro Gly Lys Gly Pro Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Arg Asp Gly Trp Thr Thr Met Val Arg Gly Leu Asn Val Phe Asp
            100                 105                 110

Ile Trp Gly Gln Gly Thr Met Val Thr Val Ser Ser
        115                 120

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Phe Thr Phe Ser His Tyr Gly
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Ile Trp Tyr Asp Gly Ser Asn Lys
1               5

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Ala Arg Asp Gly Trp Thr Thr Met Val Arg Gly Leu Asn Val Phe Asp
1               5                   10                  15

Ile

<210> SEQ ID NO 89
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

```
atgagggtcc tcgctcagct cctggggctc ctgctgctct gtttcccagg tgccagatgt      60
gacatccaga tgacccagtc tccatcctca ctgtctgcat ctgtaggaga cagagtcacc     120
atcacttgtc gggcgagtca ggatattagc agctggttag cctggtatca gcagaaacca     180
gagaaagccc ctaagtccct gatctatgct gcatccagtt tgcaaagtgg ggtcccatca     240
aggttcagcg gcagtggatc tgggacagat ttcactctca ccatcagcag cctgcagcct     300
gaagattttg caactattat ctgccaacag tataatagtt accctcccac cttcggccaa     360
gggacacgac tggagattaa a                                               381
```

<210> SEQ ID NO 90
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

Met Arg Val Leu Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Ile Ser Ser Trp Leu Ala Trp Tyr Gln Gln Lys Pro Glu Lys Ala Pro
    50                  55                  60

```
Lys Ser Leu Ile Tyr Ala Ala Ser Ser Leu Gln Ser Gly Val Pro Ser
 65                  70                  75                  80

Arg Phe Ser Gly Ser Gly Ser Gly Thr Asp Phe Thr Leu Thr Ile Ser
                 85                  90                  95

Ser Leu Gln Pro Glu Asp Phe Ala Thr Tyr Tyr Cys Gln Gln Tyr Asn
            100                 105                 110

Ser Tyr Pro Pro Thr Phe Gly Gln Gly Thr Arg Leu Glu Ile Lys
        115                 120                 125
```

```
<210> SEQ ID NO 91
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Pro
                 85                  90                  95

Thr Phe Gly Gln Gly Thr Arg Leu Glu Ile Lys
            100                 105
```

```
<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Asp Ile Ser Ser Trp
  1               5
```

```
<210> SEQ ID NO 93
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ala Ala Ser
  1
```

```
<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 94

Gln Gln Tyr Asn Ser Tyr Pro Pro Thr
1               5

<210> SEQ ID NO 95
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95

```
atgagggtcc tcgctcagct cctggggctt ctgctgctct ggctcccagg tgccagatgt    60
gccatccagt tgacccagtc tccatcctcc ctgtctgcat ctgtaggaga cagagtcacc   120
atcacttgcc gggcaagtca gggcattagc agtgctttag cctggtatca gcagaaacca   180
gagaaagccc ctaagtccct gatctatgct gcatccagtt tgcaaagtgg ggtcccatca   240
aggttcagcg gcagtggatc tgggacagat ttcactctca ccatcagcag cctgcagcct   300
gaagattttg caacttatta ctgccaacag tataatagtt accctcccac cttcggccaa   360
gggacacgac tggagattaa a                                             381
```

<210> SEQ ID NO 96
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Arg Val Leu Ala Gln Leu Leu Gly Leu Leu Leu Trp Leu Pro
1               5                   10                  15

Gly Ala Arg Cys Ala Ile Gln Leu Thr Gln Ser Pro Ser Ser Leu Ser
                20                  25                  30

Ala Ser Val Gly Asp Arg Val Thr Ile Thr Cys Arg Ala Ser Gln Gly
            35                  40                  45

Ile Ser Ser Ala Leu Ala Trp Tyr Gln Gln Lys Pro Glu Lys Ala Pro
        50                  55                  60

Lys Ser Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Asn
                100                 105                 110

Ser Tyr Pro Pro Thr Phe Gly Gln Gly Thr Arg Leu Glu Ile Lys
            115                 120                 125

<210> SEQ ID NO 97
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

```
Ala Ile Gln Leu Thr Gln Ser Pro Ser Ser Leu Ser Ala Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Arg Leu Glu Ile Lys
            100                 105

<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Gly Ile Ser Ser Ala
1               5

<210> SEQ ID NO 99
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Ala Ser
1

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Gln Tyr Asn Ser Tyr Pro Pro Thr
1               5

<210> SEQ ID NO 101
<211> LENGTH: 414
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
atggagtttg ggctgagctg ggttttcctc gttgctcttt taagaggtgt ccagtgtcag    60
gtgcagctgg tggagtctgg gggaggcgtg gtccagcctg ggaggtccct gagactctcc   120
tgtgcaacgt ctggattcac cttcagtagc tatgacatgc actgggtccg ccaggctcca   180
```

```
ggcaagggc tggagtgggt ggcagttatt tggtatgatg gaagtaataa atactatgca    240
gactccgtga agggccgatt caccatctcc agagacaatt ccaagaacac gctgtatctc    300
caaatgaaca gcctgggaga cgaggacacg gctgtgtatt actgtgcgag aggtagtggt    360 aactgggtt tctttgacta ctggggccag ggaaccctgg tcaccgtctc ctca           414
```

<210> SEQ ID NO 102
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Thr Ser Gly Phe Thr Phe
        35                  40                  45

Ser Ser Tyr Asp Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Gly Asp Glu Asp Thr Ala Val
            100                 105                 110

Tyr Tyr Cys Ala Arg Gly Ser Gly Asn Trp Gly Phe Phe Asp Tyr Trp
        115                 120                 125

Gly Gln Gly Thr Leu Val Thr Val Ser Ser
    130                 135

<210> SEQ ID NO 103
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Val Gln Leu Val Glu Ser Gly Gly Gly Val Val Gln Pro Gly Arg
1               5                   10                  15

Ser Leu Arg Leu Ser Cys Ala Thr Ser Gly Phe Thr Phe Ser Ser Tyr
            20                  25                  30

Asp Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Gly Asp Glu Asp Thr Ala Val Tyr Tyr Cys
                85                  90                  95

Ala Arg Gly Ser Gly Asn Trp Gly Phe Phe Asp Tyr Trp Gly Gln Gly
            100                 105                 110

```
<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Phe Thr Phe Ser Ser Tyr Asp
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ile Trp Tyr Asp Gly Ser Asn Lys
1               5

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ala Arg Gly Ser Gly Asn Trp Gly Phe Phe Asp Tyr
1               5                   10

<210> SEQ ID NO 107
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
atgagggtcc tcgctcagct cctggggctc ctgctgctct gtttcccagg tgccagatgt      60
gacatccaga tgacccagtc tccatcctca ctgtctgcat ctgtaggaga cagagtcacc     120
atcacttgtc gggcgagtca gggtattagc aggtggttag cctggtatca gcagaaacca     180
gagaaagccc ctaagtccct gatctatgct gcatccagtt tgcaaagtgg ggtcccatca     240
aggttcagcg gcagtggatc tgggacagat ttcactctca ccatcagcag cctgcagcct     300
gaagattttg caacttatta ctgccaacag tataatactt accctcggac gttcggccaa     360
gggaccaagg tggaaatcaa a                                               381

<210> SEQ ID NO 108
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide
```

Thr Leu Val Thr Val Ser Ser
        115

-continued

```
<400> SEQUENCE: 108

Met Arg Val Leu Ala Gln Leu Leu Gly Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser Arg Trp Leu Ala Trp Tyr Gln Gln Lys Pro Glu Lys Ala Pro
    50                  55                  60

Lys Ser Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Asn
            100                 105                 110

Thr Tyr Pro Arg Thr Phe Gly Gln Gly Thr Lys Val Glu Ile Lys
        115                 120                 125

<210> SEQ ID NO 109
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Thr Tyr Pro Arg
                85                  90                  95

Thr Phe Gly Gln Gly Thr Lys Val Glu Ile Lys
            100                 105

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Gly Ile Ser Arg Trp
1               5

<210> SEQ ID NO 111
<211> LENGTH: 3
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 111

Ala Ala Ser
1

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Gln Tyr Asn Thr Tyr Pro Arg Thr
1               5

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Gly, Glu, or Asp
<220> FEATURE:
<221> NAME/KEY: MOD_RES
<222> LOCATION: (3)..(3)
<223> OTHER INFORMATION: Ser, Leu, Gly, or absent
<220> FEATURE:
<221> NAME/KEY: MOD_RES
<222> LOCATION: (4)..(4)
<223> OTHER INFORMATION: Gly, Leu, Thr, Trp, or absent
<220> FEATURE:
<221> NAME/KEY: MOD_RES
<222> LOCATION: (5)..(5)
<223> OTHER INFORMATION: Asn, Ala, Thr, His, or absent
<220> FEATURE:
<221> NAME/KEY: MOD_RES
<222> LOCATION: (6)..(6)
<223> OTHER INFORMATION: Val, Thr, or absent
<220> FEATURE:
<221> NAME/KEY: MOD_RES
<222> LOCATION: (7)..(7)
<223> OTHER INFORMATION: Met, Pro, or absent
<220> FEATURE:
<221> NAME/KEY: MOD_RES
<222> LOCATION: (8)..(8)
<223> OTHER INFORMATION: Gly, Val, or absent
<220> FEATURE:
<221> NAME/KEY: MOD_RES
<222> LOCATION: (9)..(9)
<223> OTHER INFORMATION: May or may not be present
<220> FEATURE:
<221> NAME/KEY: MOD_RES
<222> LOCATION: (10)..(10)
<223> OTHER INFORMATION: Gly, Met, or absent
<220> FEATURE:
<221> NAME/KEY: MOD_RES
<222> LOCATION: (11)..(11)
<223> OTHER INFORMATION: Asp, His, Leu, Thr, or Trp
<220> FEATURE:
<221> NAME/KEY: MOD_RES
<222> LOCATION: (12)..(12)
<223> OTHER INFORMATION: Ala, Gly, Asn, or Trp
<220> FEATURE:
<221> NAME/KEY: MOD_RES
<222> LOCATION: (13)..(13)
<223> OTHER INFORMATION: Asp, Phe, Val, or Tyr
<220> FEATURE:
<221> NAME/KEY: MOD_RES

```
<222> LOCATION: (14)..(14)
<223> OTHER INFORMATION: Phe or Leu
<220> FEATURE:
<221> NAME/KEY: MOD_RES
<222> LOCATION: (15)..(15)
<223> OTHER INFORMATION: Asp or Glu
<220> FEATURE:
<221> NAME/KEY: MOD_RES
<222> LOCATION: (16)..(16)
<223> OTHER INFORMATION: His, Ile, Leu, or Tyr

<400> SEQUENCE: 113

Arg Xaa Xaa Xaa Xaa Xaa Xaa Arg Xaa Xaa Xaa Xaa Xaa Xaa Xaa
1               5                   10                  15

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Phe, Arg, or Tyr
<220> FEATURE:
<221> NAME/KEY: MOD_RES
<222> LOCATION: (3)..(3)
<223> OTHER INFORMATION: Asn or Ser
<220> FEATURE:
<221> NAME/KEY: MOD_RES
<222> LOCATION: (4)..(4)
<223> OTHER INFORMATION: Asn, Thr, or Ser
<220> FEATURE:
<221> NAME/KEY: MOD_RES
<222> LOCATION: (5)..(5)
<223> OTHER INFORMATION: Tyr or Trp
<220> FEATURE:
<221> NAME/KEY: MOD_RES
<222> LOCATION: (7)..(7)
<223> OTHER INFORMATION: Phe, Leu, Pro, or Arg

<400> SEQUENCE: 114

Gln Xaa Xaa Xaa Xaa Pro Xaa Thr
1               5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Lys or Trp
<220> FEATURE:
<221> NAME/KEY: MOD_RES
<222> LOCATION: (3)..(3)
<223> OTHER INFORMATION: Tyr, Asn, or Gln
<220> FEATURE:
<221> NAME/KEY: MOD_RES
<222> LOCATION: (7)..(7)
<223> OTHER INFORMATION: Glu or Asn
<220> FEATURE:
<221> NAME/KEY: MOD_RES
<222> LOCATION: (8)..(8)
<223> OTHER INFORMATION: Lys or Gln

<400> SEQUENCE: 115

Ile Xaa Xaa Asp Gly Ser Xaa Xaa
1               5
```

```
<210> SEQ ID NO 116
<211> LENGTH: 3
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Ala or Asp

<400> SEQUENCE: 116

Xaa Ala Ser
1

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (3)..(3)
<223> OTHER INFORMATION: Thr or Ser
<220> FEATURE:
<221> NAME/KEY: MOD_RES
<222> LOCATION: (4)..(4)
<223> OTHER INFORMATION: Phe or Leu
<220> FEATURE:
<221> NAME/KEY: MOD_RES
<222> LOCATION: (5)..(5)
<223> OTHER INFORMATION: Ser or Asn
<220> FEATURE:
<221> NAME/KEY: MOD_RES
<222> LOCATION: (6)..(6)
<223> OTHER INFORMATION: Ile, Ser, or His
<220> FEATURE:
<221> NAME/KEY: MOD_RES
<222> LOCATION: (7)..(7)
<223> OTHER INFORMATION: Tyr or His

<400> SEQUENCE: 117

Gly Phe Xaa Xaa Xaa Xaa Xaa
1               5

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(2)
<223> OTHER INFORMATION: Asp, Gly, or Ser
<220> FEATURE:
<221> NAME/KEY: MOD_RES
<222> LOCATION: (3)..(3)
<223> OTHER INFORMATION: Ile or Val
<220> FEATURE:
<221> NAME/KEY: MOD_RES
<222> LOCATION: (4)..(4)
<223> OTHER INFORMATION: Asp or Ser
<220> FEATURE:
<221> NAME/KEY: MOD_RES
<222> LOCATION: (5)..(5)
<223> OTHER INFORMATION: Arg or Ser
<220> FEATURE:
<221> NAME/KEY: MOD_RES
```

```
<222> LOCATION: (6)..(6)
<223> OTHER INFORMATION: Ala, Trp, or Tyr

<400> SEQUENCE: 118

Gln Xaa Xaa Xaa Xaa Xaa
1               5

<210> SEQ ID NO 119
<211> LENGTH: 8
<212> TYPE: PRT
<213> ORGANISM: Gallus sp.

<400> SEQUENCE: 119

Ser Ile Ile Asn Phe Glu Lys Leu
1               5

<210> SEQ ID NO 120
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Met Arg Val Pro Ala Gln Leu Leu Gly Leu Leu Leu Trp Leu Pro
1               5                   10                  15

Gly Ala Arg Cys Ala Ile Gln Leu Thr Gln Ser Pro Ser Ser Leu Ser
                20                  25                  30

Ala Ser Val Gly Asp Arg Val Thr Ile Thr Cys Arg Ala Ser Gln Gly
            35                  40                  45

Ile Ser Ser Ala Leu Ala Trp Tyr Gln Gln Lys Pro Gly Lys Ala Pro
        50                  55                  60

Lys Leu Leu Ile Tyr Asp Ala Ser Ser Leu Glu Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Phe Asn
            100                 105                 110

Ser Tyr Pro Phe Thr Phe Gly Pro Gly Thr Lys Val Asp Ile Lys
        115                 120                 125
```